US011191826B2

(12) United States Patent
Munoz Alia et al.

(10) Patent No.: US 11,191,826 B2
(45) Date of Patent: Dec. 7, 2021

(54) MODIFIED VIRUSES

(71) Applicant: Mayo Foundation for Medical Education and Research, Rochester, MN (US)

(72) Inventors: Miguel A. Munoz Alia, Rochester, MN (US); Stephen James Russell, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/612,842

(22) PCT Filed: Apr. 4, 2018

(86) PCT No.: PCT/US2018/026079
§ 371 (c)(1),
(2) Date: Nov. 12, 2019

(87) PCT Pub. No.: WO2018/212842
PCT Pub. Date: Nov. 22, 2018

(65) Prior Publication Data
US 2020/0147204 A1    May 14, 2020

Related U.S. Application Data

(60) Provisional application No. 62/506,892, filed on May 16, 2017.

(51) Int. Cl.
| | | |
|---|---|---|
| *A61K 39/00* | (2006.01) | |
| *C07K 14/705* | (2006.01) | |
| *C12N 7/00* | (2006.01) | |
| *C07K 14/435* | (2006.01) | |
| *C12N 15/00* | (2006.01) | |
| *A61K 39/165* | (2006.01) | |

(52) U.S. Cl.
CPC .............. *A61K 39/165* (2013.01); *C12N 7/00* (2013.01); *A61K 2039/5256* (2013.01); *A61K 2039/55* (2013.01); *C12N 2710/10021* (2013.01); *C12N 2760/18421* (2013.01); *C12N 2760/18422* (2013.01); *C12N 2760/18434* (2013.01)

(58) Field of Classification Search
CPC .... C07K 14/705; C07K 14/005; A61K 38/00; A61K 2300/00; A61P 35/00
See application file for complete search history.

(56) References Cited

U.S. PATENT DOCUMENTS

| | | | |
|---|---|---|---|
| 4,683,195 A | 7/1987 | Mullis et al. | |
| 2014/0024100 A1* | 1/2014 | Russell | C07K 14/005 435/235.1 |

FOREIGN PATENT DOCUMENTS

| | | | |
|---|---|---|---|
| WO | WO 01/020989 | | 3/2001 |
| WO | WO200120989 | * | 3/2001 |
| WO | WO 03/093431 | | 11/2003 |
| WO | WO 2014/015242 | | 1/2014 |

OTHER PUBLICATIONS

Russell, "Measles as a Versatile Oncolytic Agent," Presented at The 10th International Conference on Replicating Oncolytic Virus Therapeutics, Vancouver, Canada from Oct. 1-4, 2016, 45 pages.
Beaty et al., "Efficient and Robust Paramyxoviridae Reverse Genetics Systems," mSphere, 2(2):pp. i00376-16, Mar. 2017.
De Swart et al., "Depletion of Measles Virus Glycoprotein-Specific Antibodies From Human Sera Reveals Genotype-Specific Neutralizing Antibodies," J. Gen. Virol., 90:2982-9, Dec. 2009.
De Swart et al., "Measles Virus Fusion Protein—and Hemagglutinin-Transfected Cell Lines are a Sensitive Tool for the Detection of Specific Antibodies by a FACS-measured Immunofluorescence Assay," J. Virol. Methods, 71(1):35-44, Mar. 1998.
De Swart et al., "Relative Contributions of Measles Virus Hemagglutinin—and Fusion Protein-Specific Serum Antibodies to Virus Neutralization," J. Virol., 79(17):11547-51, Sep. 2005.
Del Valle et al., "A Vectored Measles Virus Induces Hepatitis B Surface Antigen Antibodies While Protecting Macaques Against Measles Virus Challenge," J. Virol., 81(19):10597-605, Oct. 2007.
Extended European Search Report in European Application 18802836.9 dated May 18, 2020, 11 pages.
Finsterbusch et al., "Measles Viruses of Genotype H1 Evade Recognition by Vaccine-Induced Neutralizing Antibodies Targeting the Linear Haemagglutinin Noose Epitope," J. Gen, Virol., 90:2739-45, Nov. 2009.
Fournier et al., "Antibodies to a New Linear Site at the Topographical or Functional Interface Between the Haemagglutinin and Fusion Proteins Protect Against Measles Encephalitis," J. Gen, Virol., 78:1295-302, Jun. 1997.
Fulton et al., "Mutational Analysis of Measles Virus Suggests Constraints on Antigenic Variation of the Glycoproteins," Cell Rep., 11(9):1331-8, Jun. 2015.
Garten et al., "Antigenic and Genetic Characteristics of Swine-Origin 2009 A(H1N1) Influenza Viruses Circulating in Humans," Science, 325(5937):197-201, Jul. 2009.
GenBank Accession No. AAC26995, "haemagglutinin protein H [Canine morbillivirus]," Jul. 21, 1998, 2 pages.

(Continued)

*Primary Examiner* — Barry A Chestnut
(74) *Attorney, Agent, or Firm* — Fish & Richardson P.C.

(57) ABSTRACT

This document relates to methods and materials for making and using viruses (e.g., measles viruses or adenoviruses) having a reduced susceptibility to antibody neutralization (e.g., antibody neutralization by serum from measles virus vaccines). For example, recombinant morbilliviruses (e.g., recombinant measles viruses) having a modified H gene and a modified F gene, as well as methods of using a recombinant virus are provided.

12 Claims, 25 Drawing Sheets
Specification includes a Sequence Listing.

(56) References Cited

OTHER PUBLICATIONS

GenBank Accession No. AAF85672, "fusion protein [Measles virus strain Moraten]," dated Jan. 25, 2001, 1 page.
GenBank Accession No. AAF85673 "hemagglutinin [Measles virus strain Moraten]," dated Jan. 25, 2001, 2 pages.
GenBank Accession No. ABR08390, "fusion protein [Canine morbillivirus]," dated Jun. 12, 2007, 1 page.
GenBank Accession No. KP191044, "Measles virus genotype B3.1 hemagglutinin (H) gene, complete cds," Dec. 12, 2014, 2 pages.
GenBank Accession No. KP205324, "Measles virus genotype B3.1 fusion protein (F) gene, complete cds," Dec. 12, 2014, 2 pages.
Haralambieva et al., A Large Observational Study to Concurrently Assess Persistence of Measles Specific B-cell and T-cell Immunity +A30+A28.
Hashiguchi et al., "Crystal structure of measles virus hemagglutinin provides insight into effective vaccines," Proceedings of the National Academy of Sciences, 104(49):19535-40, Dec. 2007.
Hensley et al., "Hemagglutinin Receptor Binding Avidity Drives Influenza A Virus Antigenic Drift," Science, 326(5953):734-6, Oct. 2009.
Hu et al., "Molecular Characterization of Epitopes on the Measles Virus Hemagglutinin Protein," Virology, 192(1):351-4, Jan. 1993.
Hummel and Bellini, "Localization of Monoclonal Antibody Epitopes and Functional Domains in the Hemagglutinin Protein of Measles Virus," J. Virol., 69(3):1913-16, Mar. 1995.
International Preliminary Report on Patentability in International Application No. PCT/US2018/026079 dated Nov. 28, 2019, 10 pages.
International Search Report & Written Opinion in International Application No. PCT/US2018/026079 dated Aug. 29, 2018, 19 pages.
Itoh et al., "Comparative Analysis of Titers of Antibody Against Measles Virus in Sera of Vaccinated and Naturally Infected Japanese Individuals of Different Age Groups," J. Clin, Microbiol., 40(5):1733-8, May 2002.
Kelley et al., "The Phyre2 Web Portal for Protein Modeling, Prediction and Analysis," Nat. Protoc., 10(6):845-58, Jun. 2015.
Kosik et al., "Influenza A Virus Hemagglutinin Glycosylation Compensates for Antibody Escape Fitness Costs," PLoS Pathog., 14(1):e1006796, Jan. 2018.
Langedijk et al., "Canine Distemper Virus Infects Canine Keratinocytes and Immune Cells by Using Overlapping and Distinct Regions Located on One Side of the Attachment Protein," J. Virol., 85(21):11242-54, Nov. 2011.
Lech et al., "Antibody Neutralization of Retargeted Measles Viruses," Virology, 454-455:237-46, Apr. 2014.
Lech et al., "Epitope Dampening Monotypic Measles Virus Hemagglutinin Glycoprotein Results in Resistance to Cocktail of Monoclonal Antibodies," PLoS One, 8(1):e52306, Jan. 2013.
Lecouturier et al., "Identification of Two Amino Acids in the Hemagglutinin Glycoprotein of Measles Virus (MV) That Govern Hemadsorption, HeLa Cell Fusion, and CD46 Downregulation: Phenotypic Markers That Differentiate Vaccine and Wild-Type MV Strains," J. Virol., 70(7):4200-4, Jul. 1996.
Li and Qi, "A Novel Amino Acid Position in Hemagglutinin Glycoprotein of Measles Virus is Responsible for Hemadsorption and CD46 Binding," Arch. Virol., 147(4):775-86, Apr. 2002.
Li et al., "Single Hemagglutinin Mutations That Alter Both Antigenicity and Receptor Binding Avidity Influence Influenza Virus Antigenic Clustering," J. Virol., 87(17):9904-10, Sep. 2013.
Liebert et al., "Antigenic Determinants of Measles Virus Hemagglutinin Associated with Neurovirulence," J. Virol., 68(3):1486-93, Mar. 1994.
Liu et al., "Ablation of nectin4 Binding Compromises CD46 Usage by a Hybrid Vesicular Stomatitis Virus/Measles Virus," J. Virol., 88(4):2195-204, Feb. 2014.
Liu et al., "Hydrodynamics-based Transfection in Animals by Systemic Administration of Plasmid DNA," Gene Ther., 6(7):1258-66, Jul. 1999.
Masse et al., "Measles Virus (MV) Hemagglutinin: Evidence That Attachment Sites for MV Receptors SLAM and CD46 Overlap on the Globular Head," J. Virol., 78(17):9051-63, Sep. 2004.
Mateo et al., "The Measles Virus Hemagglutinin β-Propeller Head β4-β5 Hydrophobic Groove Governs Functional Interactions with nectin-4 and CD46 but Not Those with the Signaling Lymphocytic Activation Molecule," J. Virol., 87(16):9208-16, Aug. 2013.
Messling et al., "A Ferret Model of Canine Distemper Virus Virulence and Immunosuppression," J. Virol., 77(23):12579-91, Dec. 2003.
Messling et al., "The Hemagglutinin of Canine Distemper Virus Determines Tropism and Cytopathogenicity," J. Virol., 75(14):6418-27, Jul. 2001.
Miest et al., "Envelope-chimeric Entry-Targeted Measles Virus Escapes Neutralization and Achieves Oncolysis," Mol. Ther., 19(10):1813-20, Oct. 2011.
Muñoz-Alía and Russell, Probing morbillivirus antisera neutralization using functional chimerism between measles virus and canine distemper virus envelope glycoproteins, Viruses, 11(8):688, Aug. 2019.
Munoz-Alia et al., "Antigenic Drift Defines a New D4 Subgenotype of Measles Virus," J. Virol., 91(11):e00209-17, May 2017.
Munoz-Alia et al., "Hemagglutinin-specific Neutralization of Subacute Sclerosing Panencephalitis Viruses," PLoS One, 13(2):e0192245, Feb. 2018.
Munoz-Alia et al., "Measles Virus Genetic Evolution Throughout an Imported Epidemic Outbreak in a Highly Vaccinated Population," Virus. Res., 196:122-7, Jan. 2015.
Munoz-Alia et al., "Measles Virus Hemagglutinin Epitopes Immunogenic in Natural Infection and Vaccination Are Targeted by Broad or Genotype-Specific Neutralizing Monoclonal Antibodies," Virus Res., 236:30-43, May 2017.
Nachbagauer et al., "Defining the Antibody Cross-Reactome Directed Against the Influenza Virus Surface Glycoproteins," Nat. Immunol., 18(4):464-73, Apr. 2017.
Nakamura et al., "Antibody-targeted Cell Fusion," Nat. Biotechnol., 22(3):331-6, Mar. 2004.
Nies and Spielberg, "Principles of Therapeutics," In Goodman & Gilman's The Pharmacological Basis of Therapeutics, eds., McGraw-Hill, NY, 1996, pp. 43-62.
Okada et al., "Previously Unrecognized Amino Acid Substitutions in the Hemagglutinin and Fusion Proteins of Measles Virus Modulate Cell-Cell Fusion, Hemadsorption, Virus Growth, and Penetration Rate," J. Virol., 83(17):8713-21, Sep. 2009.
Ono et al., "Measles Viruses on Throat Swabs From Measles Patients Use Signaling Lymphocytic Activation Molecule (CDw150) but Not CD46 as a Cellular Receptor," J, Virol., 75(9):4399-401, May 2001.
Rima et al., "Sequence Divergence of Measles Virus Haemagglutinin During Natural Evolution and Adaptation to Cell Culture," J. Gen. Virol., 78:97-106, Jan. 1997.
Russell et al., "Influenza Vaccine Strain Selection and Recent Studies on the Global Migration of Seasonal Influenza Viruses," Vaccine, 26(Suppl 4):D31-4, Sep. 2008.
Santibanez et al., "Probing Neutralizing-Antibody Responses Against Emerging Measles Viruses (MVs): Immune Selection of MV by H Protein-Specific Antibodies?," J. Gen. Virol., 86:365-74, Feb. 2005.
Saw et al., "Using a Split Luciferase Assay (SLA) to Measure the Kinetics of Cell-Cell Fusion Mediated by Herpes Simplex Virus Glycoproteins," Methods, 90:68-75, Nov. 2015.
Shibahara et al., "Increased Binding Activity of Measles Virus to Monkey Red Blood Cells After Long-Term Passage in Vero Cell Cultures," J. Gen. Virol., 75:3511-6, Dec. 1994.
Smith et al., "Mapping the Antigenic and Genetic Evolution of Influenza Virus," Science, 305(5682):371-6, Jul. 2004.
Tahara et al., "Functional and Structural Characterization of Neutralizing Epitopes of Measles Virus Hemagglutinin Protein," J. Virol., 87(1):666-75, Jan. 2013.
Tahara et al., "Measles Virus Hemagglutinin Protein Epitopes: The Basis of Antigenic Stability," Viruses, 8(8):216, Jun. 2016.
Tahara et al., "Measles Virus Infects Both Polarized Epithelial and Immune Cells by Using Distinctive Receptor-Binding Sites on Its Hemagglutinin," J. Virol., 82(9):4630-7, May 2008.

(56) References Cited

OTHER PUBLICATIONS

Tamin et al., "Antigenic Analysis of Current Wild Type and Vaccine Strains of Measles Virus," J. Infec. Dis., 170(4):795-801, Oct. 1994.

Tatsuo et al., "SLAM (CDw150) is a Cellular Receptor for Measles Virus," Nature, 406(6798):893-6, Aug. 2000.

Ungerechts et al., "968, Transcriptional Activation of krox-1 Induced by Sexual Hormones in Osteosarcoma Cells," Molecular Therapy, 13:S373-4, Jan. 2006.

UniProtKB/TrEMBL Accession No. W5U2Q7_9MONO, Measles vims genotype H1 Hemagglutinin, Apr. 16, 2014 [online], [Retrieved on Jun. 7, 2018], Retrieved from the internet: <URL: http://www.uniprot.org/uniprot/W5U2Q7>, 4 pages.

Yun et al., "Efficient reverse genetics reveals genetic determinants of budding and fusogenic differences between Nipah and Hendra viruses and enables real-time monitoring of viral spread in small animal models of henipavirus infection," J. Virol., 89(2):1242-53, Jan. 2015.

Zhang et al., "Canine Distemper Virus Neutralization Activity is Low in Human Serum and it is Sensitive to an Amino Acid Substitution in the Hemagglutinin Protein," Virology, 482:218-24, Aug. 2015.

Ziegler et al., "Protection Against Measles Virus Encephalitis by Monoclonal Antibodies Binding to a Cystine Loop Domain of the H Protein Mimicked by Peptides Which Are Not Recognized by Maternal Antibodies," J. Gen. Virol., 77(Pt 10):2479-89, Oct. 1996.

\* cited by examiner

FIG. 4
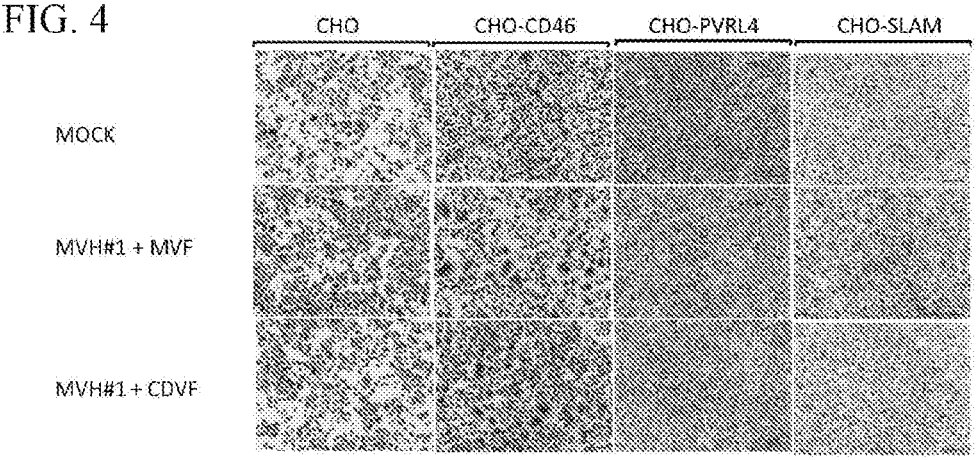
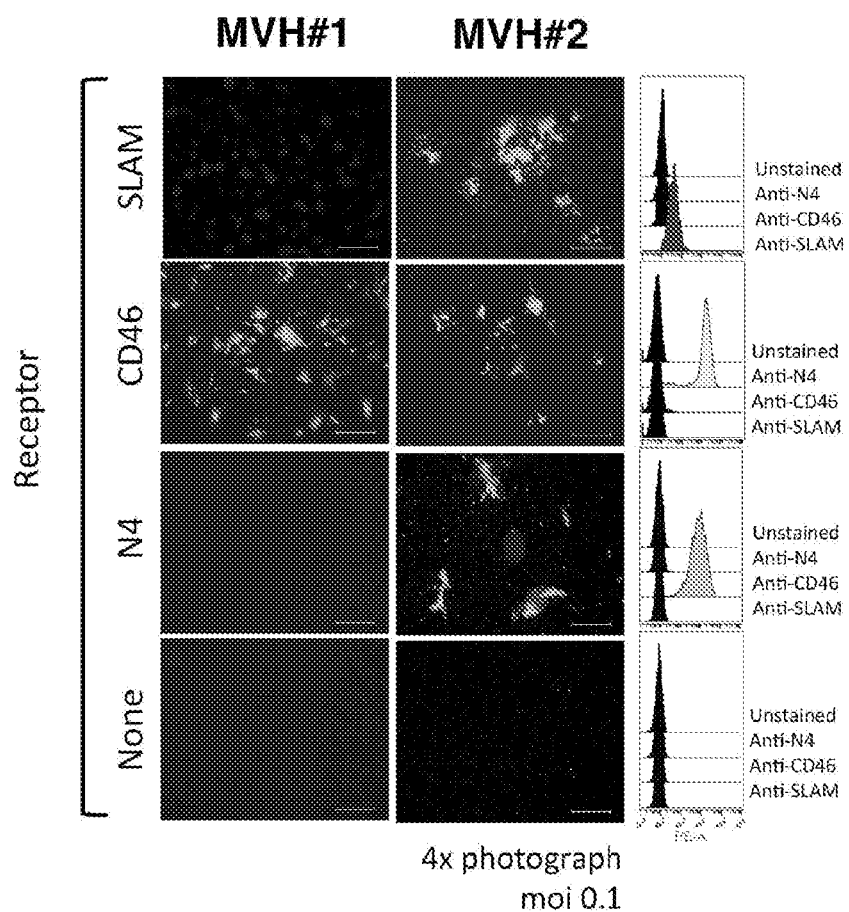
4x photograph
moi 0.1

FIG. 6

```
SEQ ID NO:1
MSPQRDRINAFYKDNPHPKGSRIVINREHLMIDRPYVLLAVLFVMFLSLIGLLAIAGIRLHRAA
IYTAEIHKSLSTNLDVTNSIEHQVKDVLTPLFKIIGDEVGLRTPQRFTDLVKLISDKIKFLNPD
REYDFRDLTWCINPPERIKLDYDQYCADVAAEELMNALVNSTLLETRTTNQFLAVSKGNCSGPT
TIRGQFSNMSLSLLDLYLGRGYNVSSIVTMTSQGMYGGTYLVEKPNLSSKRSELSQLSMYRVFE
VGVIRNPGLGAPVFHMTNYLEQPVSNDLSNCMVALGELKLAALCHGEDSITIPYQGSGKGVSFQ
LVKLGVWKSPTDMQSWVPLSTDDPVIDRLYLSSHRGVIADNQAKWAVPTTRTDDKLRMETCFQQ
ACKGKIQALCENPEWAPLKDNRIPSYGVLSVDLSLTVELKIKIASGFGPLITHGSGMDLYKSNH
NNVYWLTIPPMKNLALGVINTLEWIPRFKVSPYLFTVPIKEAGEDCHAPTYLPAEVDGDVKLSS
NLVILPGQDLQYVLATYDTSRVEHAVVYYVYSPSRSFSYFYPFRLPIKGVPIELQVECFTWDQK
LWCRHFCVLADSESGGHITHSGMVGMVSCTVTREDGTNRR

SEQ ID NO:2
ATGTCACCGCAAAGAGACCGGATAAATGCCTTCTACAAAGATAACCCTTATCCCAAGGGAAGTA
GGATAGTTATTAACAGAGAACATCTTATGATTGACAGACCCTATATTCTGCTGGCTGTTCTGTT
CGTCATGTTTCTGAGCTTGATCGGATTGCTGGCAATTGCAGGCATTAGACTTCATCGGGCAGCC
ATCTACACCGCGGAGATCCATAAAAGCCTCAGTACCAATCTAGATGTGACTAACTCAATCGAGC
ATCAGGTCAAGGACGTGCTGACACCACTCTTTAAAATCATCGGGGATGAAGTGGGCCTGAGAAC
ACCTCAGAGATTCACTGACCTAGTGAAATTCATCTCTGACAAGATTAAATTCCTTAATCCGGAT
AGGGAGTACGACTTCAGAGATCTCACTTGGTGCATCAACCCGCCAGAGAGGATCAAACTAGATT
ATGATCAATACTGTGCAGATGTGGCTGCTGAAGAGCTCATGAATGCATTGGTGAACTCAACTCT
ACTGGAGACCAGAACAACCAATCAGTTCCTAGCTGTCTCAAAGGGAAACTGCTCAGGGCCCACT
ACAATCAGAGGTCAATTCTCAAACATGTCGCTGTCCTTGTTGGACTTGTACTTAGGTCGAGGTT
ACAATGTGTCATCTATAGTCACTATGACATCCCAGGGAATGTATGGGGAACCTACCTAGTGGA
AAAGCCTAATCTGAACAGCAAAGGGTCAGAGTTGTCACAACTGAGCATGTACCGAGTGTTTGAA
GTAGGTGTTATCAGAAACCCGGGTTTGGGGGCTCCGGTGTTCCATATGACAAACTATTTTGAGC
AACCAGTCAGTAATGGTCTCGGCAACTGTATGGTGGCTTTGGGGGAGCTCAAACTCGCAGCCCT
TTGTCACGGGGACGATTCTATCACAATTCCCTATCAGGGATCAGGGAAAGGTGTCAGCTTCCAG
CTCGTCAAGCTGGGTGTCTGGAAATCCCCAACCGACATGCAATCCTGGGTCCCCTTATCAACGG
ATGATCCAGTGGTAGACAGGCTTTACCTCTCATCTCACAGAGGTGTCATCGCTGACAATCAAGC
AAAATGGGCTGTCCCGACAACACGAACAGATGACAAGTTGCGAATGGAGACATGCTTCCAGCAG
GCGTGTAAAGGTAAAATCCAAGCACTCTGCGAGAATCCCGAGTGGGTGCCATTGAAGGATAACA
GGATTCCTTCATACGGGGTCCTGTCTGTTGATCTGAGTCTGACAGTTGAGCTTAAAATCAAAAT
TGCTTCGGGATTCGGGCCATTGATCACACACGGCTCAGGGATGGACCTATACAAATCCAACCGC
AACAATGTGTATTGGCTGACTATTCCGCCAATGAGAAATCTAGCCTTAGGCGTAATCAACACAT
TGGAGTGGATACCGAGATTCAAGGTTAGTCCCAACCTCTTCACTGTCCCAATTAAGGAAGCAGG
CGAGGACTGCCATGCCCCAACATACCTACCTGCGGAGGTGGACGGTGATGTCAAACTCAGTTCC
AACCTGGTGATTCTACCTGGTCAAGATCTCCAATATGTTTTGGCAACCTACGATACCTCCAGGG
TTGAGCATGCTGTGGTTTATTACGTTTACAGCCCAAGCCGCTCATTTTCTTACTTTTATCCTTT
TAGGTTGCCTATAAAGGGGGTCCCAATCGAACTACAAGTGGAATGCTTCACATGGGACCAAAAA
CTCTGGTGCCGTCACTTCTGTGTGCTTGCGGACTCAGAATCCGGCGGACATATCACTCACTCTG
GGATGGTGGGCATGGGAGTCAGCTGCACAGCTACCCGGGAAGATGGAACCAATCGCAGATAA
```

FIG. 6 (cont.)

SEQ ID NO:3
MSPQRDRINAFYKDNPHSKGSRIVINREHLMIDRPYVLLAVLFVMFLSLIGLLAIAGIRLHRA
AIYTAEIHKSLSTNLDVTNSIEHQVKDVLTPLFKIIGDEVGLRTPQRFTDLVKFISDKIKFLN
PDREYDFRDLTWCINPPERIKLNYDQYCADVAAEELMNALVNSTLLETRTTNQFLAVSKGNCP
GPTTIRGQFSNMSLSLLDLYLSRGYNVSSIVTMTSQGMYGGTYLVGKPDLNSKGSELSQPSMY
RVFEVGVIRNPGLGAPVFHMTNYFEQPISKDLSNCMVALGELKLAALCHRGDSITIPCRGSGK
GVSFQLVKLGVWKSPTDMHSWVPLSTDDPVIDRLYLSSHRGVITDNQANWAVPTTRTDDKLQK
ETCFQQACKGKIQALCENLEWAPLKDSRIPSYGVLSVNLSLAAEPKIKIASGFGPLITHGSGM
DLYKSNHNNVYWLTIPPMKNLALGVINTLEWIPRLKVSPYLFTVPIEEADEDCRAPTYLPAEV
TGDVKLSSNLVILPGQDLQYVLATYDTSGVEHAVVYYVYSPGGSFSYVYPFRLPIKGTPIELQ
VECFTWAQRLWCRHFCVLADSESGGHLTHSGMVGMEVSCTVNREDEANRR

SEQ ID NO:4
MSIMGLKVNVSAIFMAVLLTLQTPTGQIHWGNLSKIGVVGIGSASYKVMTRSSHQSLVIKLMPN
ITLLNNCTRVEIAEYRRLLRTVLEPIRDALNAMTQNIRPVQSVASSRRHKRFAGVVLAGAALGV
ATAAQITAGIALHQSMLNSQAIDNLRASLETTNQAIETIRQAGQEMILAVQGVQDYINNELIPS
MNQLSCDLIGQKLGLKLLRYYTEILSLFGPSLRDPISAEISIQALSYALGGDINKVLEKLGYSG
GDLLGILESGGIKARITHVDTESYFIVLSIAYPTLSEIKGVIVHRLEGVSYNIGSQEWYTTVPK
YVATQGYLISNFDESSCTFMPEGTVCSQNALYPMSPLLQECLRGYTKSCARTLVSGSFGNRFIL
SQGNLIANCASILCKCYTTGTIINQDPDKILTYIAADHCPVVEVNGVTIQVGSRRYPDAVYLHR
IDLGPPISLERLDVGTNLGNAIAKLEDAKELLESSDQILRSMKGLSSTSIVYILIAVCLGGLIG
IPALICCCRGRCNKKGEQVGMSRPGLKPDLTGTSKSYVRSL

FIG. 6 (cont.)

```
SEQ ID NO:5
ATGGGTCTCAAGGTGAACGTCTCTGCCGTATTCATGGCAGTACTGTTAACTCTCCAAACACCC
GCCGGTCAAATTCATTGGGGCAATCTCTCTAAGATAGGGGTAGTAGGAATAGGAAGTGCAAGC
TACAAAGTTATGACTCGTTCCAGCCATCAATCATTAGTCATAAAATTAATGCCCAATATAACT
CTCCTCAATAACTGCACGAGGGTAGAGATTGCAGAATACAGGAGACTACTAAGAACAGTTTTG
GAACCAATTAGGGATGCACTTAATGCAATGACCCAGAACATAAGGCCGGTTCAGAGCGTAGCT
TCAAGTAGGAGACACAAGAGATTTGCGGGAGTAGTCCTGGCAGGTGCGGCCCTAGGTGTTGCC
ACAGCTGCTCAGATAACAGCCGGCATTGCACTTCACCGGTCCATGCTGAACTCTCAGGCCATC
GACAATCTGAGAGCGAGCCTGGAAACTACTAATCAGGCAATTGAGGCAATCAGACAAGCAGGG
CAGGAGATGATATTGGCTGTTCAGGGTGTCCAAGACTACATCAATAATGAGCTGATACCGTCT
ATGAACCAGCTATCTTGTGATCTAATCGGTCAGAAGCTCGGGCTCAAATTGCTTAGATACTAT
ACAGAAATCCTGTCATTATTTGGCCCCAGCCTACGGGACCCCATATCTGCGGAGATATCTATC
CAGGCTTTGAGTTATGCACTTGGAGGAGATATCAATAAGGTGTTAGAAAAGCTCGGATACAGT
GGAGGCGATTTACTAGGCATCTTAGAGAGCAGAGGAATAAAGGCTCGGATAACTCACGTCGAC
ACAGAGTCCTACTTCATAGTCCTCAGTATAGCCTATCCGACGCTGTCCGAGATTAAGGGGGTG
ATTGTCCACCGGCTAGAGGGGGTCTCGTACAACATAGGCTCTCAAGAGTGGTATACCACTGTG
CCCAAGTATGTTGCAACCCAAGGGTACCTTATCTCGAATTTTGATGAGTCATCATGTACTTTC
ATGCCAGAGGGGACTGTGTGCAGCCAAAATGCCTTGTACCCGATGAGTCCTCTGCTCCAAGAA
TGCCTCCGGGGGTCCACCAAGTCCTGTGCTCGTACACTCGTATCCGGGTCTTTTGGGAACCGG
TTCATTTTATCACAAGGGAACCTAATAGCCAATTGTGCATCAATTCTTTGTAAGTGTTACACA
ACAGGTACGATTATTAATCAAGACCCTGACAAGATCCTAACATACATTGCTGCCGATCGCTGC
CCGGTAGTCGAGGTGAACGGCGTGACCATCCAAGTCGGGAGCAGGAGGTATCCAGACGCTGTG
TACTTGCACAGAATTGACCTCGGTCCTCCCATATCATTGGAGAGGTTGGACGTAGGGACAAAT
CTGGGGAATGCAATTGCCAAATTGGAGGATGCCAAGGAATTGTTGGAATCATCGGACCAGATA
TTGAGAAGTATGAAAGGTTTATCGAGCACTAGCATAGTCTACATCCTGATTGCAGTGTGTCTT
GGAGGGTTGATAGGGATCCCCACTTTAATATGTTGCTGCAGGGGCGTTGTAACAAAAGGGA
GAACAAGTTGGTATGTCAAGACCAGGCCTAAAGCCTGACCTTACAGGAACATCAAAATCCTAT
GTAAGATCGCTTTGA
```

FIG. 6 (cont.)

SEQ ID NO:6
MHNKNPKKSKPLPHTRQDPLQQHSTRSAETKTSQGQHSTTSAQRSTYHGPRTSDRSVHYIMNR
TRSCKQTSHRSDNIPPHRDHEGIIHHTPESVTQGASSWFKRRQSNATNAGSQYTWLVLWCIGI
ASLLLCSKAQIHWNNLSTIGIIGTDSVHYKIMTRPSHQYLVIKLMPNVSLIDNCTKAELGEYE
KLLNSVLEPINQALTLMTNNVKPLQSVGSGRRQRRFAGVVLAGAALGVATAAQITAGIALHQS
NLNAQAIQSLRTSLEQSNKAIEEIREATQETVIAVQGVQDYVNNELVPAMQHMSCELVGQRLG
LKLLRYYTELLSIFGPSLRDPISAEISIQALSYALGGEIHKILEKLGYSGNDMIAILESRGIK
TKITHVDLPGKLIILSISYPTLSEVKGVIVHRLEAVSYNIGSQEWYTTVPKYVATNGYLISNF
DESSCVFVSESAICSQNSLYPMSPILQQCIRGDTSSCARTLVSGTMGNKFILSKGNIVANCAS
ILCKCYSTSTIINQSPDKLLTFIASDTCPLVEIDGVTIQVGGRQYPDMVYESKVALGPAISLE
RLDVGTNLGNALKKLDDAKVLIDSSNQILETVKRSSFNFGSLLSVPILICTALALLLLIYCCK
RRYRQTFKHNTKVDPTFKPDLTGTSKSYVRSL

SEQ ID NO:7
MHNKIPKRSKPLPHTRQDPLQQHSTRFGETTTSQGRHSTTSAQRSTHHGPRTSDRPVHHTMNR
TRSCKQTSHRSDNILPHRDHKGIIHHTPESVTQGASSWFKRRQFNATNAGSQCTWLVLWCIGI
ASLFLCSKAQIHWNNLSTIGIIGTDSVHYKIMTRPSHQYLVIKLMPNVSLIDNCTKAELGEYE
KLLNSVLEPINQALTLMTNNVKPLQSVGSGRRQRRFAGVVLAGAALGVATAAQITAGIALHQS
NLNAQAIQSLRTSLEQSNKAIEEIREATQETVIAVQGVQDYVNNELVPAMQHMSCELVGQRLG
LKLLRYYTELLSIFGPSLRDPISAEISIQALSYALGGEIHKILEKLGYSGNDMIAILESRGIK
TKITHVDLPGKLIILSISYPTLSEVKGVIVHRLETVSYNIGSQEWYTTVPKYVATNGYLISNF
DESSCVFFSESAICSQNSLYPMSPILQQCIRGDTSSCARTLVSGTMGNKFILSKGNIVANCAS
ILCKCYSTSTIINQSPDKLLTFIASDTCPLVEIDGVTIQVGGRQYPDMVYESKVALGPAISLE
RLDVGTNLGNALKKLDDAKVLIDSSNQILETVKRSSFNFGSLLSIPILICTALVLLLLIYCCN
RRYRQTFKHNTKVDPTFKPDLTGTSKSYVRSL

SEQ ID NO:8
MLPYQDKVGAFYKDNARANSTKLSLVTEGHGGRRPPYLLFVLLILLVGILALLAITGVRFHQV
STSNMEFSRLLKEDMEKSEAVHHQVIDVLTPLFKIIGDEIGLRLPQKLNEIKQFILQKTNFFN
PNREFDFRDLHWCINPPSTVKVNFTNYCESIGIRKAIASAANPILLSALSGGRGDIFPPHRCS
GATTSVGKVFPLSVSLSMSLISRTSEVINMLTAISDGVYGKTYLLVPDDIEREFDTREIRVFE
IGFIKRWLNDMPLLQTTNYMVLPKNSKAKVCTIAVGELTLASLCVEESTVLLYHDSSGSQDGI
LVVTLGIFWATPMDHIEEVIPVAHPSMKKIHITNHRGFIKDSIATWMVPALASEKQEEQKGCL
ESACQRKTYPMCNQASWEPFGGRQLPSYGRLTLPLDASVDLQLNISFTYGPVILNGDGMDYYE
SPLLNSGWLTIPPKDGTISGLINKAGRGDQFTVLPHVLTFAPRESSGNCYLPIQTSQIRDRDV
LIESNIVVLPTQSIRYVIATYDISRSDHAIVYYVDPIRTISYTHPFRLTTKGRPDFLRIECF
VWDDNLWCHQFYRFEADIANSTTSVENLVRIRFSCNR

FIG. 6 (cont.)

```
SEQ ID NO:9
MSPQRDRINAFYKDNPHSKGSRIVINREHLMIDRPYVLLAVLFVMFLSLIGLLAIAGI
RLHRAAIYTAEIHKSLSTNLDVTNSIEHQVKDVLTPLFKIIGDEVGLRTPQRFTDLVK
FISDKIKFLNPDREYDFRDLTWCINPPERIKLNYDQYCADVAAEELMNALVNSTLLET
RTTNQFLAVSKGNCSGPTTIRGQFSNMSLSLLDLYLSRGYNVSSIVTMTSQGMYGGTY
LVEKPNLNSKGSELSQLSMYRVFEVGVIRNPGLGAPVFHMTNYFEQPISKDLSNCMVA
LGELKLAALCHGGDSITIPYQGSGKGVSFQLVKLGVWKSPTDMHSWVPLSTDDPVIDR
LYLSSHRGVITDNQANWAVPTTRTDDKLRMETCFQQACKGKIQALCENLEWAPLKDSR
IPSYGVLSVDLSLAAEPKIKIASGFGPLITHGSGMDLYKSNHNNVYWLTIPPMKNLAL
GVINTLEWIPRLKVSPNLFTVPIKEAGEDCHAPTYLPAEVDGDVKLSSNLVILPGQDL
QYVLATYDTSRVEHAVVYYVYSPSRSFSYFYPFRLPIKGTPIELQVECFTWAQRLWCR
HFCVLADSESGGHLTHSGMVGMEVSCTVNREDEANRR
```

MODIFIED VIRUSES

CROSS-REFERENCE TO RELATED APPLICATIONS

This application is a National Stage application under 35 U.S.C. § 371 of International Application No. PCT/US2018/026079, having an International Filing Date of Apr. 4, 2018, which claims priority to U.S. application Ser. No. 62/506,892, filed on May 16, 2017. The disclosures of the prior applications are considered part of the disclosure of this application, and are incorporated in their entirety into this application.

BACKGROUND

1. Technical Field

This document relates to methods and materials for making and using viruses (e.g., measles viruses or adenoviruses) having a reduced susceptibility to antibody neutralization (e.g., antibody neutralization by serum from measles virus vaccines).

2. Background Information

Measles virus (MV) causes many deaths each year, mostly amongst children under the age of five. Unvaccinated children are at highest risk of measles and measles related deaths. In particular, infants whose maternal anti-measles antibody titers have waned to non-protective levels, but are still too young to receive the current measles vaccine recommended for infants at 9-12 months, can be at an elevated risk of measles and measles related deaths.

In addition, Edmonston lineage MVs have proven to be potentially potent anticancer drugs when administered to measles seronegative cancer patients. However, upwards of 90% of cancer patients in most countries have protective titers of anti-measles antibodies in their blood (e.g., due to natural measles infection or measles vaccination). Measles-immune human serum negates the therapeutic efficacy of systemically administered oncolytic MVs in tumor-bearing mice by neutralizing the virus before it reaches its target (the tumor cells). Hence, the majority of cancer patients are unable to benefit from systemically administered oncolytic MV therapy.

SUMMARY

This document provides methods and materials for making and using viruses (e.g., MVs) having a reduced susceptibility to antibody neutralization (e.g., antibody neutralization by monoclonal anti-MV antibodies and/or serum from MV vaccines). For example, this document provides recombinant morbilliviruses (e.g., recombinant MVs) having a reduced ability of being recognized by anti-MV antibodies that were generated against a wild-type MV or a pre-existing MV vaccine as compared to a wild-type MV H and F polypeptides or the H and F polypeptides of a pre-existing MV vaccine.

As demonstrated herein, a recombinant MV with a substituted H gene (e.g., encoding a multiply mutated measles H protein from which several immunodominant epitopes have been eliminated) and a substituted F gene (e.g., a canine distemper virus F gene encoding a canine distemper virus F protein) is resistant to neutralization by human measles-immune human serum. A recombinant MV described herein can be used to address the major limitations of currently available measles vaccines, MV-based platform vaccines, and oncolytic MVs, namely their susceptibility to neutralization by measles-immune human serum.

In one aspect, this document features a virus having a nucleic acid encoding a measles virus H polypeptide comprising at least 6 amino acid substitutions and a nucleic acid encoding a morbillivirus F polypeptide other than a measles virus F polypeptide. The virus can be a measles virus. The virus can be a viral vector (e.g., vector derived from an adenovirus, an adeno-associated virus, a retrovirus, a lentivirus, a herpes virus, a vaccinia virus, or a rhabdovirus). The measles virus H polypeptide can include SEQ ID NO:9 having 6 or more (e.g., 6, 7, 8, 9, 10, 11, 12, 13, 14, 15, 16, 17, 18, or 19) of the following amino acid substitutions: S189P, E235G, N238D, L249P, G302R, Y310C, Q311R, R377Q, M378K, D416N, N481Y, K488E, G491E, H495R, D505T, R533G, S546G, R547G, and F552V. In some cases, the measles virus H polypeptide can include SEQ ID NO:9 having a E471K substitution. For example, the measles virus H polypeptide can include SEQ ID NO:9 having the following amino acid substitutions: S189P, E235G, N238D, L249P, G302R, Y310C, Q311R, R377Q, M378K, D416N, E471K, N481Y, K488E, G491E, H495R, D505T, R533G, S546G, R547G, and F552V. In some cases, the measles virus H polypeptide can include SEQ ID NO:1 having 6 or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following amino acid substitutions: H17S, D149N, S189P, G211S, E235G, N238D, 5240N, L249P, V280I, N282K, G302R, E303G, Q311R, Q334H, A359T, K364N, R377Q, M378K, P397L, T420A, V421A, L423P, F476L, N481Y, G491D, H495R, D505T, R533G, V562T, D574A, K576R, I594L, G603E, T609N, G613E, and T614A. For example, the said measles virus H polypeptide can include SEQ ID NO:3. In some cases, the measles virus H polypeptide can include SEQ ID NO:1 having a E471K substitution. For example, the measles virus H polypeptide can include SEQ ID NO:1 having 6 or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following amino acid substitutions: H17S, D149N, S189P, G211S, E235G, N238D, 5240N, L249P, V280I, N282K, G302R, E303G, Q311R, Q334H, A359T, K364N, R377Q, M378K, P397L, T420A, V421A, L423P, E471P, F476L, N481Y, G491D, H495R, D505T, R533G, V562T, D574A, K576R, I594L, G603E, T609N, G613E, and T614A. The measles virus F polypeptide can be a canine distemper virus F polypeptide. The virus can exhibit CD46-dependent cell entry. The virus can exhibit reduced (or no) Nectin-4-dependent cell entry relative to a wild type virus. The virus can lack the measles virus F polypeptide, can lack nucleic acid encoding the measles virus F polypeptide, or can lack both the measles virus F polypeptide and the nucleic acid encoding the measles virus F polypeptide. The virus can lack the wild-type measles virus H polypeptide, can lack nucleic acid encoding the wild-type measles virus H polypeptide, or can lack both the wild-type measles virus H polypeptide and the nucleic acid encoding the wild-type measles virus H polypeptide.

In another aspect, this document features a method for reducing the number of viable tumor cells in a mammal. The method includes, or consists essentially of, administering to the mammal a virus having a nucleic acid encoding a measles virus H polypeptide comprising at least 17 amino acid substitutions and a nucleic acid encoding a morbillivirus F polypeptide other than a measles virus F polypeptide.

The virus can be a measles virus. The virus can be viral vector (e.g., vector derived from an adenovirus, an adeno-associated virus, a retrovirus, a lentivirus, a herpes virus, a vaccinia virus, or a rhabdovirus). The measles virus H polypeptide can include SEQ ID NO:9 having 6 or more (e.g., 6, 7, 8, 9, 10, 11, 12, 13, 14, 15, 16, 17, 18, or 19) of the following amino acid substitutions: S189P, E235G, N238D, L249P, G302R, Y310C, Q311R, R377Q, M378K, D416N, N481Y, K488E, G491E, H495R, D505T, R533G, S546G, R547G, and F552V. In some cases, the measles virus H polypeptide can include SEQ ID NO:9 having a E471K substitution. For example, the measles virus H polypeptide can include SEQ ID NO:9 having the following amino acid substitutions: S189P, E235G, N238D, L249P, G302R, Y310C, Q311R, R377Q, M378K, D416N, E471K, N481Y, K488E, G491E, H495R, D505T, R533G, S546G, R547G, and F552V. In some cases, the measles virus H polypeptide can include SEQ ID NO:1 having 6 or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following amino acid substitutions: H17S, D149N, S189P, G211S, E235G, N238D, S240N, L249P, V280I, N282K, G302R, E303G, Q311R, Q334H, A359T, K364N, R377Q, M378K, P397L, T420A, V421A, L423P, F476L, N481Y, G491D, H495R, D505T, R533G, V562T, D574A, K576R, I594L, G603E, T609N, G613E, and T614A. For example, the said measles virus H polypeptide can include SEQ ID NO:3. In some cases, the measles virus H polypeptide can include SEQ ID NO:1 having a E471K substitution. For example, the measles virus H polypeptide can include SEQ ID NO:1 having 6 or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following amino acid substitutions: H17S, D149N, S189P, G211S, E235G, N238D, S240N, L249P, V280I, N282K, G302R, E303G, Q311R, Q334H, A359T, K364N, R377Q, M378K, P397L, T420A, V421A, L423P, E471K, F476L, N481Y, G491D, H495R, D505T, R533G, V562T, D574A, K576R, I594L, G603E, T609N, G613E, and T614A. The measles virus F polypeptide can be a canine distemper virus F polypeptide. The virus can exhibit CD46-dependent cell entry. The virus can exhibit reduced (or no) Nectin-4-dependent cell entry relative to a wild type virus. The mammal can be a human.

In another aspect, this document features a method for stimulating an immune response against measles virus in a mammal. The method includes, or consists essentially of, administering to the mammal a virus having a nucleic acid encoding a measles virus H polypeptide comprising at least 17 amino acid substitutions and a nucleic acid encoding a morbillivirus F polypeptide other than a measles virus F polypeptide. The virus can be a measles virus. The virus can be viral vector (e.g., vector derived from an adenovirus, an adeno-associated virus, a retrovirus, a lentivirus, a herpes virus, a vaccinia virus, or a rhabdovirus). The measles virus H polypeptide can include SEQ ID NO:9 having 6 or more (e.g., 6, 7, 8, 9, 10, 11, 12, 13, 14, 15, 16, 17, 18, or 19) of the following amino acid substitutions: S189P, E235G, N238D, L249P, G302R, Y310C, Q311R, R377Q, M378K, D416N, N481Y, K488E, G491E, H495R, D505T, R533G, S546G, R547G, and F552V. In some cases, the measles virus H polypeptide can include SEQ ID NO:9 having a E471K substitution. For example, the measles virus H polypeptide can include SEQ ID NO:9 having the following amino acid substitutions: S189P, E235G, N238D, L249P, G302R, Y310C, Q311R, R377Q, M378K, D416N, E471K, N481Y, K488E, G491E, H495R, D505T, R533G, S546G, R547G, and F552V. In some cases, the measles virus H polypeptide can include SEQ ID NO:1 having 6 or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following amino acid substitutions: H17S, D149N, S189P, G211S, E235G, N238D, S240N, L249P, V280I, N282K, G302R, E303G, Q311R, Q334H, A359T, K364N, R377Q, M378K, P397L, T420A, V421A, L423P, F476L, N481Y, G491D, H495R, D505T, R533G, V562T, D574A, K576R, I594L, G603E, T609N, G613E, and T614A. For example, the said measles virus H polypeptide can include SEQ ID NO:3. In some cases, the measles virus H polypeptide can include SEQ ID NO:1 having a E471K substitution. For example, the measles virus H polypeptide can include SEQ ID NO:1 having 6 or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following amino acid substitutions: H17S, D149N, S189P, G211S, E235G, N238D, S240N, L249P, V280I, N282K, G302R, E303G, Q311R, Q334H, A359T, K364N, R377Q, M378K, P397L, T420A, V421A, L423P, E471K, F476L, N481Y, G491D, H495R, D505T, R533G, V562T, D574A, K576R, I594L, G603E, T609N, G613E, and T614A. The measles virus F polypeptide can be a canine distemper virus F polypeptide. The virus can exhibit CD46-dependent cell entry. The virus can exhibit reduced (or no) Nectin-4-dependent cell entry relative to a wild type virus. The mammal can be an infant (e.g., a human infant). The human infant can have transplacentally acquired anti-measles antibodies.

In another aspect, this document features a nucleic acid construct comprising (or consisting essentially of, or consisting of) a nucleic acid encoding a measles virus H polypeptide comprising at least six amino acid substitutions as compared to a wild-type measles virus H polypeptide, and a nucleic acid encoding a morbillivirus F polypeptide other than a measles virus F polypeptide. The measles virus H polypeptide can comprise SEQ ID NO:9 having six or more of the following amino acid substitutions: S189P, E235G, N238D, L249P, G302R, Y310C, Q311R, R377Q, M378K, D416N, N481Y, K488E, G491E, H495R, D505T, R533G, S546G, R547G, and F552V. The measles virus H polypeptide can comprise SEQ ID NO:9 having the following amino acid substitutions: S189P, E235G, N238D, L249P, G302R, Y310C, Q311R, R377Q, M378K, D416N, N481Y, K488E, G491E, H495R, D505T, R533G, S546G, R547G, and F552V. The measles virus H polypeptide can comprise at least one amino acid substitution within each of the antigenic sites set forth in Table 1. The wild-type measles virus H polypeptide can be a wild-type measles virus H polypeptide of the MVi/Madrid.SPA/50.10 strain. The wild-type measles virus H polypeptide can comprise the amino acid sequence set forth in SEQ ID NO:9. The measles virus H polypeptide can comprise SEQ ID NO:3. The morbillivirus F polypeptide can be a canine distemper virus F polypeptide. The nucleic acid construct can be a viral vector. The viral vector can be derived from a virus selected from the group consisting of an adenovirus, an adeno-associated virus, a retrovirus, a lentivirus, a herpes virus, a vaccinia virus, and a rhabdovirus. The measles virus H polypeptide can comprise at least one amino acid substitution within each of the antigenic sites set forth in Table 2. The measles virus H polypeptide can comprise a substitution at position E471 as compared to the wild-type measles virus H polypeptide. The substitution at position E471 can be a E471K substitution. The measles virus H polypeptide can comprise SEQ ID NO:9 having the following amino acid substitutions: S189P, E235G, N238D, L249P, G302R, Y310C, Q311R, R377Q, M378K, D416N, E471K, N481Y, K488E, G491E, H495R, D505T, R533G, S546G, R547G, and F552V. The nucleic acid construct can be a construct that does not encode the measles virus F polypeptide. The nucleic acid construct can be a construct that does not encode the wild-type measles virus H polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4 depicts the tropism and fusion capacity for a mutated MV H polypeptide in conjunction with a CDV F polypeptide.

FIG. 6 shows a naturally occurring MV H polypeptide (SEQ ID NO:1), a nucleic acid encoding a naturally occurring MV H polypeptide (SEQ ID NO:2), a modified H polypeptide (SEQ ID NO:3), a naturally occurring MV F polypeptide (SEQ ID NO:4), a nucleic acid encoding a naturally occurring MV F polypeptide (SEQ ID NO:5), CDV F polypeptides (SEQ ID NOs: 6 and 7), a CDV H polypeptide (SEQ ID NO:8), and a naturally occurring MV H polypeptide of MVi/Madrid.SPA/50.10[H1] (SEQ ID NO:9).

FIGS. 14A-D. Characterization of recombinant MeVs. (A) Replication kinetics of recombinant viruses. Vero/hSLAM were infected with the indicated virus at MOI of 0.03. At the indicated time, GFP autofluorescence and bright-field images were recorded and overlayed. Magnification, ×40. Afterwards, cells were collected in the culture medium, and virus titer was determined on Vero/hSLAM as FFU/mL. A, H1, and Δ8 denotes MeV expressing the equivalent MeV-H genes and vaccine MeV-F, whilst Stealth virus is a virus encoding MeV-HΔ8 together with CDV-F. (B) Protein incorporation into virions. $10^4$ virus particles were electrophoresed under reducing conditions and immunoblotted with the relevant antibody. Note that anti-MeV-F antibody does not cross-react with CDV-F. (C) Left panel. PRMN $NT_{50}$ values of measles immune human sera against the MeV A (vaccine) and Stealth viruses. Each line represents a single individual (N=14). Dotted line indicated the antibody levels threshold for protection against clinical disease. Ferret serum anti-CDV was used as a control. ***, $P<0.001$ as determined by Wilcoxon matched-pairs signed rank test. Right panel, correlation between $NT_{50}$ for the vaccine virus and Stealth. $NT_{50}$ values are plotted on a $log_2$ scale. $P<0.001$, in both Pearson and Spearman correlation test. Dotted lines indicated the 95% confidence interval for the regression analysis. R=0.51. (D) PRMN of guinea Pig polyclonal MeV antiserum against A and Stealth viruses. Non-linear regression was performed to calculate the $NT_{50}$ values, which were transformed to mIU/mL (3584 for A virus and 563 for Stealth).

FIG. 18. ELISA method for determination of receptor binding to MeV-H. Precoated microwells with Strep-tactin XT were incubated with supernatant containing MeV-H, followed by incubation with either anti-FLAG antibody (control) or single receptor-Fc. Binding was revealed by HRP-conjugated anti-IgG and monitored by optical density.

DETAILED DESCRIPTION

Figure 1:
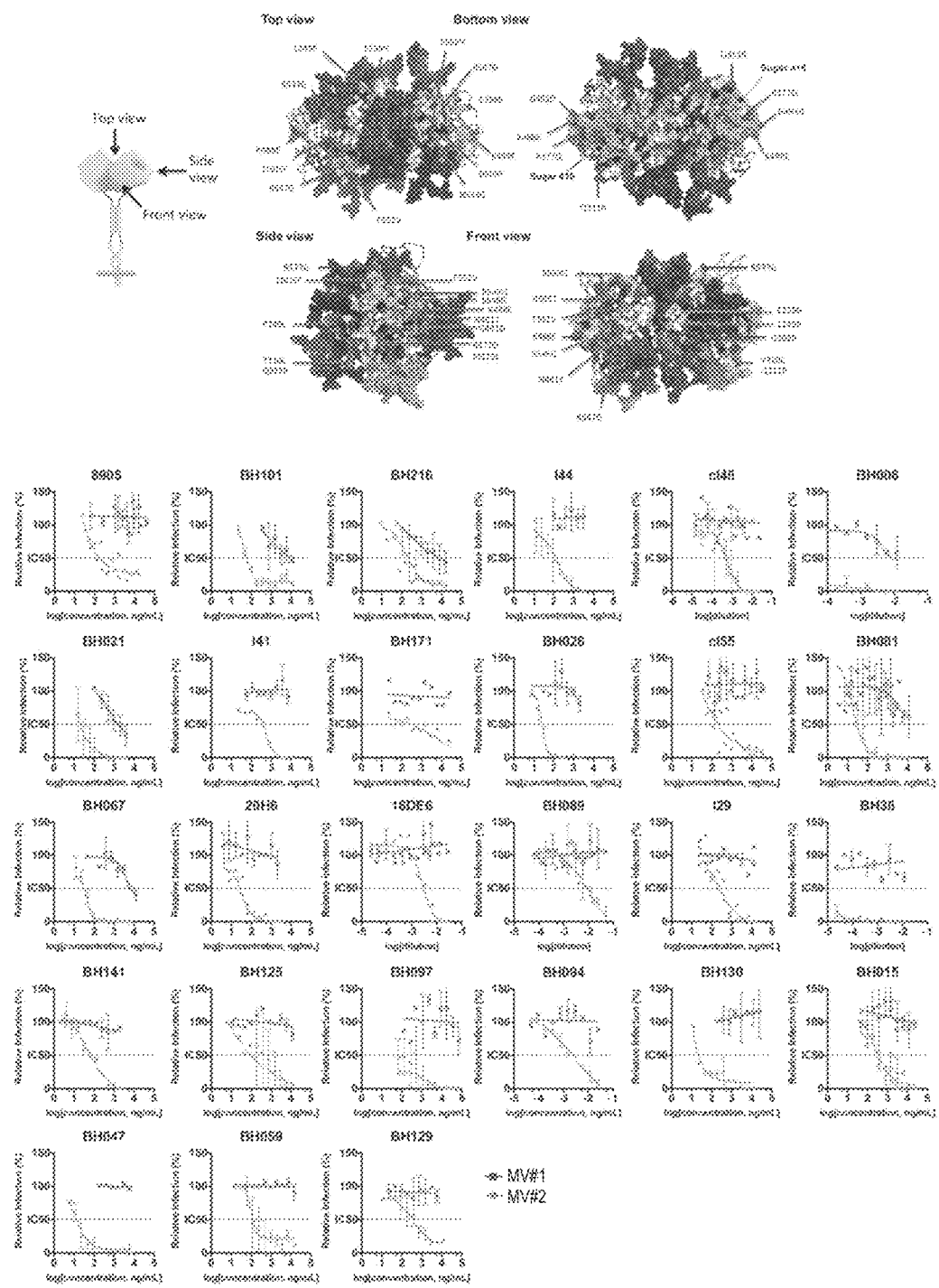
FIG. 1 presents mutations encoded in the MV-H polypeptide to escape neutralization.

This document provides nucleic acids, polypeptides, and viruses containing the nucleic acids and/or polypeptides. This document also provides methods for using the viruses to treat cancer patients or to vaccinate infants to help protect them from MV infections. For example, this document provides MV hemagglutinin (H) polypeptides, nucleic acids encoding MV H polypeptides, CDV F polypeptides, nucleic acid sequences encoding CDV F polypeptides, and viruses containing such nucleic acids and/or polypeptides. For example, this document provides a recombinant virus (e.g., a MV or an adenovirus (Ad)) containing a nucleic acid encoding a modified H polypeptide and a nucleic acid encoding a modified F polypeptide. Such a recombinant virus can exhibit reduced susceptibility to antibody neutralization, reduced ability to trigger membrane fusion, and/or diminished replicative fitness. A recombinant virus described herein can propagate in cells (e.g., human cells such as Vero cells and HeLa cells) as efficiently as a wild type virus. The viruses described herein can be used to treat cancer patients or to vaccinate infants in a manner such that the viruses exhibit a reduced susceptibility to antibody neutralization. In some cases, a recombinant virus described herein can be used to treat cancer in patients who have pre-existing measles immunity. In some cases, a recombinant virus described herein can be used to vaccinate children having neutralizing anti-measles antibodies (e.g., transplacentally acquired neutralizing anti-measles antibodies).

This document provides H polypeptides, F polypeptides, and nucleic acids that encode them that are heterologous to naturally occurring H and F polypeptides.

The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

An "isolated nucleic acid" refers to a nucleic acid that is separated from other nucleic acids that are present in a viral genome, including nucleic acids that normally flank one or both sides of the nucleic acid in a viral genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a nucleic acid construct (e.g., a vector such as an expression vector, an autonomously replicating plasmid, or a virus (e.g., a paramyxovirus, retrovirus, lentivirus, Ad, herpes virus, adenovirus, parvovirus such as an Ad-associated virus, rhabdovirus such as vesicular stomatitis virus, or vaccinia virus), or into the genomic DNA of a prokaryote or eukaryote. In cases where an isolated nucleic acid is a virus, the virus can be, for example, an oncolytic virus or a viral vector (e.g., a viral gene transfer vector). For example, a viral vector can be a vector derived from an Ad, an Ad-associated virus, a retrovirus, a lentivirus, a herpes virus, a vaccinia virus, or a rhabdovirus. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

As used here, a "polypeptide" refers to a chain of amino acid residues, regardless of post-translational modification (e.g., phosphorylation or glycosylation).

A nucleic acid encoding a modified H polypeptide provided herein can encode a MV H polypeptide that is heterologous to naturally occurring MV H polypeptides or to the H polypeptide having the amino acid sequence set forth in GenBank Accession No. AAF85673 (Version AAF85673.1, GI No. 9181880; SEQ ID NO:1). Additional examples of naturally occurring MV H polypeptides (and the nucleic acid sequences encoding them) can be found in public databases. For example, GenBank Accession No. KP191044 (Version KP191044.1, GI No. 727347518; SEQ ID NO:2) provides an example of a nucleic acid sequence encoding a wild type H polypeptide. In some cases, a MV H polypeptide designed to be heterologous to naturally occurring MV H polypeptides and/or heterologous to the H polypeptide having the amino acid sequence set forth in SEQ ID NO:1 can be referred to as a modified H polypeptide. The term "H polypeptide amino acid sequence" as used herein refers to an amino acid sequence that is at least 85 percent (e.g., at least 85, 90, 95, 99, or 100 percent) identical to the sequence set forth in SEQ ID NO:1. In some cases, a modified H polypeptide can have at least 6 (e.g., 6, 7, 8, 9, 10, 11, 12, 13, 14, 15, 16, 17, 18, 19, 20, 21, 22, 23, 24, 25, or more) amino acid residues associated with immunodominant epitopes of the MV H glycoprotein that have been modified (e.g., substituted). Amino acid substitutions in H polypeptides typically are located at positions involved in the binding of H polypeptides to its receptors.

In some cases, a modified H polypeptide can have one or more amino acid substitutions in, for example, each of the 6 antigenic sites set forth in Table 1.

TABLE 1

Antigenic sites of H polypeptides.

| Site | Name | Start Position | Stop Position |
|---|---|---|---|
| 1 | Ia, V, VI, E4, 1, LE | 307 | 318 |
| 2 | Ib, NE, IV | 233 | 250 |
| 3 | IIa, SSE, VII, 2 | 487 | 495 |
| 4 | IIb, SSE, VII, 2 | 471 | 477 |
| 5 | III, VII, E2, IIIB, 3, 4, RBE | 530 | 562 |
| 6 | 'Noose', HNE, I, E3, D, D/E | 377 | 405 |

In some cases, a modified H polypeptide can have one or more amino acid substitutions in, for example, 7 of the 8 antigenic sites set forth in Table 2 or each of the 8 antigenic sites set forth in Table 2.

TABLE 2

Antigenic sites of H polypeptides.

| Site | Name | Start Position | Stop Position |
|---|---|---|---|
| 1 | E1, φ | 280 | 285 |
| 2 | Ia, V, VI, E4, 1, LE | 307 | 318 |
| 3 | Ib, NE, IV | 233 | 250 |
| 4 | IIa, SSE, VII, 2 | 487 | 495 |
| 5 | IIb, SSE, VII, 2 | 471 | 477 |
| 6 | III, IIIA, VII, E2, IIIB, 3, 4, RBE | 530 | 562 |
| 7 | 'Noose', HNE, I, E3, D, D/E | 377 | 405 |
| 8 | V | 450 | 456 |
|   |   | 464 | 470 |
|   |   | 478 | 484 |

In some cases, a modified H polypeptide can have 6 or more (e.g., 6, 7, 8, 9, 10, 11, 12, 13, 14, 15, 16, 17, 18, 19, 20, 21, 22, 23, 24, 25, or more) amino acid substitutions in, for example, positions corresponding to amino acids D149, A158, T174, T176, T177, F180, L181, S189, R195, N200, R211, R212, V220, E235, S240, G243, L246, L249, H252, V259, F276, V280, D283, S285, L296, G302, E303, S305, P308, Q311, S316, S318, M333, Q334, P338, L339, V345, I346, L351, V357, A359, K364, V367, R377, M378, F382, A392, C394, P397, V412, T420, V421, L423, K424, H448, V450, K460, E471, I473, F476, K477, N481, G491, E/G492, H495, D505, L517, R533, I559, V562, I564, D574, Q575, K576, A587, G603, V608, T609, E611, G613, T614, R616, and/or R617 of a full-length H polypeptide having the amino acid sequence set forth in SEQ ID NO:1. For example, a modified H polypeptide provided herein can have the amino acid sequence set forth in SEQ ID NO:1 with the exception that the MV H polypeptide has 6 or more (e.g., 6, 7, 8, 9, 10, 11, 12, 13, 14, 15, 16, 17, 18, 19, 20, 21, 22, 23, 24, 25, or more) of the following amino acid substitutions: H17S, D149N, S189P, G211S, E235G N238D, 5240N, L249P, L276G, V280I, G302R, E303G, Q311R, Q334H, A359T, K364N, R377Q, M378K, P397L, T420A, V421A, L423P, E471K, F476L, N481Y, G491D, H495R, D505T, R533G, I594L, V562T, D574A, K576R, G603E, T609N, G613E, and T614A.

In some cases, a modified H polypeptide can have 6 or more (e.g., 6, 7, 8, 9, 10, 11, 12, 13, 14, 15, 16, 17, 18, or 19) amino acid substitutions in, for example, positions corresponding to amino acids S189, E235, N238, L249, G302, Y310, Q311, R377, M378, D416, E471, N481, K488, G491, H495, D505, R533, S546, R547, and/or F552 of a full-length H polypeptide having the amino acid sequence set forth in SEQ ID NO:9. For example, a modified H polypeptide provided herein can have the amino acid sequence set forth in SEQ ID NO:9 with the exception that the MV H polypeptide has 6 or more (e.g., 6, 7, 8, 9, 10, 11, 12, 13, 14, 15, 16, 17, 18, or 19) of the following amino acid substitutions: S189, E235, N238, L249, G302, Y310, Q311, R377, M378, D416, N481, K488, G491, H495, D505, R533, S546, R547, and F552. In some cases, a modified H polypeptide provided herein can have the amino acid sequence set forth in SEQ ID NO:9 with the exception that the MV H polypeptide has 6 or more (e.g., 6, 7, 8, 9, 10, 11, 12, 13, 14, 15, 16, 17, 18, 19, or 20) of the following amino acid substitutions: S189, E235, N238, L249, G302, Y310, Q311, R377, M378, D416, E471, N481, K488, G491, H495, D505, R533, S546, R547, and F552.

In some cases, a modified H polypeptide provided herein can include one or more other amino acid modifications such as those described elsewhere (see, e.g., WO 2014/015242, Hu et al. (*Virology*, 192(1):351-4 (1993)); Hummel and Bellini (*J. Virol.*, 69(3):1913-16 (1995)); Rima et al. (*J. Gen. Virol.*, 78:97-106 (1997)); Li and Qi (*Arch. Virol.*, 147(4): 775-86 (2002)); Santibanez et al. (*J. Gen. Virol.*, 86:365-74 (2005); and Tahara et al. (*J. Virol.*, 82(9):4630-7 (2008)). For example, a modified H polypeptide provided herein also can include one or more of the following amino acid substitutions: N238D, N282K, Y310C, N405S, D416N, K488E, S546G, R547G, and F552V. In some cases, a modified H polypeptide provided herein also can include one or more of the following amino acid substitutions: N238D, N282K, Y310C, N405S, D416N, E471K, K488E, S546G, R547G, and F552V. As another example, a modified H polypeptide provided herein can include SEQ ID NO:9 having an amino acid substitution at 6 or more (e.g., 6, 7, 8, 9, 10, 11, 12, 13, 14, 15, 16, 17, 18, or 19) of the following positions: S189, E235, N238, L249, G302, Y310, Q311, R377, M378, D416, N481, K488, G491, H495, D505, R533, S546, R547, and F552. For example, a modified H polypeptide provided herein can include SEQ ID NO:9 having 6 or more (e.g., 6, 7, 8, 9, 10, 11, 12, 13, 14, 15, 16, 17, 18, or 19) of the following amino acid substitutions: S189P, E235G, N238D, L249P, G302R, Y310C, Q311R, R377Q, M378K, D416N, N481Y, K488E, G491E, H495R, D505T, R533G, S546G, R547G, and F552V. As another example, a modified H polypeptide provided herein can include SEQ ID NO:9 having an amino acid substitution at 6 or more (e.g., 6, 7, 8, 9, 10, 11, 12, 13, 14, 15, 16, 17, 18, 19, or 20) of the following positions: S189, E235, N238, L249, G302, Y310, Q311, R377, M378, D416, E471, N481, K488, G491, H495, D505, R533, S546, R547, and F552. For example, a modified H polypeptide provided herein can include SEQ ID NO:9 having 6 or more (e.g., 6, 7, 8, 9, 10, 11, 12, 13, 14, 15, 16, 17, 18, 19, or 20) of the following amino acid substitutions: S189P, E235G, N238D, L249P, G302R, Y310C, Q311R, R377Q, M378K, D416N, E471K, N481Y, K488E, G491E, H495R, D505T, R533G, S546G, R547G, and F552V.

Amino acid substitutions can be conservative or non-conservative. Conservative amino acid substitutions replace an amino acid with an amino acid of the same class, whereas non-conservative amino acid substitutions replace an amino acid with an amino acid of a different class. Examples of conservative substitutions include amino acid substitutions within the following groups: (1) glycine and alanine; (2) valine, isoleucine, and leucine; (3) aspartic acid and glutamic acid; (4) asparagine, glutamine, serine, and threonine; (5) lysine, histidine, and arginine; and (6) phenylalanine and tyrosine. In some cases, a modified H polypeptide provided herein can have the amino acid sequence set forth in SEQ ID NO:3. In some cases, a modified MVH polypeptide can be an H polypeptide from another member of the morbillivirus genus (e.g., CDV, CeMV, FeMV, PPRV, PDV, and RPV). For example, a modified MV H polypeptide can be a CDV H polypeptide (e.g., a polypeptide having the sequence set forth in GenBank Accession No. AAC26995 (Version AAC26995.1; SEQ ID NO:8).

A nucleic acid encoding a modified F polypeptide provided herein can encode an F polypeptide that is heterologous to naturally occurring MV F polypeptides or to the F polypeptide having the amino acid sequence set forth in GenBank Accession No. AAF85672 (Version AAF85672.1, GI No. 9181879; SEQ ID NO:4). Examples of naturally occurring MV F polypeptides (and the nucleic acid sequences encoding them) can be found in public database. For example, GenBank Accession No. KP205324 (Version KP205324.1, GI No. 727347524; SEQ ID NO:5) provides an example of a nucleic acid encoding a wild type F polypeptide. In some cases, a MV F polypeptide designed to be heterologous to naturally occurring MV F polypeptides and/or heterologous to the F polypeptide having the amino acid sequence set forth in SEQ ID NO:4 can be referred to as a modified F polypeptide. The term "F polypeptide amino acid sequence" as used herein refers to an amino acid sequence that is at least 85 percent (e.g., at least 85, 90, 95, 99, or 100 percent) identical to the sequence set forth in SEQ ID NO:4. In some cases, a modified MV F polypeptide can be an F polypeptide from another member of the morbillivirus genus (e.g., CDV, CeMV, FeMV, PPRV, PDV, and RPV). For example, a modified MV F polypeptide can be a CDV F polypeptide (e.g., a polypeptide having the sequence set forth in GenBank Accession No. ABR08390 (Version ABR08390.1, GI No. 148724186; SEQ ID NO:6) or GenBank Accession No. ABR08390 (Version ABO31365.1, GI No. 129770954; SEQ ID NO:7).

This document also provides recombinant viruses (e.g., MVs or Ads) containing a nucleic acid encoding a modified H polypeptide described herein and a nucleic acid encoding a modified F polypeptide described herein. A recombinant virus provided herein can be a chimeric virus. In some cases, a recombinant virus can contain a nucleic acid encoding a modified MV H polypeptide described herein and a nucleic acid encoding a modified MV F polypeptide described herein. In some cases, a recombinant virus can contain a modified MV H polypeptide described herein and a modified MV F polypeptide described herein.

In some cases, a recombinant virus provided herein can be a morbillivirus. Any appropriate morbillivirus can contain a nucleic acid described herein (e.g., a nucleic acid encoding a modified MV H polypeptide and/or a nucleic acid encoding a modified MV F polypeptide). Species in the genus morbillivirus include, without limitation, MV (MV), canine distemper virus (CDV), cetacean morbillivirus (CeMV), feline morbillivirus (FeMV), peste-des-petits-ruminants virus (PPRV), phocine distemper virus (PDV), and rinderpest virus (RPV). In some cases, a morbillivirus provided herein is obtained from a MV. Examples of MV strains include, without limitation, MVi/Madrid.SPA/50.10[H1], Edmonston, and Moraten vaccine.

In some cases, a recombinant virus provided herein can be an Ad. Any appropriate Ad can contain a nucleic acid described herein (e.g., a nucleic acid encoding a modified MV H polypeptide and/or a nucleic acid encoding a modified MV F polypeptide). In humans, species in the family Adenoviridae include, without limitation, species A (AdA), species B (AdB), species C (AdC), species D (AdD), species E (AdE), species F (AdF), or species G (AdG).

A nucleic acid provided herein can be obtained using any appropriate method including, without limitation, common molecular cloning and chemical nucleic acid synthesis techniques. For example, PCR can be used to construct nucleic acids that encode a modified H polypeptide or a modified F polypeptide provided herein. PCR refers to a procedure or technique in which target nucleic acid is amplified in a manner similar to that described in U.S. Pat. No. 4,683,195, and subsequent modifications of the procedure described therein.

A nucleic acid provided herein can be incorporated into viruses by standard techniques. For example, recombinant techniques can be used to insert a nucleic acid encoding a modified H polypeptide or a modified F polypeptide provided herein into an infective viral cDNA. In some cases, a nucleic acid can be exogenous to a viral particle, e.g., an expression vector contained within a cell such that the polypeptide encoded by the nucleic acid is expressed by the cell and then incorporated into a new viral particle (e.g., into the envelope of a new viral particle such as a recombinant virus).

Naturally occurring H polypeptides typically have receptor-binding and hemagglutination activities, and functionally cooperate with viral F polypeptides to induce fusion between target cells. Such fusion can be mediated through interactions between H polypeptides and receptors on target cells (e.g., CD46, SLAM, Nectin-4, desmoglein-2, or sialic acid).

Recombinant viruses (e.g., MVs or Ads) provided herein (e.g., containing a nucleic acid encoding a modified H polypeptide and a nucleic acid encoding a modified F polypeptide) can have reduced (or no) Nectin-4-dependent cell entry as compared to a virus having a naturally occurring H polypeptide and/or a naturally occurring F polypeptide. For example, when a modified H polypeptide and a modified F polypeptide are incorporated into a virus, the level of Nectin-4 dependent cell entry exhibited by the virus can be reduced (or eliminated) relative to the level of Nectin-4-dependent cell entry exhibited by a wild type virus containing a corresponding, naturally occurring H polypeptide. A morbillivirus (e.g., a MV) containing a modified H polypeptide and a modified F polypeptide described herein can exhibit reduced (or no) Nectin-4-dependent entry into cells (e.g., epithelial cells) as compared to the amount of Nectin-4-dependent entry of a non-modified MV-H into cells (e.g., epithelial cells). Cell entry via Nectin-4 can be assessed by standard techniques such as those described herein (see Example 1). Recombinant morbilliviruses provided herein can retain the ability to bind to CD46 and/or SLAM. Viruses containing a nucleic acid encoding a modified H polypeptide and a nucleic acid encoding a modified F polypeptide can therefore exhibit CD46- or SLAM-dependent cell entry, and cells containing such viruses can fuse in a CD46- or SLAM-dependent manner. Cell entry via CD46 and/or SLAM receptors can be assessed by standard techniques such as those described in WO 03/093431. In some cases, a recombinant morbilliviruses provided herein can retain the ability to bind to CD46 and not SLAM. Viruses containing a nucleic acid encoding a modified H polypeptide and a nucleic acid encoding a modified F polypeptide can exhibit CD46-dependent cell entry, and cells containing such viruses can fuse in a CD46-dependent manner.

A virus provided herein can be attenuated. As used herein, the term "attenuated" refers to a virus that is immunologically related to a wild type virus but which is not itself pathogenic. An attenuated MV, for example, does not produce classical measles disease. Attenuated viruses typically are replication-competent, in that they are capable of infecting and replicating in a host cell without additional viral functions supplied by, for example, a helper virus or a plasmid expression construct encoding such additional functions.

Any appropriate method can be used to identify a virus containing a nucleic acid provided herein. Such methods include, without limitation, PCR and nucleic acid hybridization techniques such as Northern and Southern analysis. In some cases, immunohistochemistry and biochemical techniques can be used to determine if a virus contains a particular nucleic acid by detecting the expression of a polypeptide encoded by that particular nucleic acid.

Recombinant viruses (e.g., MVs or Ads) containing a nucleic acid encoding a modified H polypeptide and a nucleic acid encoding a modified F polypeptide provided herein can be used to treat cancer patients. A particular virus can be propagated in host cells in order to increase the available number of copies of that virus, typically by at least 2-fold (e.g., by 5- to 10-fold, by 50- to 100-fold, by 500- to 1,000-fold, or even by as much as 5,000- to 10,000-fold). A virus can be expanded until a desired concentration is obtained in standard cell culture media (e.g., DMEM or RPMI—1640 supplemented with 5-10% fetal bovine serum at 37° C. in 5% $CO_2$). A viral titer typically can be assayed by inoculating cells (e.g., Vero cells) in culture. Virus can be harvested from infected cells by scraping cells from the dishes, subjecting them to freeze/thawing (e.g., approximately two rounds), and centrifuging. The cleared supernatants represent "plaque purified" virus.

Viral stocks can be produced by infection of cell monolayers (e.g., adsorption for about 1.5 hours at 37° C.), followed by scraping of infected cells into a suitable medium (e.g., Opti-MEM; Gibco/Invitrogen, Carlsbad, Calif.) and freeze/thaw lysis. Viral stocks can be aliquoted and frozen, and can be stored at −70° C. to −80° C. at concentrations higher than the therapeutically effective dose. A viral stock can be stored in a stabilizing solution. Stabilizing solutions are known in the art and include, without limitation, sugars (e.g., trehalose, dextrose, glucose), amino acids, glycerol, gelatin, monosodium glutamate, $Ca^2$+, and $Mg^{2+}$.

In some cases, recombinant viruses (e.g., MVs or Ads) containing a nucleic acid encoding a modified H polypeptide and a nucleic acid encoding a modified F polypeptide provided herein can be used to treat cancer (e.g., to reduce tumor size, inhibit tumor growth, or reduce the number of viable tumor cells). As used herein, "reducing the number of viable tumor cells" is meant to encompass (1) slowing the rate of growth of a population of tumor cells such that after a certain period of time, a tumor in a treated individual is smaller than it would have been without treatment; (2) inhibiting the growth of a population of tumor cells completely, such that a tumor stops growing altogether after treatment; and/or (3) reducing the population of tumor cells such that a tumor becomes smaller or even disappears after treatment.

Recombinant viruses (e.g., MVs or Ads) containing a nucleic acid encoding a modified H polypeptide and a nucleic acid encoding a modified F polypeptide provided herein can be administered to a cancer patient by, for example, direct injection into a group of cancer cells (e.g., a tumor) or intravenous delivery to cancer cells. Types of cancer cells susceptible to treatment with viruses include neuronal cells, glial cells, myelomonocytic cells, and the like. The methods provided herein can be used to treat types of cancer that include, but are not limited to, myeloma, melanoma, glioma, lymphoma, and cancers of the lung, brain, stomach, colon, rectum, kidney, prostate, ovary, and breast. An attenuated MV containing a modified H polypeptide and a modified F polypeptide provided herein can be used to treat, for example, a lymphoma (e.g., non-Hodgkin's Lymphoma).

A virus provided herein can be administered to a patient in a biologically compatible solution or a pharmaceutically acceptable delivery vehicle, by administration either directly into a group of cancer cells (e.g., intratumorally) or systemically (e.g., intravenously). Suitable pharmaceutical formulations depend in part upon the use and the route of entry, e.g., transdermal or by injection. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient (e.g., depending upon the size of a tumor), an effective dose can be determined by setting as a lower limit the concentration of virus proven to be safe as a vaccine (e.g., $10^3$ pfu) and escalating to higher doses of up to $10^{12}$ pfu, while monitoring for a reduction in cancer cell growth along with the presence of any deleterious side effects. A therapeutically effective dose typically provides at least a 10% reduction in the number of cancer cells or in tumor size. Escalating dose studies can be used to obtain a desired effect for a given viral treatment (see, e.g., Nies and Spielberg, "Principles of Therapeutics," In Goodman & Gilman's *The Pharmacological Basis of Therapeutics*, eds. Hardman, et al, McGraw-Hill, N Y, 1996, pp 43-62).

Viruses provided herein can be delivered in a dose ranging from, for example, about $10^3$ pfu to about $10^{12}$ pfu (typically $>10^8$ pfu). A therapeutically effective dose can be provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses (using the same or a different modified virus) can be administered by the same route as initially used or by another route. A therapeutically effective dose can be delivered in several discrete doses (e.g., days or weeks apart). In some cases, one to about twelve doses can be provided. In some cases, a therapeutically effective dose of attenuated MV can be delivered by a sustained release formulation.

Viruses provided herein can be administered using a device for providing sustained release. A formulation for sustained release of a virus can include, for example, a polymeric excipient (e.g., a swellable or non-swellable gel, or collagen). A therapeutically effective dose of a virus can be provided within a polymeric excipient, wherein the excipient/virus composition is implanted at a site of cancer cells (e.g., in proximity to or within a tumor). The action of body fluids gradually dissolves the excipient and continuously releases the effective dose of virus over a period of time. In some cases, a sustained release device can contain a series of alternating active and spacer layers. Each active layer of such a device typically contains a dose of virus embedded in excipient, while each spacer layer contains only excipient or low concentrations of virus (i.e., lower than the effective dose). As each successive layer of the device dissolves, pulsed doses of virus are delivered. The size/formulation of the spacer layers determines the time interval between doses and is optimized according to the therapeutic regimen being used.

A virus provided herein can be directly administered. For example, a virus can be injected directly into a tumor (e.g., a lymphoma) that is palpable through the skin. Ultrasound guidance also can be used in such a method. In some cases, direct administration of a virus can be achieved via a catheter line or other medical access device, and can be used in conjunction with an imaging system to localize a group of cancer cells. By this method, an implantable dosing device typically is placed in proximity to a group of cancer cells using a guidewire inserted into the medical access device. An effective dose of a virus also can be directly administered to a group of cancer cells that is visible in an exposed surgical field.

In some cases, viruses provided herein can be delivered systemically. For example, systemic delivery can be achieved intravenously via injection or via an intravenous delivery device designed for administration of multiple doses of a medicament. Such devices include, but are not limited to, winged infusion needles, peripheral intravenous catheters, midline catheters, peripherally inserted central catheters, and surgically placed catheters or ports.

The course of virus therapy can be monitored by evaluating changes in clinical symptoms (known in the art for each particular type of cancer) or by direct monitoring of the size of a group of cancer cells or tumor. A method for using a virus of the invention to treat cancer is considered effective if the cancer cell number, tumor size, tumor specific antigen level, and/or other clinical symptoms are reduced by at least 10 percent following administration of virus. For a solid tumor, for example, the effectiveness of virus treatment can be assessed by measuring the size or weight of the tumor before and after treatment. Tumor size can be measured either directly (e.g., using calipers), or by using imaging techniques (e.g., X-ray, magnetic resonance imaging, or computerized tomography) or from the assessment of non-imaging optical data (e.g., spectral data). For a group of cancer cells (e.g., leukemia cells), the effectiveness of viral treatment can be determined by measuring the absolute number of leukemia cells in the circulation of a patient before and after treatment. The effectiveness of viral treatment also can be assessed by monitoring the levels of a cancer specific antigen. Cancer specific antigens include, for example, carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4.

In some cases, recombinant viruses (e.g., MVs or Ads) containing a nucleic acid encoding a modified H polypeptide and a nucleic acid encoding a modified F polypeptide provided herein can be used to vaccinate humans (e.g., infants less than 9 months of age or infants less than 15 months of age). When vaccinating an infant less than 9 months or 15 months of age using the MVs provided herein as a vaccine, the vaccine can effectively induce a protective immune response against MV infection even though the infant contains maternal anti-MV antibodies. For example, a recombinant MV containing a nucleic acid encoding a modified H polypeptide and a nucleic acid encoding a modified F polypeptide can be used to stimulate an immune response against MV in a human.

Any appropriate patient can be treated using the materials and methods described herein. For example, a cancer patient treated or an infant vaccinated using a recombinant MV described herein can be a mammal (e.g., human, non-human primate, dog, and cat), bird, or reptile.

The invention will be further described in the following examples, which do not limit the scope of the invention described in the claims.

EXAMPLES

Example 1—Recombinant MVs

A measles virus (MV #1) was produced to have a modified H protein (SEQ ID NO:3) having with the following amino acid substitutions (with respect to SEQ ID NO:1): H17S, D149N, S189P, G211S, E235G, N238D, S240N, L249P, L276G, V280I, N282K, G302R, E303G, Y310C, Q311R, Q334H, A359T, K364N, R377Q, M378K, P397L, N405S, D416N, T420A, V421A, L423P, F476L, N481Y, K488E, G491D, H495R, D505T, R533G, S546G, R547G, F552V, V562T, D574A, K576R, I594L, G603E, T609N, G613E, and T614A. This modified H protein (SEQ ID NO:3) was produced by introducing 19 point mutations into the measles virus hemagglutinin protein (SEQ ID NO:9) of the wild-type MVi/Madrid.SPA/50.10 (genotype H1) strain. The 19 point mutations were S189P, E235G, N238D, L249P, G302R, Y310C, Q311R, R377Q, M378K, D416N, N481Y, K488E, G491E, H495R, D505T, R533G, S546G, R547G, and F552V.

A MV vaccine strain (MV #2) and the recombinant MV #1 were incubated for 1 hour at 37° C. with mAb shown in FIG. 1 before infection of Vero/hSLAM cells seeded on a 96 well plate. The number of infected eGFP positive foci were counted in quadruplicate 48 hours post-infection and expressed as percentage of the number of infected EGFP positive foci in absence of nAb. MV #1 avoided neutralizing antibodies targeting multiple antigenic sites. H protein modifications that contributed to MV #1 escaping neutralization are shown in FIG. 1.

To determine the resistance of MV #1 to human anti-measles antiserum, MV glycoprotein-specific antibodies (e.g., H-reactive and F-reactive) antibodies were depleted from measles-immune human serum. Serum samples were diluted 1:10 in culture medium (RPMI 1640 (CORNING, Manassas, Va., USA) without fetal bovine serum (FBS)) and subsequently cultured for 4 days onto a monolayer of Mel-JuSo cells either expressing or not expressing MV glycoproteins. Supernatants were collected and tested in a 1:100 final dilution for the presence of H- or F- or VCA-specific antibodies by a FACS-measured immunofluorescence assay, using the stably transfected human melanoma cells Mel-JuSo/MV-H or Mel-JuSO/MV-F as target cells. Epstein-Barr virus (EBV) VCA-specific antibodies were quantified by a commercial ELISA (IBL International, Hamburg, Germany). MV #1 was efficiently neutralized by F-reactive antibodies in measles-immune human serum. A fluorescence plaque reduction micro neutralization assay was used to determine anti-MV-H immunity induced upon vaccination. MV #1 was resistant to the H reactive component of the human anti-measles antibody response.

Figure 2:
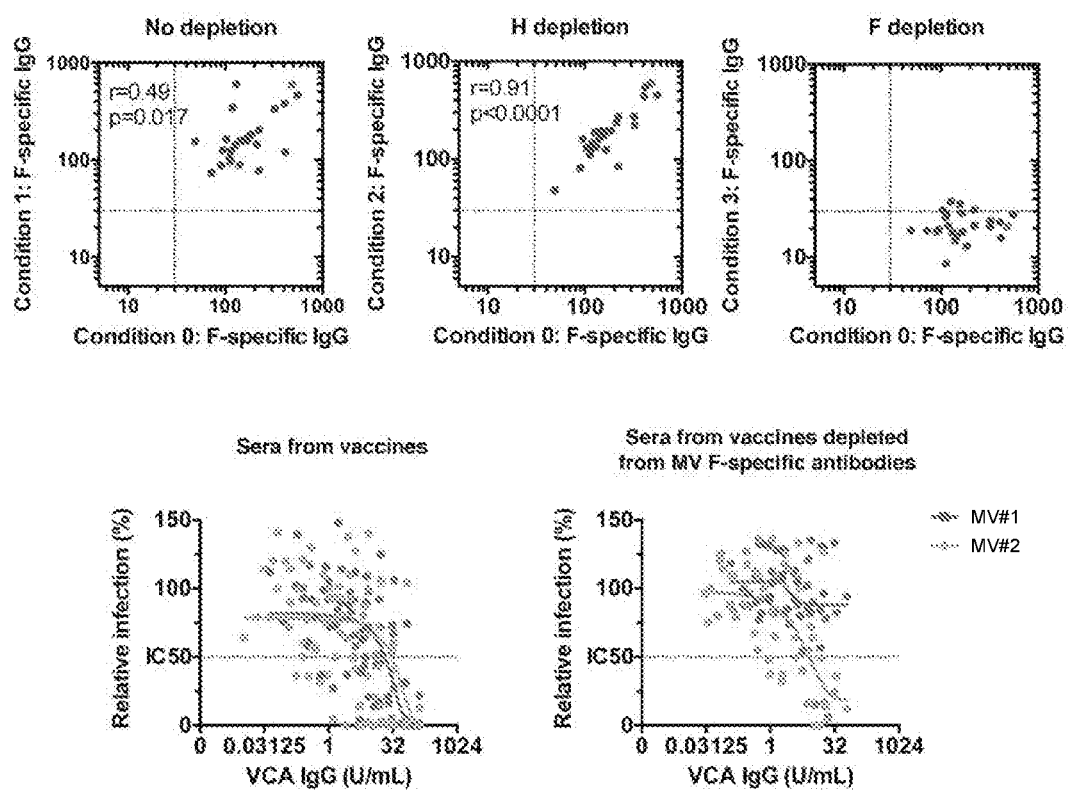
FIG. 2 shows that mutations in MV-H circumvent neutralizing antibodies, but F-specific antibodies neutralize MV.
Figure 3:
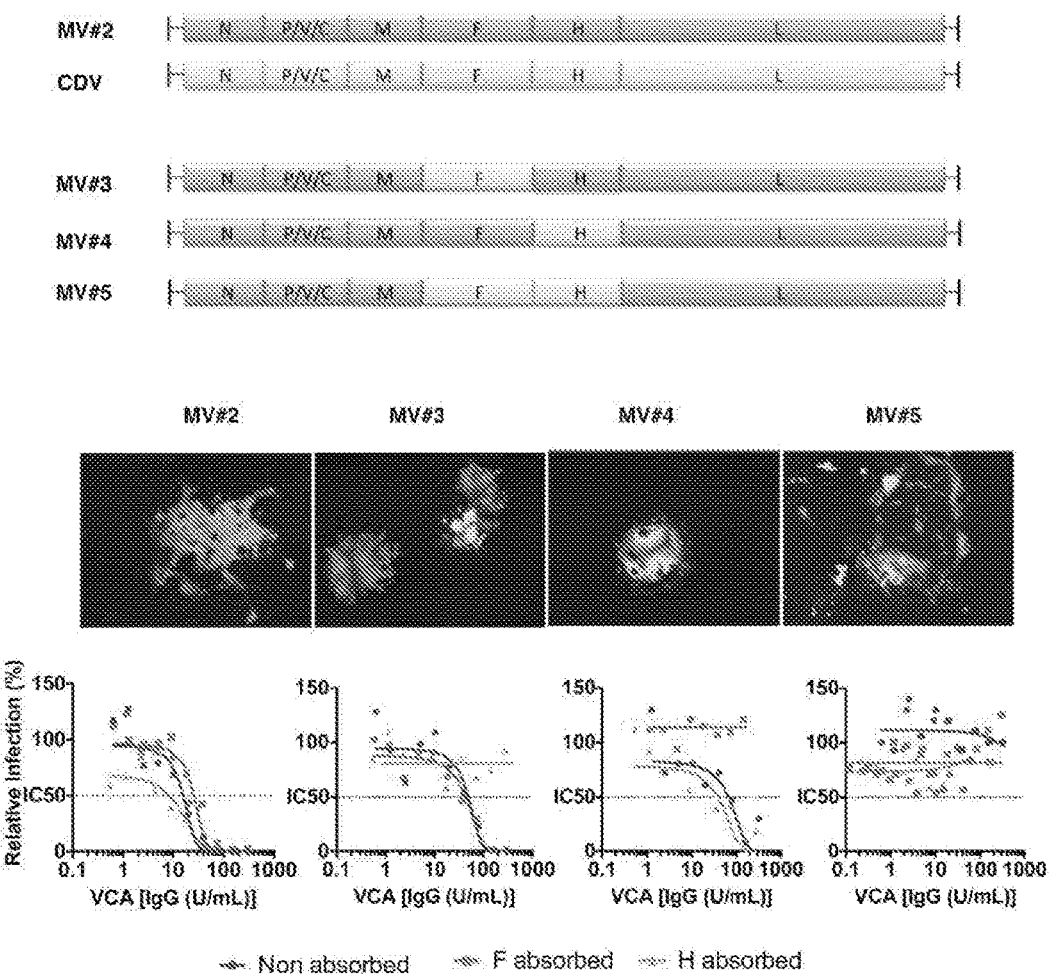
FIG. 3 includes schematics of MV, CDV, and MVs encoding either CDV H, CDV F, or both, and their correspondent neutralization sensitivity by whole pooled human sera or MV H/F specifically absorbed.
Figure 5:
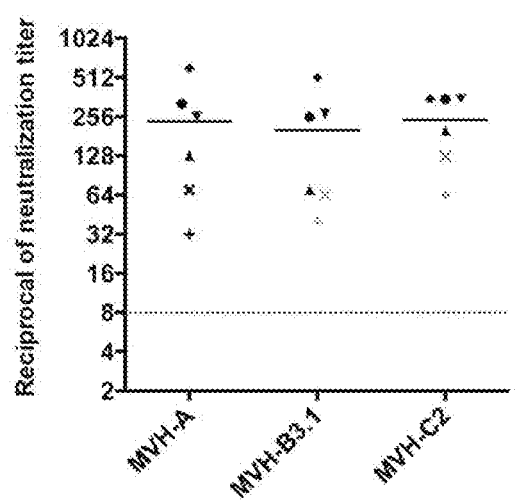
FIG. 5 illustrates that a multiple mutated MV H polypeptide can induce broadly neutralizing antibodies against multiple MV strains.

To confirm that apart from MV H protein-specific antibodies, MV F protein-specific antibodies are also important for MV neutralization, another wild-type Edmonton strain measles virus (MV #3) was produced by replacing the MV F protein of a wild-type Edmonston strain MV with a wild-type Ondersterpoort strain CDV F protein. Two other measles viruses (MV #4 and MV #5) were produced. MV #4 was produced by replacing the MV H protein of a wild-type Edmonston strain MV with a wild-type CDV H protein. MV #5 was produced by replacing the MV F protein of MV #4 with a wild-type (i.e., Ondersterpoort strain) CDV F protein. Schematic representations of MV #3, MV #4, and MV #5 viruses are shown in FIG. 2. The MV #2, MV #3, MV #4 and MV #5 viruses were tested as follows. Vero/cSLAM cells were infected with the different viruses and microphotographs were taken 48 hours post-infection. A neutralization assay was performed and revealed that both MV H and MV F elicit neutralizing antibodies.

A productive heterotypic fusion of CDV Ondersterpoort and MVH #1. CHO cells expressing or not the MV receptors were seeded in a 24 well plate, and were cotransfected with plasmids encoding MVH #1 (1 μg) and F proteins (1 μg; MV vaccine strain, MVF; Ondersterpoort vaccine strain, CDV F). Syncytium formation was evaluated 24 hours later. Syncytium forming activity results demonstrated that CDV F can trigger fusion with no impaired in syncytium formation when coexpressed with MVH #1 directed manner. A virus encoding both MVH #1 and CDV F was rescued and confirm the monotropism for cells expressing CD46.

Surface expression patterns for the MV receptors were examined using flow cytometry. Two days after infection, productive infection was evaluated under a microscope. These results demonstrated that MV encoding MV #1 and CDV F propagated efficiently on cells expressing the CD46 receptor.

C57BL/6 mice (Jackson Laboratories, Bar Harbor, Me., EEUU) were immunized via hydrodynamic delivery with pCG plasmid (5 µg) encoding for MVH protein from MV #1. The neutralization capacity of the antibodies generated evaluated 4 weeks later after blood collection from the jugular vein. Mice sera were heat inactivated and serially diluted either in Opti-MEM. Equal volume of respective virus encoding different MVH gene proteins at 30 PFU/well were mixed with the respective polyclonal antibodies at 2-fold serial various dilutions in 96-well plates (Costar Corp., Cambridge, Mass., USA), incubated at 37° C. for 1 hour and inoculated onto 80 to 90% confluent Vero/hSLAM cells. eGFP autofluorescence was visualized under a fluorescent microscope after 2 days of culture and a neutralization titer was given as the higher dilution blocking 100% of viral infectivity. These results demonstrated that MV #1 provoked an H glycoprotein-directed neutralizing antibody response that cross-neutralizes wild type strains of MV.

Example 2—Additional Recombinant MVs

For this Example 2, MV is referred to as MeV; MV #1 is referred to as MeVΔ7, Δ7, or Δ8; MV #2 is referred to as MeV #1; MV #3 is referred to as Virus 3; MV #4 is referred to as MeV #4; and MV #5 is referred to as MeV #2. The synthesis of several of these were described again in Example 2, and some of the data presented in Example 1 also are presented in Example 2. In addition, MeVΔ7 was used to generate the Δ8 virus.

Cells and Viruses

Vero cells (CCL-81, ATCC), the stably transfected Vero human (Vero/hSLAM) (Ono et al., *J. Virol.*, 75(9):4399-401 (2001)) and dog (Vero/dogSLAM) (von Messling et al., *J. Virol.*, 77(23):12579-91 (2003)) SLAM were grown in in Dulbecco's modified minimal essential medium (DMEM) (HyClone, GE Healthcare Life Science) supplemented with 5% (vol./vol.) heat-inactivated fetal bovine serum (FBS) (Gibco) and 0.5 mg/mL of Geneticin (G418; Corning) (Vero/hSLAM) or 1 mg/mL Zeocin (ThermoFisher, Walthman Mass.) (Vero/dSLAM). Chinese hamster ovary (CHO) cells, CHO-CD46 (Nakamura et al., *Nat. Biotechnol.*, 22(3): 331-6 (2004)), CHO-SLAM (Tatsuo et al., *Nature*, 406: 893-6 (2000)), and CHO-N4 (Liu et al., *J. Virol.*, 88(4): 2195-204 (2014)) were cultured as described. Baby Hamster Kidney cells (BHK) were maintained in DMEM-10% FBS. Viruses were propagated as described elsewhere (Munoz-Alia et al., *J. Virol.*, 91(11):e00209-17 (2017); Munoz-Alia et al., *PLoS One*, 13(2):e0192245 (2018)).

Constructs and Rescue of Recombinant MeVs

The recombinant MeV was based on the molecular cDNA clone of the Moraten/Schwartz vaccine strain contained in p(+)MeV$^{vac2}$(EGFP)N plasmid (del Valle et al., *J. Virol.*, 81(19):10597-605 (2007)). In this plasmid, the enhanced green fluorescent protein (EGFP) was inserted upstream the N gene. To avoid plasmid instability upon its propagation in bacteria, the plasmid backbone was replaced by the pSMART® LCkan vector (Lucigen, Middleton, Wis.) in a stepwise manner following two approaches. In the first approach, a multi-cloning site comprising SacII and NotI restriction enzymes were added to the vector. Then, an optimal T7 promoter followed by a hammerhead ribozyme (HHrbz) (FIG. 7) was inserted upstream the viral genome by insertion of the sequence directly into the forward primer, amplifying the MeV genome up to a unique internal restriction site SacII located at the beginning of the P gene. The SacII-NotI fragment in p(+)MV$^{vac2}$(EGFP)N plasmid was then inserted into the equally digested pSMART® LCkan vector. In the second approach, a cassette containing the human Elongation Factor-1α core promoter, chimeric intron, T7 RNA polymerase promoter, HHrbz and cloning sites was synthesized and ligated into the vector. All plasmid propagations were performed in *Escherichia coli* Stbl2™ cells (Invitrogen, 10268019) grown in at 30° C.

To produce envelope-exchange MeVs, the CDV Onder-sterpoort vaccine strain H (CDV-H) and F (CDV-F) genes originally contained in pCG plasmid (von Messling et al., *J. Virol.*, 75(14):6418-27 (2001)) were used. To replace MeV-H from the MeV backbone, site-directed mutagenesis (QuikChange site-directed mutagenesis kit, Agilent) was first used to removed a SpeI site in CDV-H, and a Y537D substitution was then introduced to reduce binding by cross-reactive neutralizing antibodies in human sera (Zhang et al., *Virology*, 482:218-24 (2015)). PacI and SpeI restriction sites (underlined) were introduced into the beginning and end of the gene, respectively, by polymerase chain reaction using forward primer 5'-ttaattaaaacttagggtgcaagatcatcgataatgctcccctaccaagacaagg-3' and reverse primer 5'-actagtgggtatgcctgatgtctgggtgacatcatgtgattggttcactagcagcctt aatggtggtgatggtggtggctccccttg cggccgcggccggctgggccgctc-taccctcgatacggttacatgagaatcttatacggac-3', leaving the untranslated region (UTR) unchanged. The PCR product was digested with PacI and SpeI and cloned into the MeV backbone. To replace MeV-F from MeV antigenome plasmid, pCG-CDV-F was digested with HpaI/SpeI and inserted into equally digested pCG-MeV-F. The NarI/SpeI fragment of this plasmid was then used to replace that of MeV.

The recovery of recombinant MeVs (rMeV) was performed by co-transfection of rMeV antigenomic plasmid construct, N, P, and L supporting plasmids derived from a MeV isolate genotype B3.1 (Munoz-Alia et al., *Virus Res.*, 196:122-7 (2015)), and a codon-optimized T7 RNA polymerase (obtained from Behur Lee, Addgene plasmid 65974), with Lipofectamine LTX/PLUS transfection reagent (Invitrogen). Transfected cells were co-culture with Vero/hSLAM cells and the virus was amplified thereafter. The identity of the recombinant MeVs was confirmed by Sanger sequencing after RNA extraction from infected cells.

Fusion Assay

Cells (5×10$^5$/well in 6-well plate) were co-transfected using Fugene HD (Promega) with (1 µg) of pCG plasmid encoding for vaccine strain MeV-F and pCG encoding the appropriate MeV-H. Fusion activity was evaluated 24 hours later after Hema-Quik staining (Fisher Scientific 123-745).

To quantify cell fusion, the dual-split luciferase assay was used as described elsewhere (Saw et al., *Methods*, 90:68-75 (2015)). Briefly, effector BHK cells (3×10$^4$) in a black 96-well plates were co-transfected with 33 ng each of the MeV-H and MeV-F expression plasmids and one of the split luciferase plasmids, DSP$_{8-11}$ (obtained from Z. Matsuda). As a control, only the MeV-F and DSP$_{8-11}$ plasmids were transfected. 2×10$^5$ cells per well in 6-well plates of target cells, CHO cells, and CHO cells expressing the respective measles virus receptors were transfected with 1.5 µg of the other dual-split-reporter plasmid (DSP$_{1-7}$). 24 hours after transfection, target cells were detached with Versene (Life Technologies) and co-cultured with the effector cells in Fusion media (DMEM-F12 without Phenol Red+40 mM HEPES), supplemented with 1:1000 dilution of the cell permeable luciferase substrate EnduREN (Promega). Luminescence resulting from cell fusion and mixing of cytoplasmic content between target and effector cells was monitored with a Topcount NXT Luminometer (Packard Instrument Company, Meriden Conn.) at the indicated time points. The data represented the mean and standard deviation of three replicates for each H plasmid.

FACS Analysis and Quantification of Cell Surface Molecules

Cells were washed and detached by using Versene (Gibco) and immediately incubated with phycoerythrin-conjugated antibodies anti-SLAM (FAB1642P; R&D Systems), anti-CD46 (FAB2005P; R&D Systems), and anti-nectin-4 (FAB2659P; R&D Systems), or with control isotype antibody (IC0041P; R&D Systems). After incubation for 1 hour at 4° C., cells were washed again, and fluorescence was measured in a FACSCanto flow cytometry system (BD Bioscience). The number of receptors per cell was estimated in reference to calibration beads (BD QuantiBrite; BD Biosciences).

Recombinant Proteins and Binding Assays

Coding sequence of CD46 ectodomain (residues 35-328) was amplified via PCR from pGEM-CD46 vector (Sino Biologicals Inc., HG12239-G) and inserted into pFUSE vector (pfc1-hg1e3; Invivogen) in frame with the murine Ig κ-chain leader sequence and a 3C protease cleavage sequence at the 5'-end of the Fc region using In-Fusion cloning kit (Clontech). CD46-Fc, SLAM-Fc, and nectin-4-Fc (Munoz-Alia et al., PLoS One, 13(2):e0192245 (2018)) recombinant proteins were expressed in Expi293 cells (Gibco) and purified from culture supernatant as described elsewhere (Munoz-Alia et al., PLoS One, 13(2):e0192245 (2018)). The expression and purification of recombinant soluble MeV-H were performed as described elsewhere (Munoz-Alia et al., J. Virol., 91(11):e00209-17 (2017)). Binding of the receptors-Fc to MeV-H was determined by enzyme-linked immunosorbent assay as described elsewhere (Munoz-Alia et al., PLoS One, 13(2):e0192245 (2018)). The absorbance at 450 nm was measured on an Infinite M200Pro microplate reader (Tecan). The data were analyzed using Prism software (GraphPad) and adjusted to a one-site binding saturation mode to determine the half-saturating concentration (apparent Kd values [dissociation constant]). Values reported exhibited an excellent fit ($R^2 > 0.99$).

Virus Protein Content

Virus preps were heated in the presence of DTT, fractionated into 4-12% Bis-Tris polyacrylamide gel, and transferred to PDVF membranes. Blots were then analyzed with anti-MeV-Hcyt, anti-MeV-N, anti-MeV-F, and anti-GFP probed with conjugated secondary rabbit antibody (ThermoFisher, #31642). The blots were revealed with SuperSignal Wester Pico Chemiluminescent Substrate (ThermoFisher) and analyzed under a ChemiDoc Imaging Sytem (BIO-RAD).

Serologic Assays

Virus neutralization assay was performed based on the fluorescence-based plaque reduction microneutralization (PRMN) assay as described elsewhere (Munoz-Alia et al., J. Virol., 91(11):e00209-17 (2017); Munoz-Alia et al., PLoS One, 13(2):e0192245 (2018); and Munoz-Alia et al., Virus Res., 236:30-43 (2017)). Each assay was repeated at least two times in different days with four replicates per assay. Fifty percent inhibitory concentration (IC50) was calculated after fitting the data to a sigmoidal dose-response (variable slope) with GraphPad software (Prism 7).

Rabbit anti-MeV-H antisera were generated by immunization with adenovirus expressing the MeV-H from the vaccine strain (Lech et al., PLoS One, 8(1):e52306 (2013)).

The following reagents were obtained through BEI Resources, NIAID, NIH: Polyclonal Anti-Canine Distemper Virus, Lederle Avirulent (antiserum, Ferret), NR-4025; and polyclonal Anti-Measles Virus, Edmonston, (antiserum, Guinea pig), NR-4024.

Murine monoclonal anti-hemagglutinin antibodies were produced and characterized as described elsewhere (Muñoz-Alía et al., Virus Research, e00209-17 (2017); Ziegler et al., J. Gen. Virol., 77(Pt 10):2479-89 (1996); Fournier et al., J. Gen. Virol., 78:1295-302 (1997); Ertl O T. Immunodominant regions and novel functional domains on the measles virus hemagglutinin protein. Germany: Eberhard Karls University; 2003; Hu et al., Virology, 192:351-4 (1993); and Masse et al., J. Virol., 78(17):9051-63 (2004)). Polyclonal antibodies were generated by via gene-based hydrodynamic injection (Liu et al., Gene Ther., 6(7):1258-66 (1999)) of C57BL/6 mice with 20 μg of plasmid DNA.

Human serum was collected from the Erasmus MC' serum bank from healthy subjects aged 17-18 (de Swart et al., J. Virol., 79(17):11547-51 (2005)). They were likely never exposed to wild-type MeV and received a monovalent measles vaccination at the age of 14 months and a measles-mumps-rubella vaccination at the age of 9 years. All polyclonal sera and ascites containing mAb were heat inactivated (30 minutes, 56° C.) before testing.

The Epstein-Barr virus (BCA) IgG titer was determined by a commercially available assay (IBL International GMbH, cat. No. 57351). The assay for determining MeV-specific IgG levels was performed as described elsewhere (de Swart et al., J. Virol., 79(17):11547-51 (2005); and de Swart et al., J. Virol. Methods., 71:35-44 (1998)).

Structural Modeling

A model of the MeV-H Stealth was generated at >90% confidence using the program Phyre2 (Kelley et al., Nat. Protoc., 10(6):845-58 (2015)). The structure was then submitted for in silico glycosylation using the GlyPro server world wide web "dot" glycosciences "dot" de), which produced a complex penta-antennary N-glycan model at all predicted N-glycosilation sites, including N168 and N187 that are part of disordered regions. The CD46 receptors from the MeV-H/CD46 crystallographic co-structure (PDB 3INB) was superimposed and manipulated using PyMOL software (pymol "dot" org).

Statistical Analysis

Statistical significance was calculated with GraphPad Prism 7 following the appropriate statistical test.

Results

Modeling an Antigenic Drift into MeV-H

The MeV-H has seven major antigenic sites, and multiple disruptions of up to four of those sites does not abrogate polyclonal antibodies neutralization (Munoz-Alia et al., J. Virol., 91(11):e00209-17 (2017); Lech et al., PLoS One, 8(1):e52306 (2013); and Munoz-Alia et al., PLoS One, 13(2):e0192245 (2018)). It is possible that due to a lack of B cell immunodominance, ablation of all antigenic sites can generate a non-neutralizable variant. To explore this, all epitopes described for MeV-H were systematically disrupted. The experimental design was based on incorporating spontaneous neutralizing mAb escape-mutant selections onto the MeV-H background of genotype H1. This particular strain was chosen based on a previous observation of being one of the most antigenically advanced MeV-H (Munoz- Alia et al., *PLoS One,* 13(2):e0192245 (2018)), which would enable one to minimize the alteration of the otherwise rigid MeV-H protein (Fulton et al., *Cell Rep.,* 11(9):1331-8 (2015)). A list of nAb binding regions was generated, and diruptions of those regions were combined into a single MeV-H, name herein Δ7 (also known as MV #1 in Example 1)(Table 3).

TABLE 3

| Antigenic site | Alternative names | Substitution | mAb resistance | References |
|---|---|---|---|---|
| Φ | E1 | N282K | BH015, BH130 | B |
| Ia | I, VI, E4, LE, V | E235G | E185 | C |
| | | G302R | E39 | C |
| | | Y310C | BH038, BH141, I-29 | A |
| | | Q311R | E103 | C |
| Ib | NE, IV | L249P | BH047, BH059, BH129 | D |
| IIa | II, SSE, VII | E488K | BH097 | E |
| | | G491D | 16CD11 | F |
| IIb | II, SSE, VII | 416DLS→NLS | E128 | C |
| | | | BH125 | B |
| III | III, IIIA, IIIB, VII, RBE, E2 | S189P | I-44 | F |
| | | D505T | 80-II-B2 | G |
| | | R533G | C155 | H |
| | | | 16DE6 | F |
| | | R547G | 20H6 | E |
| | | F552V | I-41 | F |
| | | R377Q, M378K | L77 | I |
| IV | 'noose', HNE, I, E3, D, D/E | P397L | BH006, BH216 | (54) |
| | | N405S | 8905 | H |
| | | E471K | BH030 | Example 2 herein |

For references:
A = Lech et al., *PLoS One*, 8(1): e52306 (2013).
B = Munoz-Alia et al., *PLoS One*, 13(2): e0192245 (2018).
C = Tahara et al., *J. Virol.*, 87(1): 666-75 (2013).
D = Munoz-Alia et al., *J. Virol.*, 91(11): e00209-17 (2017).
E = Lech et al., *Virology*, 454-455: 237-46 (2014).
F = Hu et al., *Virology*, 192(1): 351-4 (1993).
G = Hummel et al., *J. Virol.*, 69(3): 1913-6 (1995).
H = Muñoz-Alía et al., *Virus Research*, 236: 30-43 (2017).
I = Liebert et al., *J. Virol.*, 68(3): 1486-93 (1994).
J = Finsterbusch et al., *J. Gen. Virol.*, 90: 2739-45 (2009).

Tropism engineering into MeV-H

Figure 8:
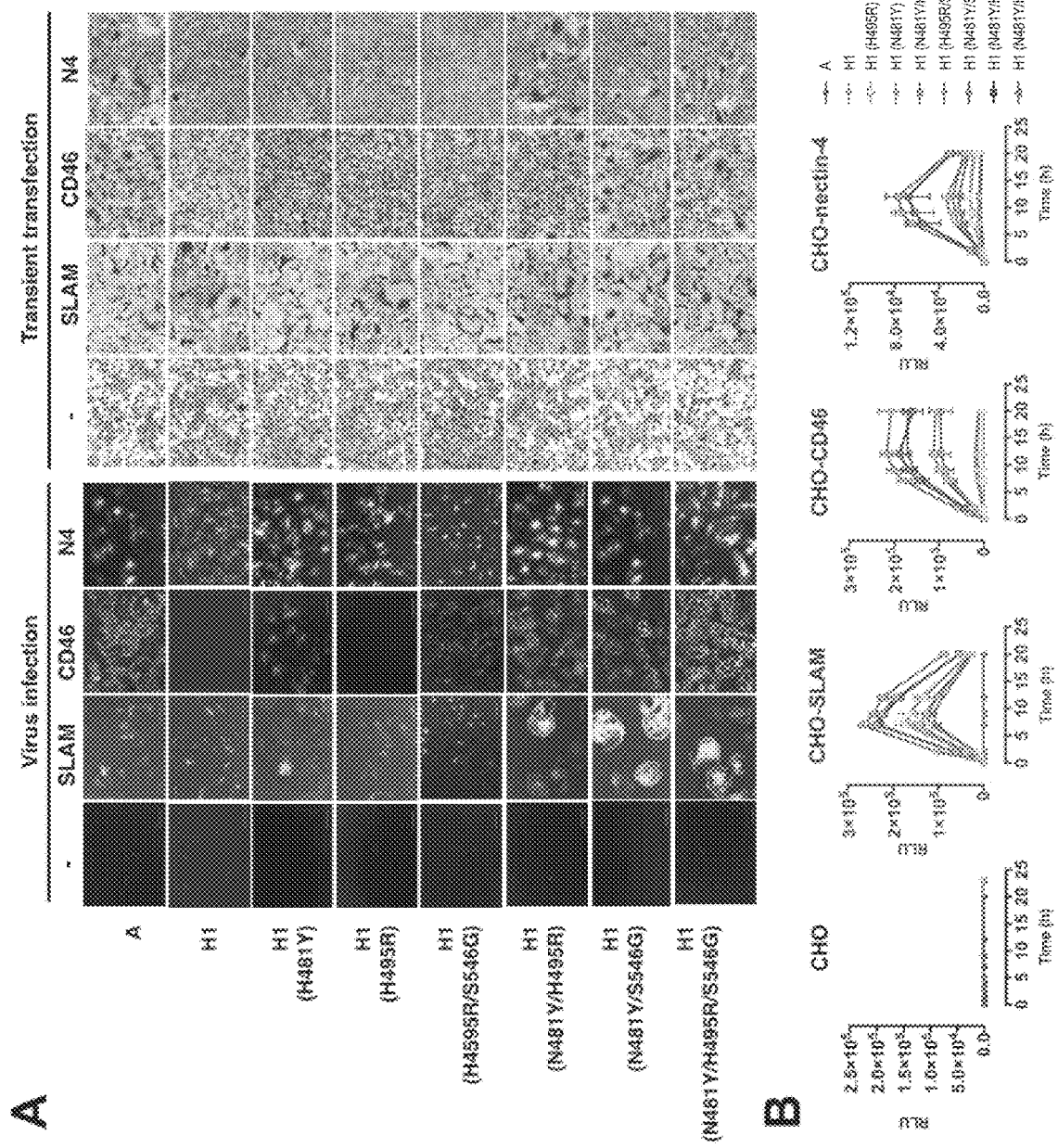
FIGS. 8A-B. Engraftment of CD46 footprint onto MeV-H genotype H1. (A) Left panel. CHO cells expressing or not the cellular receptors (SLAM, CD46 and nectin-4) were infected with GFP-expressing MeV encoding the indicated MeV-H, at moi 0.1. eGFP autofluorescence was recorded 72 hours post infection. (A) Right panel. Cell-fusion triggered by co-expression of vaccine MeV-F and the indicated MeV-H. Cells were stained 48 hours later with Giemsa and microphotograph were taken. Magnification, ×40. (B) Kinetics of cell-cell fusion as determined by split luciferase assay.

Since mutations in antigenic site III (receptor binding site, RBS) were incompatible with wild-type tropism (SLAM and nectin-4), the plan was to switch receptor-specificity towards CD46 via a number of amino acid substitutions: N481Y (Lecouturier et al., *J. Virol.,* 70(7):4200-4 (1996)), H495R (Okada et al., *J. Virol.,* 83(17):8713-21 (2009)), and S546G (Shibahara et al., *J. Gen. Virol.,* 75:3511-6 (1994)). To evaluate the impact of the amino acid substitutions in the receptor-dependent fusion activity, transient expression of the MeV-H mutants was performed in combination with the vaccine-derived MeV-F. The corresponding recombinant MeV were also rescued by reverse genetics since cell-cell transmission can occurred in the absence of obvious syncytium formation (Langedijk et al., *J. Virol.,* 85(21):11242-54 (2011)). The results were displayed in FIG. 8. When MeV-H vaccine strain (A) was used, both virus entry and cell fusion were observed in CHO cells expressing either SLAM, CD46, or nectin-4. Similarly, MeV-H H1 allowed for virus entry and syncytia formation in SLAM and nectin-4-expressing cells. The introduction of N481Y, H495R, or H495R/S546G in the latter background did not significantly increase CD46-dependent fusion activity as seen by transient transfection assays. However, virus entry was observed in the absence of syncytium formation for the N481Y and H495R/S546G mutants. The inclusion of H495R in the context of N481Y mutant restored the levels of CD46-dependent fusion to those observed by MeV-H A. The addition of S546G in this mutant enhanced almost 2-fold the CD46-dependent fusion, and a similar increase was observed with the N481Y/S546G mutant. Nevertheless, CD46-dependent enhancement infection was observed only when the triple mutant (N481Y/H495R/S546G) was used, and this combination was therefore chosen as background of nAb-escape mutations.

Figure 9:
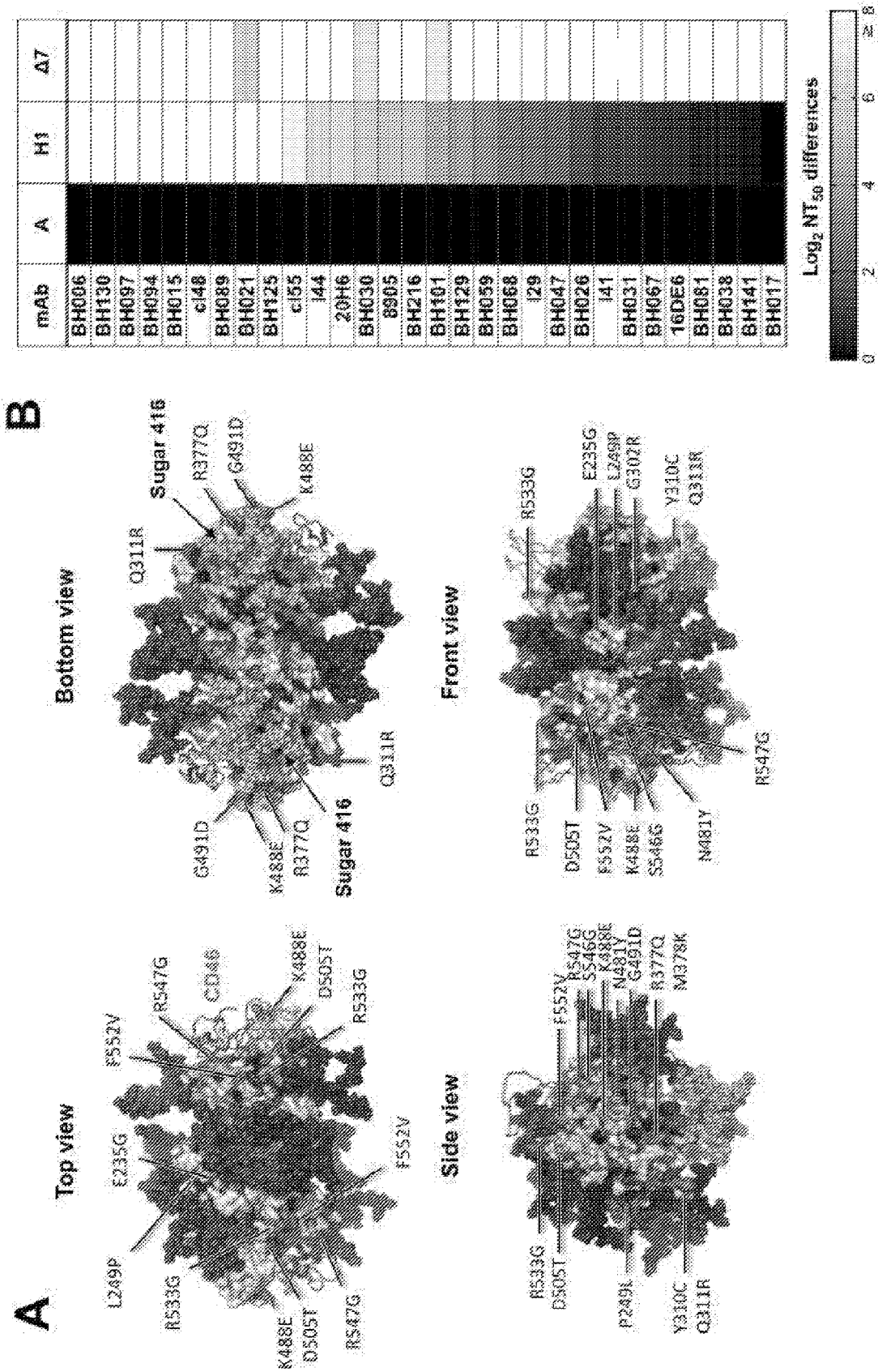
FIGS. 9A-B. Antigenic variation in Δ8 viruses. (A) Model of the dimeric structure of MeV-HΔ7 with N-linked sugar attached. N-linked sugars are depicted as black (N168-, N200-, N215 linked) or orange spheres (N416-linked). Amino acid differences with regard to the MeV-H vaccine Moraten strain are indicated. Blue, MeV-H-genotype-H1-specific changes; Red, engineered nAb-escape mutations. (B) Antigenic map of viruses encoding different MeV-H proteins. Antigenicity was determined by virus plaque reduction microneutralization (PRMN) assay and color-coded according to the $Log_2NT50$ differences. Individual neutralization curves are shown in FIG. 19.

MeV-H can Systematically Resist Neutralization by 30 Known Murine Monoclonal Antibodies Table 3 was initially used as a foundation to generate a MeV-H globular domain escape virus. Using this information, together with the triple CD46-tropism substitutions, a Δ7 virus was directly engineered, in which all seven operationally non-ovelapping antigenic sites so far described are disrupted (Φ, Ia, Ib, IIa, IIb, III, and IV) (FIG. 9A).

To determine whether the number of mutations introduced was suffice to abrogated neutralization of other nAbs specific for each site, the neutralization sensitivity of viruses possessing MeV-H A, H1 and Δ7 was determined against a panel of 30 mAbs. The results were summarized in FIG. 9B, showing that A viruses were neutralized by all 30 nAbs tested whereas this number was reduced to 18 for H1 viruses. On the other extreme, the Δ7 viruses were only neutralized by nAb BH030.

The fact that both Δ7 and H1 viruses were neutralized similarly by BH030 indicated that the mutations introduced in Δ7 did not eliminated this nAb epitope. However, both viruses showed a 18-fold reduction in sensitivity to neutralization when compare to A viruses ($IC_{50}$ of 1312 ng/mL versus 71.6 ng/mL).

Figure 10:
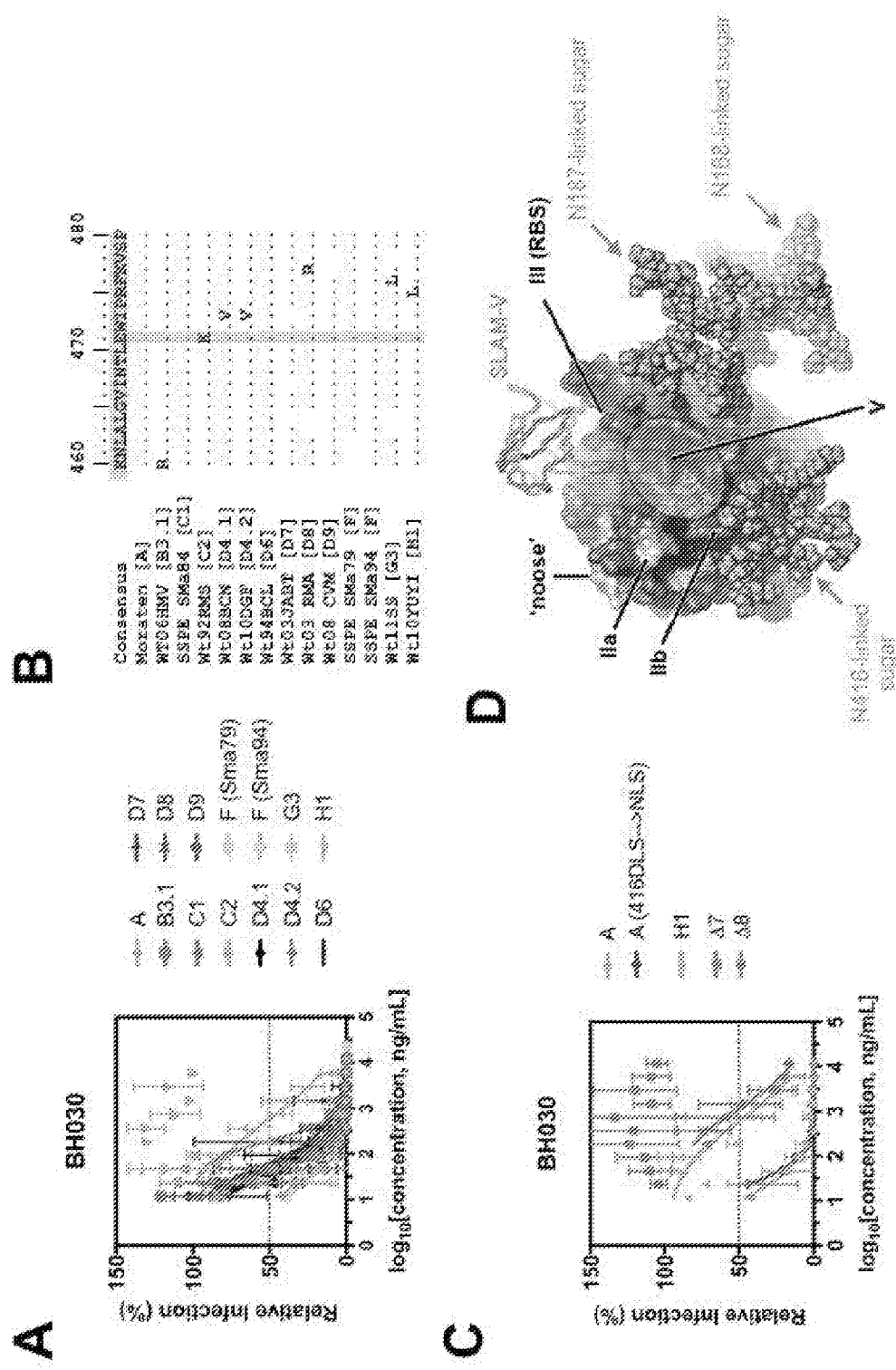
FIGS. 10A-D. BH030 defines a novel antigenic site onto MeV-H. (A) PRMN assay of mAb BH030 against recombinant MeV encoding different genotype-specific MeV-H. Data points were fitted by non-linear regression analysis with Graph Pad Prism. Inhibitory concentration 50% ($IC_{50}$) is indicated by a dotted line. Of note, C2 viruses selectively escape neutralization. (B) Amino acid sequence alignment for the putative BH030 epitope, showing the differential amino acid substitution in C2 viruses. Consensus is set forth as SEQ ID NO:15. (C) H1 viruses show resistance against BH030 neutralization in comparison with A viruses and A mutant (416DLS→NLS), but are still neutralized, as Δ7 viruses are. The addition of E471E into Δ7, name herein Δ8, results in BH030 escape. (D) Putative antigenic site defined by mnAb BH030. Glu471 is not masked by N416-linked sugar, which shields site IIb, and therefore define a putative new antigenic site, V, that expands from sites IIb to site III.

The following was performed to determine whether this phenotype was applicable to other wild-type-specific MeV-H proteins or whether it was a peculiarity of the H1 genotype background used. Neutralization analysis indicated that H1 viruses possessed indeed some resistance against neutralization by BH030 in comparison with A, B3.1, C1, D4, D6, D7, D8, D9, F, and G viruses. However, C2 viruses did show a complete lack of neutralization sensitivity (FIG. 10A). Based on the sequence analysis of the amino acid sequence and molecular structure of MeV-H, a E471K mutation was identified as a candidate for nAb resistance (FIG. 10B). To confirm these predictions, the E417K mutation was inserted into the Δ7 virus (this new virus was termed the "Δ8 virus"), and the Δ8 virus's neutralization sensitivity to nAb BH030 was assessed. Different from Δ7 viruses, Δ8 viruses displayed full escape from BH030-mediated neutralization (FIG. 10C). Interestingly, E471 lies within the region assigned to antigenic site IIb (II in Tahara et al., *J. Virol.,* 87(1):666-75 (2013) or "sugar-shielded epitope" in Tahara et al., *Viruses,* 8(8): pii:E216 (2016)), which is defined for being masked by an N416-linked sugar present in some genotypes (FIG. 10D). To confirm that a N416-attached sugar does not protect from BH030 neutralization, the neutralization sensitivity of a D416N mutant A virus (Munoz-Alia et al., *PLoS One,* 13(2):e0192245 (2018)) was tested. Given that Δ7 viruses also possessed a N416 sugar, no resistance to neutralization was observed suggesting that BH030 might target a new operationally non-overlapping antigenic site (designed herein as V, which presumably expands between antigenic sites IIb and III (FIG. 10D). These results showed that mutations of key residues in major antigenic sites can be combined to result in neutralization escape of large panel of 30 neutralizing antibodies.

Epitope Elimination into MeV-H Abolishes Cross-Neutralization

Figure 11:
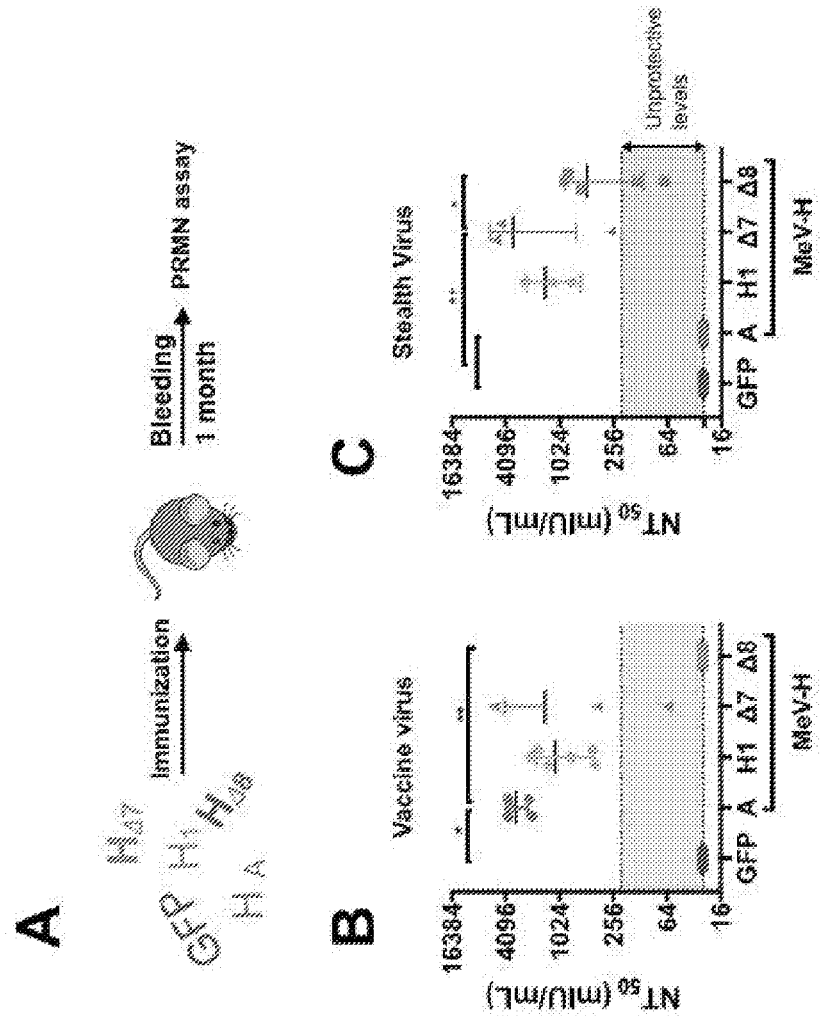
FIGS. 11A-C. Immunogenicity of a drifted MeV-H. (A) Schematic representation of the experiment. C57BL/6 mice were intravenously injected within 5 sec with expression plasmids for GFP (negative control) or different MeV-H variants. One month later, neutralizing antibodies activity was assessed by PRMN assay against vaccine virus (B) or Δ8 virus (C). Each data point represents a single individual. Missing points were due to animal death or scarcity of material. Data from two different immunizations are included. Grey shading indicates a level of neutralizing antibodies considered unprotective against the disease. Lowe dotted lines indicate the limit of detection for the assay.

The following was performed to determine whether the B-cell epitope disruption in MeV-H affected its antigenicity. Mice were given a hydrodynamic injection of MeV-H encoding plasmid, and the antibody responses were evaluated one month later (FIG. 11A). Neutralization assays showed that mice immunized with MeV-HΔ7 had lower titer of neutralizing antibodies than MeV-HA but did not reach statistical significance, likely due to variability (FIG. 11B). MeV-HΔ8 was nonetheless unable to generate any detectable levels (FIG. 11C). The following was performed to assess whether MeV-HΔ8 was generating non-cross reactive antibodies against new epitopes by probing the neutralization activity of Δ8 viruses themselves. The results shown in FIG. 11C showed that Δ8 viruses were neutralized by homotypic antibodies, i.e., antibodies triggered by immunization with MeV-H Δ8, as it was by anti-MeV-H H1 and Δ7, for having epitopes in common but distinct from MeV-H A. Those neutralizing antibodies induced by MeV-HA immunization exerted no neutralizing activity against Δ8 viruses. Then, elimination of multiple antigenic sites abolishes cross-neutralization and allows the virus to escape an anti-MeV-H polyclonal response.

Figure 12:
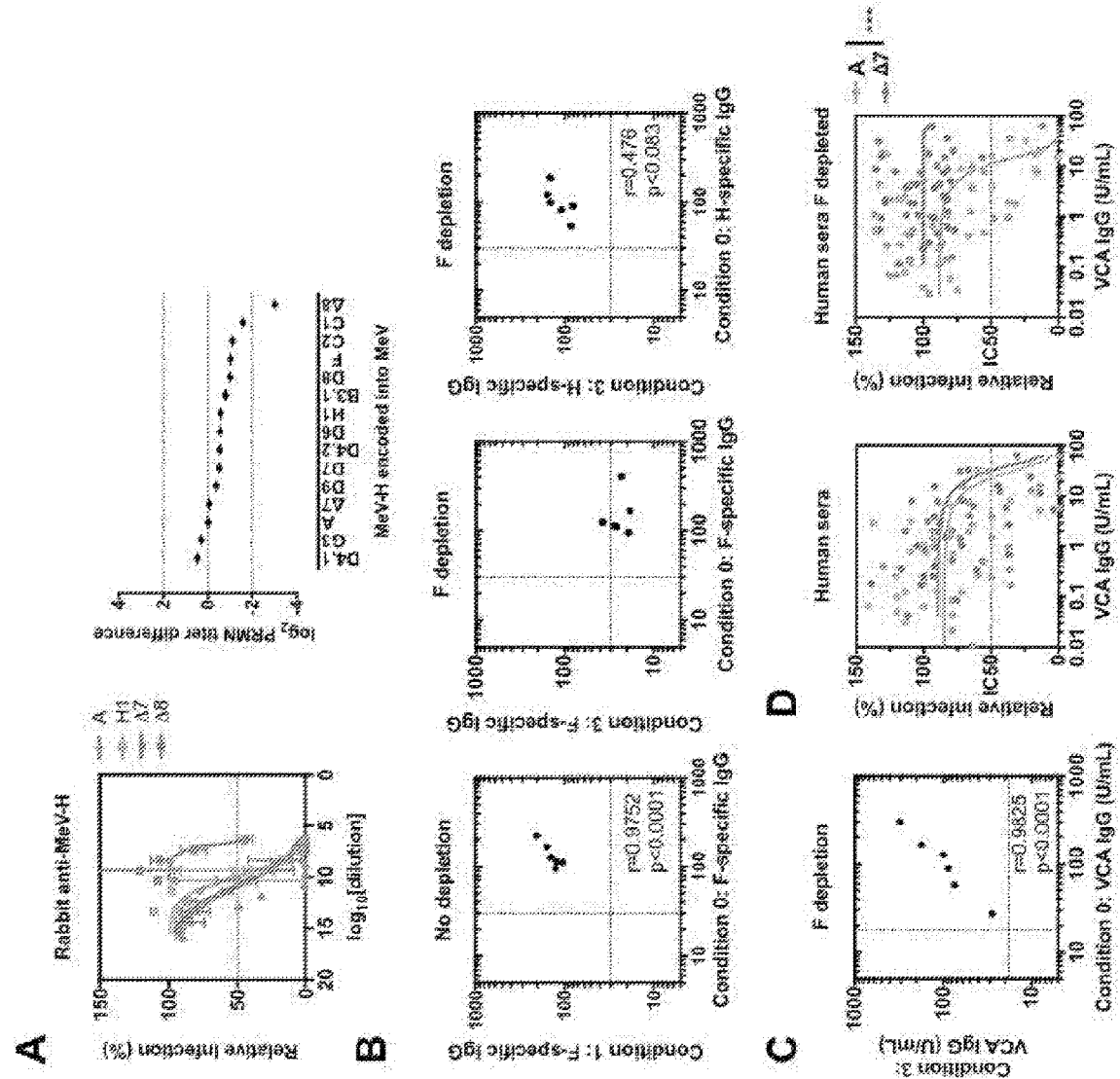
FIGS. 12A-D. Δ8 viruses escape a broader anti-MeV-H polyclonal response. (A) Left panel, PRMN assay of rabbit anti-MeV-H polyclonal antibodies against vaccine and MeV-H mutant viruses (Δ7 and Δ8). Curves were fitted by nonlinear regression to calculate $NT_{50}$ values. Right panel. Neutralization titer differences (ND) between viruses. The same rabbit anti-MeV-H polyclonal antibodies were further tested against a panel of recombinant viruses encoding genotype-specific MeV-H genes or the Δ8 mutant, the $NT_{50}$ was calculated as in the left panel, and the ND are plot as $log_2$. A difference ≥2 $log_2$ is considered substantially antigenic different (dotted line). (B) Monitoring of MeV glycoprotein depletion conditions. IgG antibody levels after human sera incubation with cells non-expressing or expressing either of MeV glycoproteins MeV-H and MeV-F (FIG. 20), compared to those levels in untreated human sera (condition 0). Serum samples were diluted 1:10 in culture medium and subsequently culture for 4 days onto a monolayer of Mel-JuSo cells (Mel-JuSo/wt, condition 1; Mel-JuSo-H, condition 2; Mel-JuSo-F, condition 3). Supernatants were collected and tested for the presence of MeV-F and MeV-H-specific antibodies by a FACS-measured immunofluorescence assay. Dotted line encloses values considered negative. (C) VCA IgG levels in U/mL remaining after MeV-F-specific depletion condition. (D) Neutralization capacity of polyclonal human sera against vaccine and Δ8 viruses. Sera samples were collected from healthy vaccinated young adults and were left untreated or depleted from MeV-F-specific antibodies. Epstein-Barr virus (EBV) VCA IgG levels were used to make comparison of the neutralization potency between conditions, accounting for dilution factors between them. Data are presented as the mean of individual sera samples (N=6). Trend line of neutralization curve across samples was determined by non-linear regression fitting. ***$P<0,0005$, Wilcoxon matched-pairs signed rank test.

Δ7 Viruses can Escape Polyclonal Measles Vaccine-Induced Neutralizing Antibodies if Devoided of MeV-F-Specific Antibodies Different animal models might exhibit a different antibody repertoire (Nachbagauer et al., *Nat. Immunol.*, 18(4):464-73 (2017)). The breath of antibodies arisen in rabbits after MeV-H A immunization was assessed via neutralization analysis. Although virus Δ8 displayed a trend towards neutralization (FIG. 12A), it exhibited a 8-fold (3 $\log_2$) reduction in $ND_{50}$ titer in comparison with the vaccine virus. Since a 4-fold difference (2 log 2 or antigenic units (Smith et al., *Science*, 305(5682):371-6 (2004)) or higher warrants an update of the human seasonal influenza vaccine (Russell et al., *Vaccine*, 26(Suppl 4):D31-4 (2008); and Garten et al., *Science*, 325(5937):197-201 (2009)), virus Δ8 was considered significantly antigenically different from the vaccine virus. On the contrary, the immediate precursor virus (Δ7) was antigenically indistinguishable as the parental precursor was (H1). Because a K471E mutation distinguishes Δ7 from Δ8 viruses and led to antigenic variation, there was a desire to assure that the antigenic differences were the results of the combination of all mAb-escape mutant selections and not to the existence of dominant mutants. Thus, a previous panel of recombinant MeV possessing other genotype-specific MeV-H gene proteins were tested (Munoz-Alia et al., *J. Virol.*, 91(11):e00209-17 (2017); and Munoz-Alia et al., *PLoS One*, 13(2):e0192245 (2018)). Of particular interest was the MeV C2 since it possessed the K471E mutation. However, the differences in the PRMN titers were less than 2-fold across the board and therefore considered insignificant. Overall, these results suggest that antigenic variation in measles virus has both an incremental and a pulsed component; i.e. beyond an antigenic threshold, amino acid substitutions might have an accumulative effect.

Since Δ7, but not Δ8, viruses could potentially be used as a pre-vaccine in infants with maternal antibodies, tests were performed to test whether the antigenic variation in Δ7 could lead to a reduce recognition by sera from patients having received the measles vaccine. This initially involved selecting for testing six sera samples from Dutch individuals aged 17 to 23 at the time of serum collection. Based on the neutralization titer and the record of measles outbreak in the Netherland, the human samples likely correspond to two-dose recipients of the measles vaccine. Δ7 virus and vaccine strain virus were tested by PRMN with human sera #126, #128, #129, #134, #136, and #137. The mean $ND_{50}$ titer for the Δ8 virus was 1.41-fold lower (0,50 antigenic units) than that of the homologous titer of the vaccine strain, indicating a lack of antigenic variation between the two viruses. A correlation was found between MeV-H and MeV-F-specific antibodies (Pearson R=0.54, p<0.05). To test whether MeV-F specific were masking a potential antigenic variation, MeV-F specific antibody were depleted, and the assay was repeated. As illustrated in FIG. 12B, incubation of the human sera with mock transfected cells (condition 1) resulted in no decrease of the MeV-F specific IgG antibodies in comparison with the untreated sample (condition 0). Conversely, incubation with MeV-F-expressing cells resulted in the depletion of MeV-F-specific antibodies, whilst MeV-H-specific antibody levels remained unchanged. To account for small dilution factors introduced upon difference depletion conditions, Epstein Barr VCA IgG antibodies, broadly prevalent in the human population, were additionally tested, and they were used as control of the level of antibodies used thereof (FIG. 12C). Then, both undepleted and MeV-F-depleted human sera were re-tested for their neutralization capacity. Whereas MeV-F-depleted human sera lost insignificantly neutralization potency against the vaccine virus (1 antigenic unit), the reduction was now significant (7-fold) when Δ7 viruses were compared with the vaccine virus (FIG. 12D).

These results indicate that vaccination in humans induce a narrower neutralizing antibody response than rabbits, and Δ7 viruses could potentially close the gap of vaccination for young infants if devoid of anti-MeV-F antibodies.

MeV-H and MeV-F Elicit Neutralizing Antibodies

Figure 13:
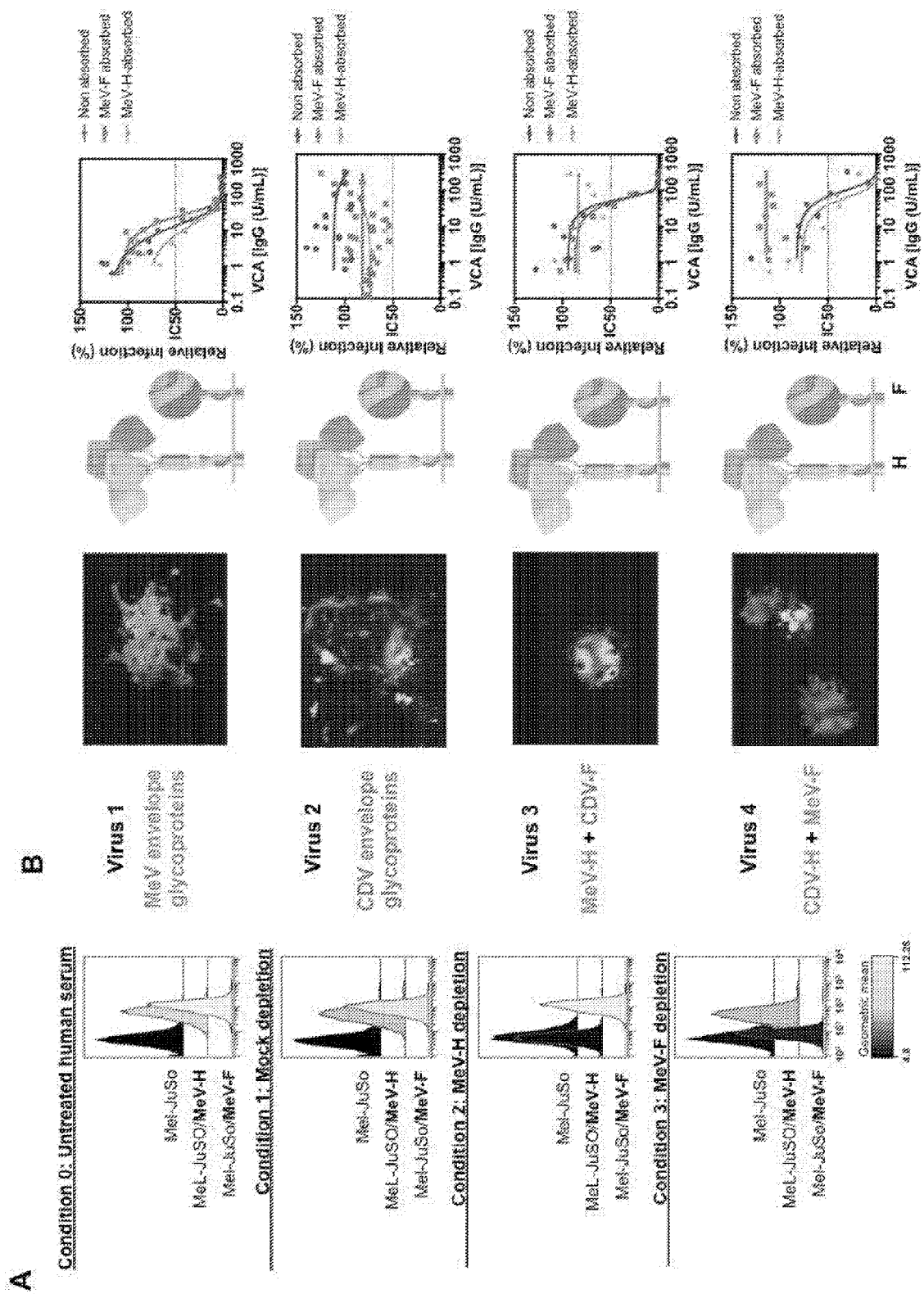
FIGS. 13A-B. Role of MeV-H and MeV-H in virus neutralization. (A) MeV glycoprotein specificity of pooled human sera. Conditions and IgG specific levels were described and determined as in FIG. 12. Data are shown as histogram plots. (B) PRNM of envelope-exchange viruses. Isogenic rMeV encoding MeV envelope glycoproteins (virus 1, denoted in red) or CDV (virus 2, denoted in blue) as well as viral chimera between them (virus 3 and 4), were used for the neutralization sensitivity against human sera preincubated with control cells (non absorbed) or cells expressing either MeV-H or MeV-F glycoproteins. Representative syncitia are shown.

Neutralizing antibodies against the MeV-F in measles-immune human sera can buffer the effect of accumulative antigenic substitutions in MeV-H. To further gain insights into the contribution of the two MeV glycoproteins to virus neutralization, a two-fold approach was used: 1) Depletion MeV-H and MeV-F-specific antibodies (FIG. 13A) and 2) Study of the neutralization sensitivity of an isogenic set of viral chimera with three different glycoprotein-exchanges. This envelope-exchange virus had all genes derived from MeV with the exception of H and F, which were either singly and doubly exchanged with the related but non-cross reactive Canine Distemper Virus (CDV) H and F (Miest et al., *Mol. Ther.*, 19(10):1813-20 (2011); and Zhang et al., *Virology*, 482:218-24 (2015)). Thus, double switching of MeV-H and MeV-F protein genes for those from CDV generated MeV #2, whereas a single switch in either MeV-H or MeV-F produced MeV #3 and MeV #4, respectively (FIG. 13B). The CDV-H protein gene used possessed an intentional Y537D substitution apropos the Ondersterpoort vaccine strain, since it was shown to reduce potential cross-neutralization of CDV by human sera (Munoz-Alia et al., *J. Virol.*, 91(11):e00209-17 (2017); Zhang et al., *Virology*, 482:218-24 (2015)). The parental MeV (MeV #1) as well as all three chimeras (MeV #2, MeV #3, MeV #4) formed indistinguishable syncytia in Vero cells, demonstrating heterotypic complementation (FIG. 13B).

For the MeV H or MeV-F-specific antibodies, a commercially available pool of human sera composed from approximately 60 to 80 American donors was used. Due to the high antibody titers in this pool, it is likely to have been induced mainly by exposure to wild-type viruses (Itoh et al., *J. Clin. Microbiol.*, 40(5):1733-8 (2002)). FIG. 13A illustrates the depletion process. Serum absorption with MeV-H-expressing cells (condition 2) completely removed all human serum binding activity to MeV-H protein, whilst MeV-F specific antibody levels remained unaffected. In contrast, absorption with MeV-F (condition 3) specifically removed human serum binding to MeV-F whilst MeV-H-specific antibodies remained unaffected. Serum absorption with the parental cell line resulted in no decreased of the human serum binding to both MeV-H and MeV-F in comparison to the original human serum material (condition 1 and 0, respectively).

The neutralization potency of MeV-H and MeV-F reactive antibodies was then measured in measles-immune human. The PRMN assay showed that absorption of either MeV-F or MeV-H component did not substantially affect neutralizing activity from human sera against MeV (MeV #1). On the other hand, serum absorption with both MeV-F and MeV-H resulted in the complete loss of neutralizing activity from human sera. Thus, both MeV-H and MeV-F-specific antibodies were equally important for neutralizing MeV. As expected, the measles-immune human sera did not show neutralizing activity against MeV #2, regardless of the sera treatment. On the other hand, MeV #1, MeV #3 and MeV #4 were efficiently neutralized without distinction by non-absorbed sera. Concerning the viral chimera with simple exchanges (MeV #3 and MeV #4), only when the MeV-specific antibody component that matched that present in the virus was depleted, did they show resistance to neutralization. These results indicate that both MeV-F and MeV-H are immunogenic and they cooperate to buffer antigenic variations.

Antigenic Novelty does not Sacrifice Fitness

Figure 7:
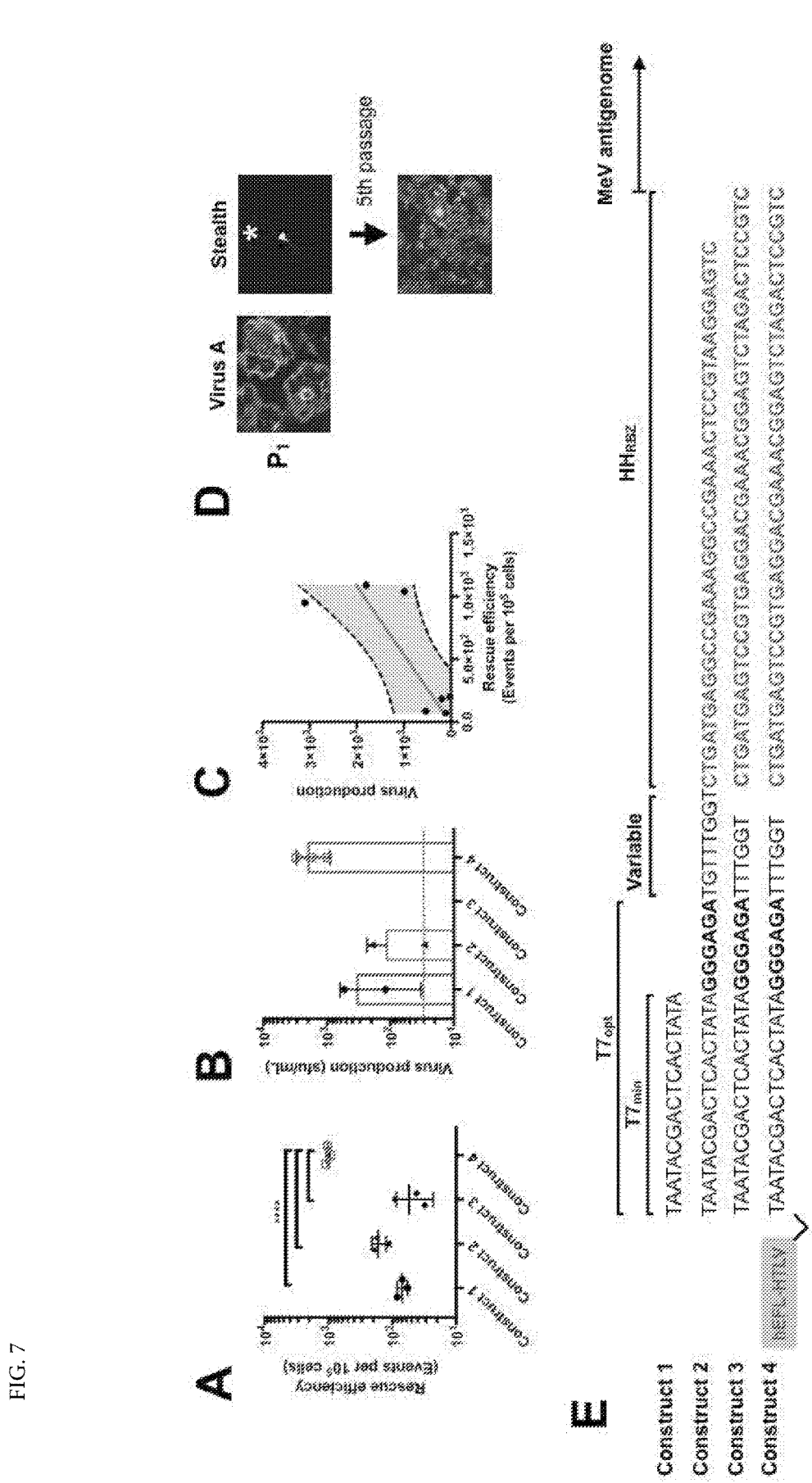
FIGS. 7A-E. Reverse genetic system for Stealth virus rescue: Optimization of antigenome-expressing plasmid. (A) Number of cells expressing GFP as determined by flow cytometry three days after transfection of the BHK rescue cells. (B) Virus production on day three after transfection was determined by freeze-thaw rescue cells ($P_0$) and titrating on Vero cells. (C) Scatter plot showing the correlation between rescue efficiency and virus production. (Pearson r=0.789, p<0.05). Dashes lines represent 95% confidence interval. (D) Rescue of recombinant viruses. Rescue cells were overlaid 3 days after transfection onto Vero cells, and syncytia formation was evaluated 3 days afterwards. * indicates lack of representativeness in the microphotograph. Arrow indicates a single GPF-positive cells. After five semi-blind passages, Stealth virus started to spread similarly to the parental virus. (E) Plasmid constructs used in this study. Shown are the key sequence variations between constructs. $T_{min}$ is a minimal T7 promoter and the addition of GGGAGA (SEQ ID NO:10) drives higher levels of gene expression ($T_{opt}$). However, an optimal T7 promoter requires a self-cleaving hammerhead ribozyme (HHrbz) (Yun et al., J. Virol., 89(2):1242-53 (2015)). Construct 1 (SEQ ID NO:11) and Construct 2 (SEQ ID NO:12) are shown. Construct 3 (SEQ ID NO:13) was described elsewhere (Beaty et al., mSphere, 2(2):ppi00376-16 (2017)). Construct 4 (SEQ ID NO:14) has additionally a 5' the Elongation Factor-1a core promoter (hEFL-HTLV) followed by a chimeric intron sequence. All constructs had the Hepatitis delta ribozyme (HDV) and T7 terminator downstream of the MeV antigenome.

We next hypothesized that the breadth of antibody response against both MeV envelope glycoproteins harbors the antigenically staticity of MeV. In an attempt to address this hypothesis, the rescue of Δ8 viruses was pursued in combination with the heterotypic CDV-F, as a proxy for a fully antigenically distinct virus (this virus was referred to as Stealth going forward). MeV Stealth was not obtained until the robustness of the MeV rescue system was improved. Different from the rescue of the parental recombinant MeV Moraten vaccine, MeV Stealth was isolated and expanded from a single GFP-positive cell observed after multiple independent rescue attempts. After five semi-blind passages, the virus was able to spread through the cell monolayer (FIG. 7). The virus was further propagated to produce virus stock and tested for Sanger sequencing and western-blot analysis. Immunoblotting of purified virions demonstrated that Stealth lacked the homotypic MeV-F protein and showed otherwise a similar protein content to the vaccine strain (FIG. 14B). Moreover, sequencing results showed no compensatory mutation in either of the glycoproteins-coding sequence, further confirming the viability of a Stealth virus encoding MeV-HΔ8 in combination with CDV-F.

To determine whether MeV Stealth associated a fitness trade-off, the growth kinetic of MeV Stealth was examined in cultured cells. Those kinetics were compared with those of recombinant MeVs possessing MeV-H A, MeV-H H1, and MeV-HΔ8. MeV A replicated to higher titers at 12 and 48 hpi than Stealth and Δ8 viruses (FIG. 14A). These two viruses showed a 24 hour lag titer peak. MeV H1 replicated to lower titers than any of the other viruses thorough the time course. Since MeV Δ8 possessed a MeV-H derived from MeV-H H1, these results indicated that the mutations introduced into MeV-H cooperate for a better complementation with heterologous F proteins.

Next, 15 human sera samples were used to determine whether Stealth virus was indeed resistant to neutralization by human antibodies triggered by the measles vaccine (virus A). The pooled human sera used before was avoided since high titers are indicative of different exposure histories to measles virus, which might have induced different repertoires of genotype-specific neutralizing antibodies (de Swart et al., *J. Gen. Virol.*, 90:2982-9 (2009); Tamin et al., *J. Infec. Dis.*, 170:795-801 (1994); and Munoz-Alfa et al., *Virus Research*, 236: 30-43 (2017)). This could complicate future interpretations since antigenic drift in Stealth was modeled by monoclonal antibodies induced by the vaccine virus. CDV-vaccinated ferrets were used as a negative and positive control for neutralization of vaccine and Stealth virus, respectively. Sera #126, #128, #129, #134, #136 and #137, used in FIG. 12 could not be tested due to material scarcity. $NT_{50}$ values of the samples tested showed an overall geometric mean 5.39-fold lower (2.43 antigenic units) in neutralization potency against Stealth virus, ranging from 3.12 to 10.9-fold (FIG. 14C). Serum 152 yielded a less than 4-fold lower (1.64 antigenic units) $ND_{50}$ titer against Stealth virus and that of serum 131 and 157 were in the threshold (4-fold). Of all sera tested, serum 152 was the only sera showing protective levels against Stealth virus (430 mIU/mL) and had the highest $NT_{50}$ titer of all human sera tested against the vaccine strain (1344 mIU/mL). It was then tempting to speculate that the magnitude of the antibody response against the homotypic vaccine determined whether or not protective levels against Stealth virus infection were achieved. Correlation analysis showed support of the hypothesis (Person r=0.9112; p<0.0001), suggesting a minimum $NT_{50}$ titer level of 926 mIU/mL for protection against Stealth infection versus the current 210 mIU/mL used a predictor of seroconversion against the vaccine virus (Haralambieva et al., *Vaccine*, 29:4485-91 (2011)).

The following was performed to determine which extent the breadth and magnitude of the antibody response impacted the antigenic variation seen in Stealth Virus. The antigenic variation was measured in a guinea pig model, which was shown to induce higher titers of cross-reactive antibodies against influenza virus than of mice or ferrets (Nachbagauer et al., *Nat. Immunol.*, 18(4):464-73 (2017)). In the context of MeV, guinea pigs mounted a highly neutralizing antibody response to the homologous vaccine virus with an $NT_{50}$ value of 3584 mIU/mL (FIG. 14D). Conversely, the $ND_{50}$ titer against the heterologous the Stealth virus was ~6-fold lower ($NT_{50}$=563), and therefore antigenically significant. These results indicate that immunodominance was largely conserved across specifies and that antigenic variation can be generated so as to escape the protective levels induced upon vaccination.

Stealth is Solely CD46 Tropic

Figure 15:
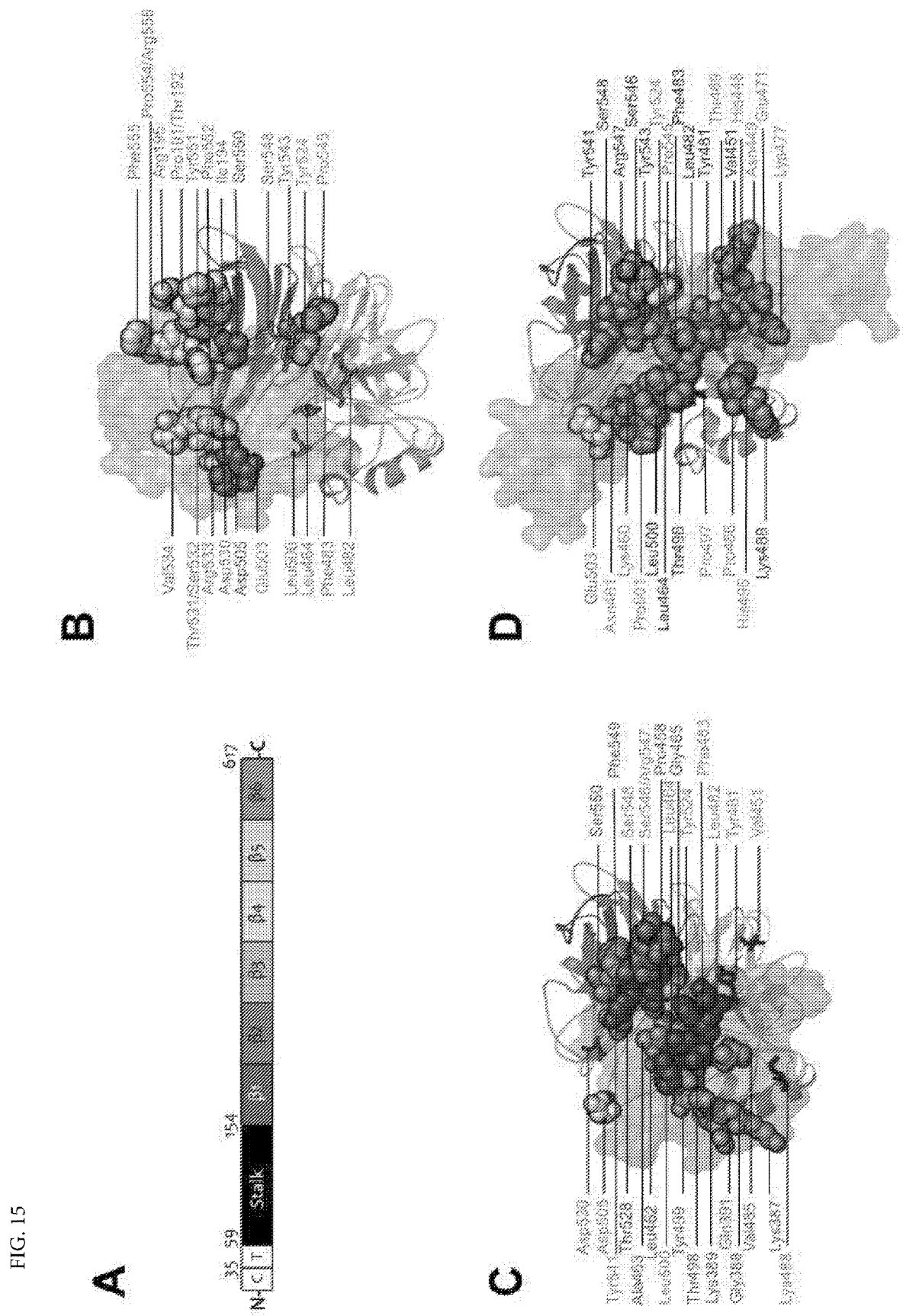
FIGS. 15A-D. Comparison of the receptors' footprint in MeV-H. (A) Schematic representation of the MeV-H primary sequence. From left to right: C, cytoplasmic tail; T, transmembrane domain; Stalk domain; β1-6, beta-propeller blades 1-6. Amino acid positions delineating the different domains are indicated. (B to D) MeV-H is shown as a ribbon with a rainbow coloring consistent with panel A, whereas the receptors are shown as translucent surface colored in cyan (SLAM, panel A), magenta (nectin-4, panel B) and blue (CD46, panel C). Spheres denote residues ≤4.5 Å from receptor entity SLAM (PDB: 3ALZ), nectin-4 (PDB: 4GJT) and CD46 (PDB: 3INB), colored in cyan, magenta and blue, respectively. In each MeV-H-receptor complex structure, spheres are colored differently to the receptor coloring if the residue is also relevant for the interaction with in any of the others receptors, and colored accordingly. Residue Y524 relevant for the interaction with all three receptors is colored in orange. For comparison, the MeV-H orientation is kept consistent across panels. Stick representation depict residues structurally involved as defined by <4.5A from the receptor entity, but not functionally (L464, L482, F483, L500, D530, Y543, S548) and vice versa (V451, N-Y481, K488, P497) (Mateo et al., *J. Virol.*, 87(16):9208-16 (2013)).
Figure 16:
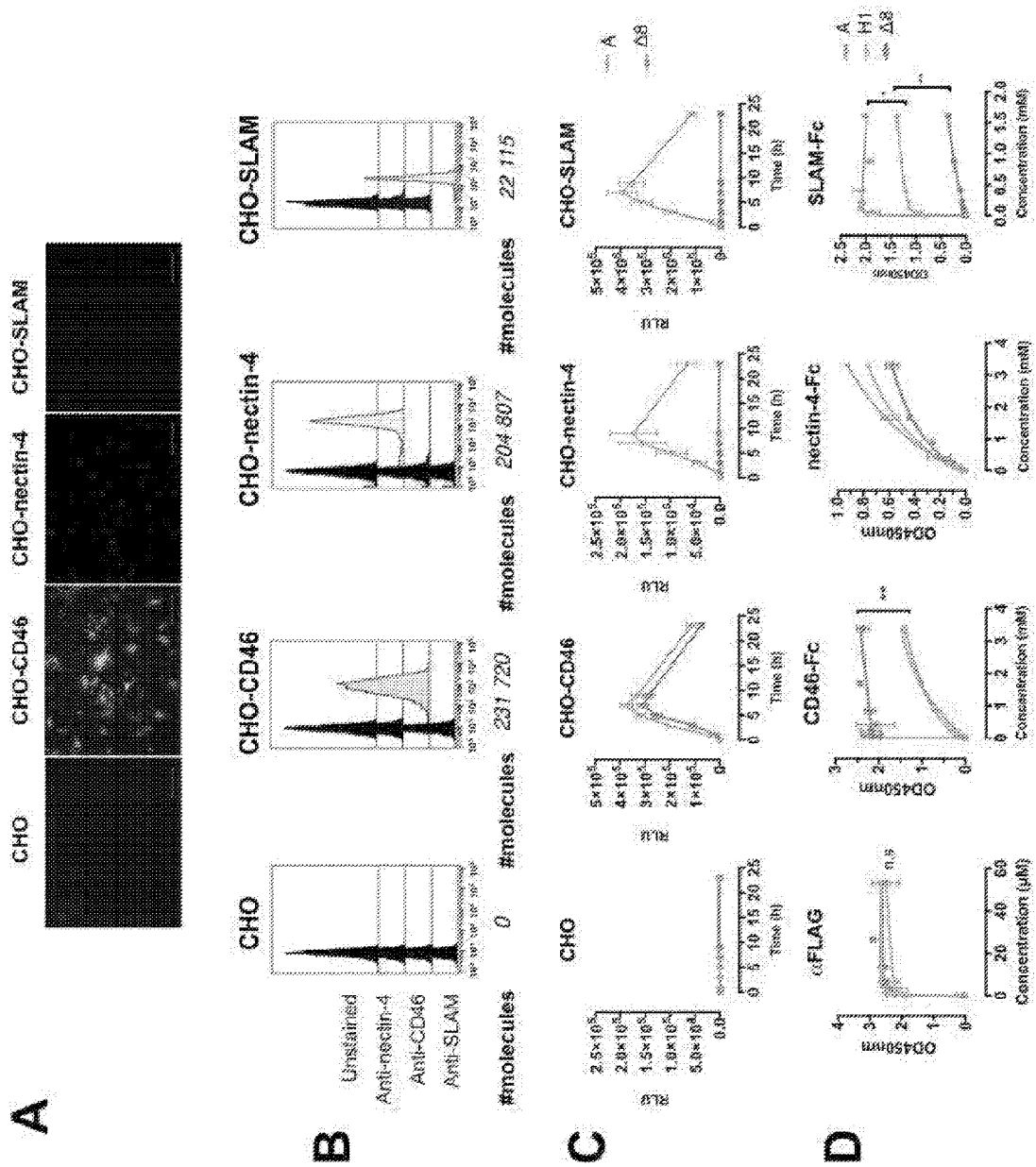
FIGS. 16A-D. Receptor usage for Stealth. (A) Stealth virus infection of a panel of CHO cells expressing or not the MeV receptors. Infection was done at MOI 0.03 and recorded 3 days later. Magnification ×40. (B) Flow cytometry to determine the surface expression of the MeV receptors in the CHO panel. Cells were stained with the relevant antibody, and the number of molecules per cell was determined with Quantibrite BD. (C) Kinetics fusion assay after co-expression of MeV-F vaccine strain with either MeV-H vaccine strain or MeV-HΔ8. Mean±standard deviation (n=3). (D) Binding of MeV receptors-Fc to plastic-bound MeV-H protein, monitored by OD (FIG. 18). Data points are presented as mean±standard deviation (n=3) and were fitted to a one-site mode of total binding ($R^2 \geq 0.99$). *$P<0.05$*$P<0.005$;*$P<0.0001$. One-way ANOVA with the Bonferroni's multiple comparisons.
Figure 17:
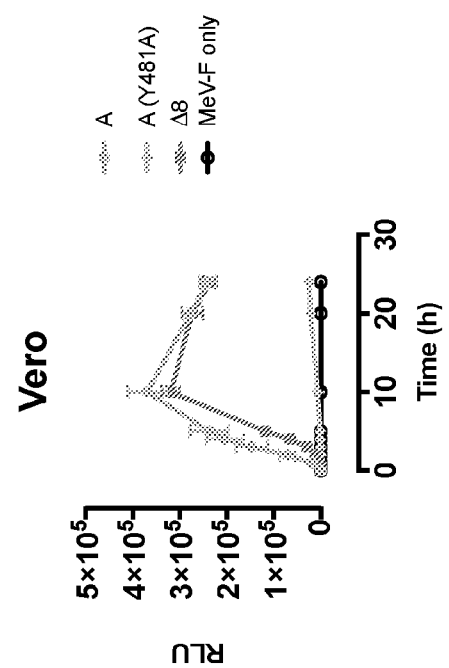
FIG. 17. Kinetic fusion assay on vero cells. MeV-H vaccine strain or Δ8 were co-transfected together with MeV-F vaccine strain. Fusion was quantified by split-luciferase assay. Transfection of MeV-F alone served as negative control. Mean±standard deviation of a representative experiment performed in triplicate.
Figure 19:
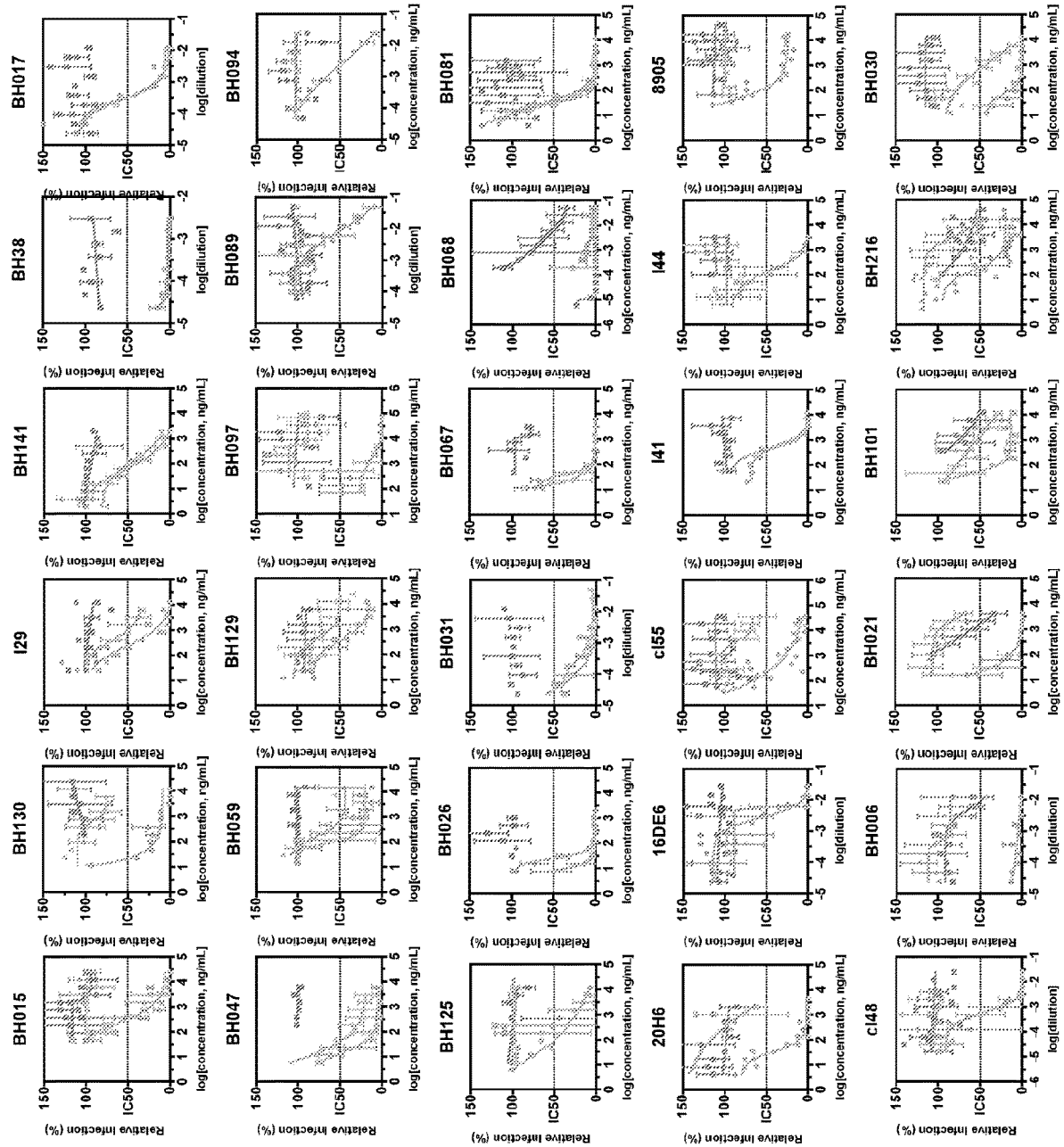
FIG. 19. PRMN assay of anti-MeV-H mAbs. Results are expressed as % of virus control in the absence of mAb. Data are presented as mean±standard deviation of two independent experiments performed in quadruplicate.
Figure 20:
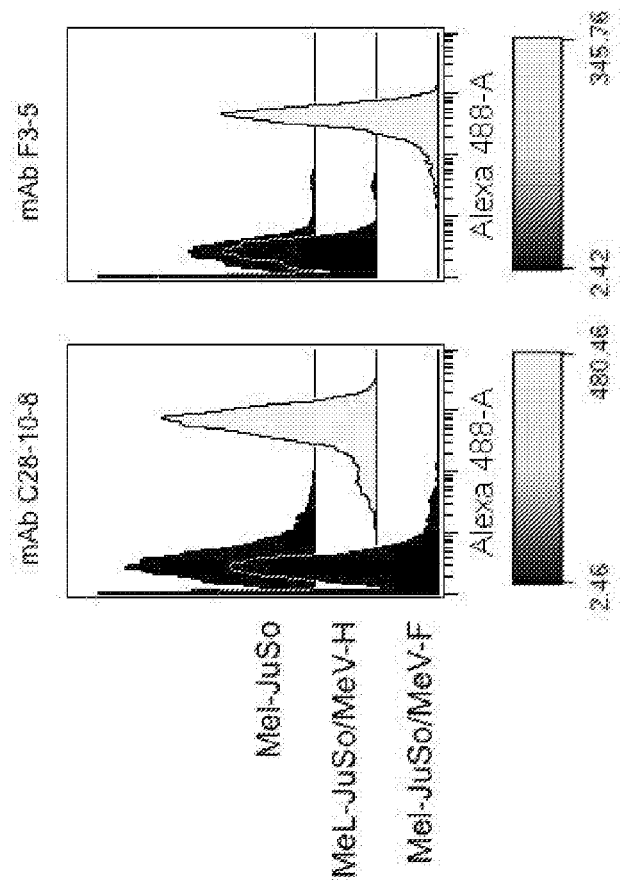
FIG. 20. Flow cytometry to characterize MeV-glycoprotein expression on Mel-JuSo cell lines. Parental Mel-JuSO cells and Mel-JuSO cells expressing either MeV-H or MeV-F were stained with anti-MeV-H (C28-10-8) or anti-MeV-F (F3-5) mAb and results are shown as histograms.
Figure 21:
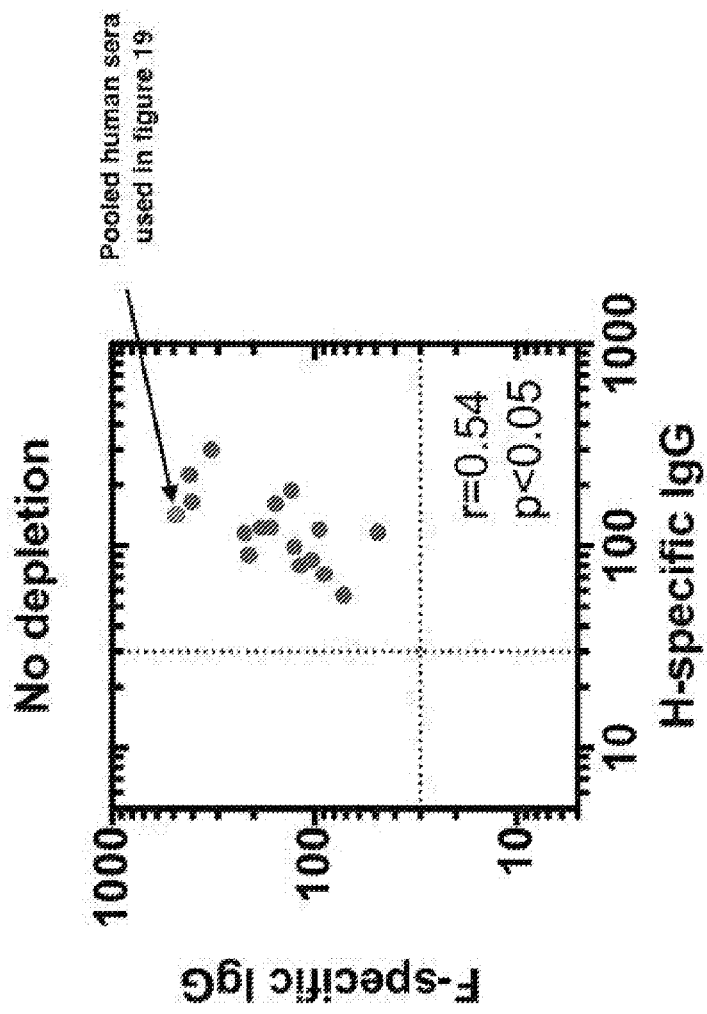
FIG. 21. Correlation analysis for levels of IgG MeV-H and MeV-F-specific antibodies. Black dots represent single vaccinated individuals. Arrow indicates a pooled human sera (Valley Biomedical). Statistical analysis performed with a two-tailed Pearson correlation.

In influenza A viruses, receptor binding avidity and antigenic variation are closely related (Hensley et al., *Science*, 326:734-6 (2009); and Li et al., *J. Virol.*, 87(17):9904-10 (2013)) and can compensate loss of viral fitness (Kosik et al., *PLoS Pathog.*, 14(1):e1006796 (2018)). To begin to address if receptor specificities are affected when nAb-escape mutations are present, CHO cells singly expressing the MeV receptors were infected. Unexpectedly, given the intimately structural and functional interaction between CD46 and nectin-4 (FIG. 15), Stealth virus proved to produce highly efficient CD46-dependent fusion but did not show any in nectin-4-expressing CHO cells (FIG. 16A). Differences in receptor density were excluded as potential explanation for the discrimination of CD46 over nectin-4 usage since the number of molecules on the cell surface was comparable between them two and it was 10-fold higher than that on SLAM-expressing CHO cells (~20,000) (FIG. 16B). Similar results were obtained when the panel of CHO cells were infected with Δ8 viruses, encoding the same MeV-HΔ8 as in Stealth, which argues against allosteric interaction between MeV-H Δ8 and CDV-F as the causative reason. However, further interactions with MeV matrix protein (MeV-M) could still influence receptor-binding interactions. Then, whether a transient transfection based fusion assay would parallel the results observed in the context of the virus was studied. The approach was to use MeV-F in combination with either MeV-H A or MeV-HΔ8. The indicated that MeV-HΔ8 discriminated nectin-4 without significantly affected CD46-dependent fusion (FIG. 16C). Similar CD46-dependent fusion activity was observed with both human and African green monkey cells (FIG. 17). The receptor binding disassociation constants were examined for the various recombinant MeV-H proteins (A, H1, and Δ8) by ELISA (FIG. 18). Unlike the anti-FLAG antibody used as a control, the recombinant cellular receptors showed differential binding avidity for the MeV-H proteins (FIG. 16D). MeV-H Δ8 bound approximately 4000-fold better to CD46 than did MeV-H A and H1, with an apparent $K_d$ of 190 pM versus 819 μM for MeV-H A ($K_d$ was ambiguous). Binding values for nectin-4 were the worst across all three receptors, and saturation was not achieved at the highest concentration used. Even though no significant differences appeared for the apparent $K_d$ of nectin-4 to the recombinant MeV-H proteins, $B_{max}$ values for MeV-HΔ8 were decreased approximately by a half in comparison to MeV-H A and H1 (1.56, 1.14, and 0.74, respectively). As expected, MeV-H Δ8 showed negligible binding to SLAM-Fc. MeV-H H1 showed lower binding to SLAM-Fc than MeV-H A, with $K_d$ of 10.43 μM and 2.68 μM, but $B_{max}$ values were also lower (2.09 and 1.19, respectively). Together, these results demonstrate that MeV-H Δ8 discriminates CD46 usage over nectin-4 via an increase in the avidity interaction with CD46 while decreasing that for nectin-4.

As described herein, 30 known antibody epitopes were systematically eliminated from the measles H glycoprotein. Viruses having that measles H glycoprotein demonstrated resistance to neutralization by anti-H antibodies present in measles-immune human, mouse and rabbit serum. In addition, substitution of the measles F glycoprotein with the homologous F protein of a related morbillivirus was used to generate MeV stealth, a recombinant MeV resistant to neutralization by measles-immune human serum. The virus was shown to remain fully fusogenic and grow solely in CD46-positive cells with no cost in virus fitness. These results demonstrate that the MeV stealth platform can be used for oncolytic virotherapy in measles-immune cancer patients.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant measles virus comprising:
   a nucleic acid encoding a measles virus H polypeptide comprising at least six amino acid substitutions as compared to a wild-type measles virus H polypeptide; and
   a nucleic acid encoding a canine distemper virus F polypeptide.

2. The virus of claim 1, wherein said encoded measles virus H polypeptide and said canine distemper virus F polypeptide are incorporated into the envelope of said recombinant measles virus.

3. The virus of claim 1, wherein said virus exhibits CD46-dependent cell entry.

4. The virus of claim 3, wherein said virus exhibits reduced Nectin-4-dependent cell entry relative to a wild type measles virus.

5. The virus of claim 1, wherein said virus lacks said measles virus F polypeptide, lacks nucleic acid encoding said measles virus F polypeptide, or lacks both said measles virus F polypeptide and said nucleic acid encoding said measles virus F polypeptide.

6. The virus of claim 1, wherein said virus lacks said wild-type measles virus H polypeptide, lacks nucleic acid encoding said wild-type measles virus H polypeptide, or lacks both said wild-type measles virus H polypeptide and said nucleic acid encoding said wild-type measles virus H polypeptide.

7. A method for reducing the number of viable tumor cells in a mammal, said method comprising administering to said mammal a recombinant measles virus comprising:
   a nucleic acid encoding a measles virus H polypeptide comprising at least six amino acid substitutions as compared to a wild-type measles virus H polypeptide; and
   a nucleic acid encoding a canine distemper virus F polypeptide.

8. The method of claim 7, wherein said mammal is a human.

9. A method for stimulating an immune response against measles virus in a mammal, said method comprises administering to said mammal a recombinant measles virus comprising:
- a nucleic acid encoding a measles virus H polypeptide comprising at least six amino acid substitutions as compared to a wild-type measles virus H polypeptide; and
- a nucleic acid encoding a canine distemper virus F polypeptide.

10. The method of claim 9, where said mammal is an infant.

11. The method of claim 10, wherein said infant is a human infant.

12. The method of claim 11, wherein said human infant has transplacentally acquired anti-measles antibodies.

* * * * *

SEQUENCE LISTING

<160> NUMBER OF SEQ ID NOS: 15

<210> SEQ ID NO 1
<211> LENGTH: 617
<212> TYPE: PRT
<213> ORGANISM: measles virus

<400> SEQUENCE: 1

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Leu Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr

```
                    165                 170                 175
Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
            195                 200                 205

Tyr Leu Gly Arg Gly Tyr Asn Val Ser Ser Ile Val Thr Met Thr Ser
            210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
                260                 265                 270

Thr Asn Tyr Leu Glu Gln Pro Val Ser Asn Asp Leu Ser Asn Cys Met
            275                 280                 285

Val Ala Leu Gly Glu Leu Lys Leu Ala Ala Leu Cys His Gly Glu Asp
            290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
                340                 345                 350

Ser His Arg Gly Val Ile Ala Asp Asn Gln Ala Lys Trp Ala Val Pro
            355                 360                 365

Thr Thr Arg Thr Asp Asp Lys Leu Arg Met Glu Thr Cys Phe Gln Gln
            370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
                420                 425                 430

Pro Leu Ile Thr His Gly Ser Gly Met Asp Leu Tyr Lys Ser Asn His
            435                 440                 445

Asn Asn Val Tyr Trp Leu Thr Ile Pro Pro Met Lys Asn Leu Ala Leu
            450                 455                 460

Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
            515                 520                 525

Tyr Asp Thr Ser Arg Val Glu His Ala Val Val Tyr Tyr Val Tyr Ser
            530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590
```

His Ile Thr His Ser Gly Met Val Gly Met Gly Val Ser Cys Thr Val
            595                 600                 605
Thr Arg Glu Asp Gly Thr Asn Arg Arg
    610                 615

<210> SEQ ID NO 2
<211> LENGTH: 1854
<212> TYPE: DNA
<213> ORGANISM: measles virus

<400> SEQUENCE: 2

| | | | | | |
|---|---|---|---|---|---|
| atgtcaccgc | aaagagaccg | gataaatgcc | ttctacaaag | ataacccttta | tcccaaggga | 60 |
| agtaggatag | ttattaacag | agaacatctt | atgattgaca | gaccctatat | tctgctggct | 120 |
| gttctgttcg | tcatgtttct | gagcttgatc | ggattgctgg | caattgcagg | cattagactt | 180 |
| catcgggcag | ccatctacac | cgcggagatc | cataaaagcc | tcagtaccaa | tctagatgtg | 240 |
| actaactcaa | tcgagcatca | ggtcaaggac | gtgctgacac | cactctttaa | aatcatcggg | 300 |
| gatgaagtgg | gcctgagaac | acctcagaga | ttcactgacc | tagtgaaatt | catctctgac | 360 |
| aagattaaat | tccttaatcc | ggatagggag | tacgacttca | gagatctcac | ttggtgcatc | 420 |
| aacccgccag | agaggatcaa | actagattat | gatcaatact | gtgcagatgt | ggctgctgaa | 480 |
| gagctcatga | atgcattggt | gaactcaact | ctactggaga | ccagaacaac | caatcagttc | 540 |
| ctagctgtct | caaagggaaa | ctgctcaggg | cccactacaa | tcagaggtca | attctcaaac | 600 |
| atgtcgctgt | ccttgttgga | cttgtactta | ggtcgaggtt | acaatgtgtc | atctatagtc | 660 |
| actatgacat | cccagggaat | gtatgggga | acctacctag | tggaaaagcc | taatctgaac | 720 |
| agcaaagggt | cagagttgtc | acaactgagc | atgtaccgag | tgtttgaagt | aggtgttatc | 780 |
| agaaacccgg | gtttggggc | tccggtgttc | catatgacaa | actattttga | gcaaccagtc | 840 |
| agtaatggtc | tcggcaactg | tatggtggct | ttggggggag | ctcaaactcgc | agccctttgt | 900 |
| cacggggacg | attctatcac | aattccctat | cagggatcag | ggaaaggtgt | cagcttccag | 960 |
| ctcgtcaagc | tgggtgtctg | gaaatcccca | accgacatgc | aatcctgggt | cccccttatca | 1020 |
| acggatgatc | cagtggtaga | caggctttac | ctctcatctc | acagaggtgt | catcgctgac | 1080 |
| aatcaagcaa | atgggctgt | cccgacaaca | cgaacagatg | acaagttgcg | aatggagaca | 1140 |
| tgcttccagc | aggcgtgtaa | aggtaaaatc | caagcactct | gcgagaatcc | cgagtgggtg | 1200 |
| ccattgaagg | ataacaggat | tccttcatac | ggggtcctgt | ctgttgatct | gagtctgaca | 1260 |
| gttgagctta | aaatcaaaat | tgcttcggga | ttcgggccat | tgatcacaca | cggctcaggg | 1320 |
| atggacctat | acaaatccaa | ccgcaacaat | gtgtattggc | tgactattcc | gccaatgaga | 1380 |
| aatctagcct | taggcgtaat | caacacattg | gagtggatac | cgagattcaa | ggttagtccc | 1440 |
| aacctcttca | ctgtcccaat | taaggaagca | ggcgaggact | gccatgcccc | aacatacctta | 1500 |
| cctgcggagg | tggacggtga | tgtcaaactc | agttccaacc | tggtgattct | acctggtcaa | 1560 |
| gatctccaat | atgttttggc | aacctacgat | acctccaggg | ttgagcatgc | tgtggtttat | 1620 |
| tacgtttaca | gcccaagccg | ctcatttttct | tactttttatc | cttttaggtt | gcctataaag | 1680 |
| ggggtcccaa | tcgaactaca | agtggaatgc | ttcacatgg | accaaaaact | ctggtgccgt | 1740 |
| cacttctgtg | tgcttgcgga | ctcagaatcc | ggcggacata | tcactcactc | tgggatggtg | 1800 |
| ggcatgggag | tcagctgcac | agctacccgg | gaagatggaa | ccaatcgcag | ataa | 1854 |

<210> SEQ ID NO 3

<211> LENGTH: 617
<212> TYPE: PRT
<213> ORGANISM: Artificial Sequence
<220> FEATURE:
<223> OTHER INFORMATION: construct sequence

<400> SEQUENCE: 3

```
Met Ser Pro Gln Arg Asp Arg Ile Asn Ala Phe Tyr Lys Asp Asn Pro
1               5                   10                  15

His Ser Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asn Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Pro Gly Pro Thr
            180                 185                 190

Thr Ile Arg Gly Gln Phe Ser Asn Met Ser Leu Ser Leu Leu Asp Leu
        195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Gly Lys Pro Asp Leu Asn
225                 230                 235                 240

Ser Lys Gly Ser Glu Leu Ser Gln Pro Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Phe Glu Gln Pro Ile Ser Lys Asp Leu Ser Asn Cys Met
        275                 280                 285

Val Ala Leu Gly Glu Leu Lys Leu Ala Ala Leu Cys His Arg Gly Asp
    290                 295                 300

Ser Ile Thr Ile Pro Cys Arg Gly Ser Gly Lys Gly Val Ser Phe Gln
305                 310                 315                 320

Leu Val Lys Leu Gly Val Trp Lys Ser Pro Thr Asp Met His Ser Trp
                325                 330                 335

Val Pro Leu Ser Thr Asp Asp Pro Val Ile Asp Arg Leu Tyr Leu Ser
            340                 345                 350

Ser His Arg Gly Val Ile Thr Asp Asn Gln Ala Asn Trp Ala Val Pro
        355                 360                 365

Thr Thr Arg Thr Asp Asp Lys Leu Gln Lys Glu Thr Cys Phe Gln Gln
    370                 375                 380
```

Ala Cys Lys Gly Lys Ile Gln Ala Leu Cys Glu Asn Leu Glu Trp Ala
385 390 395 400

Pro Leu Lys Asp Ser Arg Ile Pro Ser Tyr Gly Val Leu Ser Val Asn
405 410 415

Leu Ser Leu Ala Ala Glu Pro Lys Ile Lys Ile Ala Ser Gly Phe Gly
420 425 430

Pro Leu Ile Thr His Gly Ser Gly Met Asp Leu Tyr Lys Ser Asn His
435 440 445

Asn Asn Val Tyr Trp Leu Thr Ile Pro Pro Met Lys Asn Leu Ala Leu
450 455 460

Gly Val Ile Asn Thr Leu Glu Trp Ile Pro Arg Leu Lys Val Ser Pro
465 470 475 480

Tyr Leu Phe Thr Val Pro Ile Glu Glu Ala Asp Glu Asp Cys Arg Ala
485 490 495

Pro Thr Tyr Leu Pro Ala Glu Val Thr Gly Asp Val Lys Leu Ser Ser
500 505 510

Asn Leu Val Ile Leu Pro Gly Gln Asp Leu Gln Tyr Val Leu Ala Thr
515 520 525

Tyr Asp Thr Ser Gly Val Glu His Ala Val Val Tyr Tyr Val Tyr Ser
530 535 540

Pro Gly Gly Ser Phe Ser Tyr Val Tyr Pro Phe Arg Leu Pro Ile Lys
545 550 555 560

Gly Thr Pro Ile Glu Leu Gln Val Glu Cys Phe Thr Trp Ala Gln Arg
565 570 575

Leu Trp Cys Arg His Phe Cys Val Leu Ala Asp Ser Glu Ser Gly Gly
580 585 590

His Leu Thr His Ser Gly Met Val Gly Met Glu Val Ser Cys Thr Val
595 600 605

Asn Arg Glu Asp Glu Ala Asn Arg Arg
610 615

<210> SEQ ID NO 4
<211> LENGTH: 553
<212> TYPE: PRT
<213> ORGANISM: measles virus

<400> SEQUENCE: 4

Met Ser Ile Met Gly Leu Lys Val Asn Val Ser Ala Ile Phe Met Ala
1 5 10 15

Val Leu Leu Thr Leu Gln Thr Pro Thr Gly Gln Ile His Trp Gly Asn
20 25 30

Leu Ser Lys Ile Gly Val Val Gly Ile Gly Ser Ala Ser Tyr Lys Val
35 40 45

Met Thr Arg Ser Ser His Gln Ser Leu Val Ile Lys Leu Met Pro Asn
50 55 60

Ile Thr Leu Leu Asn Asn Cys Thr Arg Val Glu Ile Ala Glu Tyr Arg
65 70 75 80

Arg Leu Leu Arg Thr Val Leu Glu Pro Ile Arg Asp Ala Leu Asn Ala
85 90 95

Met Thr Gln Asn Ile Arg Pro Val Gln Ser Val Ala Ser Ser Arg Arg
100 105 110

His Lys Arg Phe Ala Gly Val Val Leu Ala Gly Ala Ala Leu Gly Val
115 120 125

Ala Thr Ala Ala Gln Ile Thr Ala Gly Ile Ala Leu His Gln Ser Met

```
             130                 135                 140
Leu Asn Ser Gln Ala Ile Asp Asn Leu Arg Ala Ser Leu Glu Thr Thr
145                 150                 155                 160

Asn Gln Ala Ile Glu Thr Ile Arg Gln Ala Gly Gln Glu Met Ile Leu
                165                 170                 175

Ala Val Gln Gly Val Gln Asp Tyr Ile Asn Asn Glu Leu Ile Pro Ser
                180                 185                 190

Met Asn Gln Leu Ser Cys Asp Leu Ile Gly Gln Lys Leu Gly Leu Lys
                195                 200                 205

Leu Leu Arg Tyr Tyr Thr Glu Ile Leu Ser Leu Phe Gly Pro Ser Leu
210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255

Gly Asp Leu Leu Gly Ile Leu Glu Ser Gly Gly Ile Lys Ala Arg Ile
                260                 265                 270

Thr His Val Asp Thr Glu Ser Tyr Phe Ile Val Leu Ser Ile Ala Tyr
                275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
                340                 345                 350

Pro Met Ser Pro Leu Leu Gln Glu Cys Leu Arg Gly Tyr Thr Lys Ser
                355                 360                 365

Cys Ala Arg Thr Leu Val Ser Gly Ser Phe Gly Asn Arg Phe Ile Leu
                370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
                420                 425                 430

Ile Gln Val Gly Ser Arg Arg Tyr Pro Asp Ala Val Tyr Leu His Arg
                435                 440                 445

Ile Asp Leu Gly Pro Pro Ile Ser Leu Glu Arg Leu Asp Val Gly Thr
                450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
                500                 505                 510

Ile Pro Ala Leu Ile Cys Cys Cys Arg Gly Arg Cys Asn Lys Lys Gly
                515                 520                 525

Glu Gln Val Gly Met Ser Arg Pro Gly Leu Lys Pro Asp Leu Thr Gly
                530                 535                 540

Thr Ser Lys Ser Tyr Val Arg Ser Leu
545                 550
```

<210> SEQ ID NO 5
<211> LENGTH: 1653
<212> TYPE: PRT
<213> ORGANISM: measles virus

<400> SEQUENCE: 5

```
Ala Thr Gly Gly Gly Thr Cys Thr Cys Ala Ala Gly Thr Gly Ala
 1               5                  10                  15

Ala Cys Gly Thr Cys Thr Cys Thr Gly Cys Cys Gly Thr Ala Thr Thr
                20                  25                  30

Cys Ala Thr Gly Gly Cys Ala Gly Thr Ala Cys Thr Gly Thr Thr Ala
                35                  40                  45

Ala Cys Thr Cys Thr Cys Cys Ala Ala Cys Ala Cys Cys Cys Gly
                50                  55                  60

Cys Cys Gly Gly Thr Cys Ala Ala Thr Thr Cys Ala Thr Thr Gly
65                  70                  75                  80

Gly Gly Gly Cys Ala Ala Thr Cys Thr Cys Thr Ala Ala Gly
                85                  90                  95

Ala Thr Ala Gly Gly Gly Thr Ala Gly Thr Ala Gly Gly Ala Ala
                100                 105                 110

Thr Ala Gly Gly Ala Ala Gly Thr Gly Cys Ala Ala Gly Cys Thr Ala
                115                 120                 125

Cys Ala Ala Ala Gly Thr Thr Ala Thr Gly Ala Cys Thr Cys Gly Thr
                130                 135                 140

Thr Cys Cys Ala Gly Cys Cys Ala Thr Cys Ala Ala Thr Cys Ala Thr
145                 150                 155                 160

Thr Ala Gly Thr Cys Ala Thr Ala Ala Thr Thr Ala Ala Thr
                165                 170                 175

Gly Cys Cys Cys Ala Ala Thr Thr Ala Cys Thr Cys Thr Cys
                180                 185                 190

Cys Thr Cys Ala Ala Thr Ala Ala Cys Thr Gly Cys Ala Cys Gly Ala
                195                 200                 205

Gly Gly Gly Thr Ala Gly Ala Gly Ala Thr Thr Gly Cys Ala Gly Ala
                210                 215                 220

Ala Thr Ala Cys Ala Gly Gly Ala Gly Ala Cys Thr Ala Cys Thr Ala
225                 230                 235                 240

Ala Gly Ala Ala Cys Ala Gly Thr Thr Thr Gly Gly Ala Ala Cys
                245                 250                 255

Cys Ala Ala Thr Thr Ala Gly Gly Gly Ala Thr Gly Cys Ala Cys Thr
                260                 265                 270

Thr Ala Ala Thr Gly Cys Ala Ala Thr Gly Ala Cys Cys Cys Ala Gly
                275                 280                 285

Ala Ala Cys Ala Thr Ala Ala Gly Gly Cys Cys Gly Gly Thr Thr Cys
                290                 295                 300

Ala Gly Ala Gly Cys Gly Thr Ala Gly Cys Thr Cys Ala Ala Gly
305                 310                 315                 320

Thr Ala Gly Gly Ala Gly Ala Cys Ala Cys Ala Ala Gly Ala Gly Ala
                325                 330                 335

Thr Thr Thr Gly Cys Gly Gly Gly Ala Gly Thr Ala Gly Cys Cys
                340                 345                 350

Thr Gly Gly Cys Ala Gly Thr Gly Cys Gly Gly Cys Cys Cys Thr
                355                 360                 365

Ala Gly Gly Thr Gly Thr Thr Gly Cys Cys Ala Cys Ala Gly Cys Thr
```

-continued 370 375 380

Gly Cys Thr Cys Ala Gly Ala Thr Ala Ala Cys Ala Gly Cys Cys Gly
385 390 395 400

Gly Cys Ala Thr Thr Gly Cys Ala Cys Thr Thr Cys Ala Cys Cys Gly
405 410 415

Gly Thr Cys Cys Ala Thr Gly Cys Thr Gly Ala Ala Cys Thr Cys Thr
420 425 430

Cys Ala Gly Gly Cys Cys Ala Thr Cys Gly Ala Cys Ala Ala Thr Cys
435 440 445

Thr Gly Ala Gly Ala Gly Cys Gly Ala Gly Cys Cys Thr Gly Gly Ala
450 455 460

Ala Ala Cys Thr Ala Cys Thr Ala Ala Thr Cys Ala Gly Gly Cys Ala
465 470 475 480

Ala Thr Thr Gly Ala Gly Gly Cys Ala Ala Thr Cys Ala Gly Ala Cys
485 490 495

Ala Ala Gly Cys Ala Gly Gly Gly Cys Ala Gly Gly Ala Gly Ala Thr
500 505 510

Gly Ala Thr Ala Thr Thr Gly Gly Cys Thr Gly Thr Thr Cys Ala Gly
515 520 525

Gly Gly Thr Gly Thr Cys Cys Ala Ala Gly Ala Cys Thr Ala Cys Ala
530 535 540

Thr Cys Ala Ala Thr Ala Ala Thr Gly Ala Gly Cys Thr Gly Ala Thr
545 550 555 560

Ala Cys Cys Gly Thr Cys Thr Ala Thr Gly Ala Ala Cys Cys Ala Gly
565 570 575

Cys Thr Ala Thr Cys Thr Thr Gly Thr Gly Ala Thr Cys Thr Ala Ala
580 585 590

Thr Cys Gly Gly Thr Cys Ala Gly Ala Ala Gly Cys Thr Cys Gly Gly
595 600 605

Gly Cys Thr Cys Ala Ala Ala Thr Thr Gly Cys Thr Thr Ala Gly Ala
610 615 620

Thr Ala Cys Thr Ala Thr Ala Cys Ala Gly Ala Ala Ala Thr Cys Cys
625 630 635 640

Thr Gly Thr Cys Ala Thr Thr Ala Thr Thr Thr Gly Gly Cys Cys Cys
645 650 655

Cys Ala Gly Cys Cys Thr Ala Cys Gly Gly Gly Ala Cys Cys Cys Cys
660 665 670

Ala Thr Ala Thr Cys Thr Gly Cys Gly Gly Ala Gly Ala Thr Ala Thr
675 680 685

Cys Thr Ala Thr Cys Cys Ala Gly Gly Cys Thr Thr Thr Gly Ala Gly
690 695 700

Thr Thr Ala Thr Gly Cys Ala Cys Thr Thr Gly Gly Ala Gly Gly Ala
705 710 715 720

Gly Ala Thr Ala Thr Cys Ala Ala Thr Ala Ala Gly Gly Thr Gly Thr
725 730 735

Thr Ala Gly Ala Ala Ala Ala Gly Cys Thr Cys Gly Gly Ala Thr Ala
740 745 750

Cys Ala Gly Thr Gly Gly Ala Gly Gly Cys Gly Ala Thr Thr Thr Ala
755 760 765

Cys Thr Ala Gly Gly Cys Ala Thr Cys Thr Thr Ala Gly Ala Gly Ala
770 775 780

Gly Cys Ala Gly Ala Gly Gly Ala Ala Thr Ala Ala Ala Gly Gly Cys
785 790 795 800

-continued

```
Thr Cys Gly Gly Ala Thr Ala Ala Cys Thr Cys Ala Cys Gly Thr Cys
                805                 810                 815

Gly Ala Cys Ala Cys Ala Gly Ala Gly Thr Cys Cys Thr Ala Cys Thr
            820                 825                 830
Thr Cys Ala Thr Ala Gly Thr Cys Cys Thr Cys Ala Gly Thr Ala Thr
        835                 840                 845

Ala Gly Cys Cys Thr Ala Thr Cys Cys Gly Ala Cys Gly Cys Thr Gly
    850                 855                 860

Thr Cys Cys Gly Ala Gly Ala Thr Thr Ala Ala Gly Gly Gly Gly Gly
865                 870                 875                 880

Thr Gly Ala Thr Thr Gly Thr Cys Cys Ala Cys Cys Gly Gly Cys Thr
                885                 890                 895

Ala Gly Ala Gly Gly Gly Gly Gly Thr Cys Thr Cys Gly Thr Ala Cys
            900                 905                 910
Ala Ala Cys Ala Thr Ala Gly Gly Cys Thr Cys Thr Cys Ala Ala Gly
        915                 920                 925

Ala Gly Thr Gly Gly Thr Ala Thr Ala Cys Cys Ala Cys Thr Gly Thr
    930                 935                 940

Gly Cys Cys Cys Ala Ala Gly Thr Ala Thr Gly Thr Thr Gly Cys Ala
945                 950                 955                 960

Ala Cys Cys Cys Ala Ala Gly Gly Gly Thr Ala Cys Cys Thr Thr Ala
                965                 970                 975

Thr Cys Thr Cys Gly Ala Ala Thr Thr Thr Thr Gly Ala Thr Gly Ala
            980                 985                 990
Gly Thr Cys Ala Thr Cys Ala Thr  Gly Thr Ala Cys Thr  Thr Thr Cys
        995                 1000                1005

Ala Thr  Gly Cys Cys Ala Gly  Ala Gly Gly Gly Gly  Ala Cys Thr
    1010                 1015                 1020

Gly Thr  Gly Thr Gly Cys Ala  Gly Cys Cys Ala Ala  Ala Ala Thr
    1025                 1030                 1035

Gly Cys  Cys Thr Thr Gly Thr  Ala Cys Cys Cys Gly  Ala Thr Gly
    1040                 1045                 1050

Ala Gly  Thr Cys Cys Thr Cys  Thr Gly Cys Thr Cys  Cys Ala Ala
    1055                 1060                 1065

Gly Ala  Ala Thr Gly Cys Cys  Thr Cys Cys Gly Gly  Gly Gly Gly
    1070                 1075                 1080

Thr Cys  Cys Ala Cys Cys Ala  Ala Gly Thr Cys Cys  Thr Gly Thr
    1085                 1090                 1095

Gly Cys  Thr Cys Gly Thr Ala  Cys Ala Cys Thr Cys  Gly Thr Ala
    1100                 1105                 1110

Thr Cys  Cys Gly Gly Gly Thr  Cys Thr Thr Thr Thr  Gly Gly Gly
    1115                 1120                 1125

Ala Ala  Cys Cys Gly Gly Thr  Thr Cys Ala Thr Thr  Thr Thr Ala
    1130                 1135                 1140

Thr Cys  Ala Cys Ala Ala Gly  Gly Gly Ala Ala Cys  Cys Thr Ala
    1145                 1150                 1155

Ala Thr  Ala Gly Cys Cys Ala  Ala Thr Thr Gly Thr  Gly Cys Ala
    1160                 1165                 1170

Thr Cys  Ala Ala Thr Thr Cys  Thr Thr Thr Gly Thr  Ala Ala Gly
    1175                 1180                 1185

Thr Gly  Thr Thr Ala Cys Ala  Cys Ala Ala Cys Ala  Gly Gly Thr
    1190                 1195                 1200
```

-continued

Ala Cys Gly Ala Thr Thr Ala Thr Thr Ala Ala Thr Cys Ala Ala
1205 1210 1215

Gly Ala Cys Cys Cys Thr Gly Ala Cys Ala Ala Gly Ala Thr Cys
1220 1225 1230

Cys Thr Ala Ala Cys Ala Thr Ala Cys Ala Thr Thr Gly Cys Thr
1235 1240 1245

Gly Cys Cys Gly Ala Thr Cys Gly Cys Thr Gly Cys Cys Cys Gly
1250 1255 1260

Gly Thr Ala Gly Thr Cys Gly Ala Gly Gly Thr Gly Ala Ala Cys
1265 1270 1275

Gly Gly Cys Gly Thr Gly Ala Cys Cys Ala Thr Cys Cys Ala Ala
1280 1285 1290

Gly Thr Cys Gly Gly Gly Ala Gly Cys Ala Gly Gly Ala Gly Gly
1295 1300 1305

Thr Ala Thr Cys Cys Ala Gly Ala Cys Gly Cys Thr Gly Thr Gly
1310 1315 1320

Thr Ala Cys Thr Thr Gly Cys Ala Cys Ala Gly Ala Ala Thr Thr
1325 1330 1335

Gly Ala Cys Cys Thr Cys Gly Gly Thr Cys Cys Thr Cys Cys Cys
1340 1345 1350

Ala Thr Ala Thr Cys Ala Thr Thr Gly Gly Ala Gly Ala Gly Gly
1355 1360 1365

Thr Thr Gly Gly Ala Cys Gly Thr Ala Gly Gly Gly Ala Cys Ala
1370 1375 1380

Ala Ala Thr Cys Thr Gly Gly Gly Gly Ala Ala Thr Gly Cys Ala
1385 1390 1395

Ala Thr Thr Gly Cys Cys Ala Ala Ala Thr Thr Gly Gly Ala Gly
1400 1405 1410

Gly Ala Thr Gly Cys Cys Ala Ala Gly Gly Ala Ala Thr Thr Gly
1415 1420 1425

Thr Thr Gly Gly Ala Ala Thr Cys Ala Thr Cys Gly Gly Ala Cys
1430 1435 1440

Cys Ala Gly Ala Thr Ala Thr Thr Gly Ala Gly Ala Ala Gly Thr
1445 1450 1455

Ala Thr Gly Ala Ala Ala Gly Gly Thr Thr Thr Ala Thr Cys Gly
1460 1465 1470

Ala Gly Cys Ala Cys Thr Ala Gly Cys Ala Thr Ala Gly Thr Cys
1475 1480 1485

Thr Ala Cys Ala Thr Cys Cys Thr Gly Ala Thr Thr Gly Cys Ala
1490 1495 1500

Gly Thr Gly Thr Gly Thr Cys Thr Thr Gly Gly Ala Gly Gly Gly
1505 1510 1515

Thr Thr Gly Ala Thr Ala Gly Gly Gly Ala Thr Cys Cys Cys Cys
1520 1525 1530

Ala Cys Thr Thr Thr Ala Ala Thr Ala Thr Gly Thr Thr Gly Cys
1535 1540 1545

Thr Gly Cys Ala Gly Gly Gly Gly Gly Cys Gly Thr Thr Gly Thr
1550 1555 1560

Ala Ala Cys Ala Ala Ala Ala Ala Gly Gly Gly Ala Gly Ala Ala
1565 1570 1575

Cys Ala Ala Gly Thr Thr Gly Gly Thr Ala Thr Gly Thr Cys Ala
1580 1585 1590

Ala Gly Ala Cys Cys Ala Gly Gly Cys Cys Thr Ala Ala Ala Gly

```
               1595                1600                1605

Cys Cys Thr Gly Ala Cys Cys Thr Thr Ala Cys Ala Gly Gly Ala
    1610                1615                1620

Ala Cys Ala Thr Cys Ala Ala Ala Ala Thr Cys Cys Thr Ala Thr
    1625                1630                1635

Gly Thr Ala Ala Gly Ala Thr Cys Gly Cys Thr Thr Thr Gly Ala
    1640                1645                1650

<210> SEQ ID NO 6
<211> LENGTH: 662
<212> TYPE: PRT
<213> ORGANISM: canine distemper virus

<400> SEQUENCE: 6

Met His Asn Lys Asn Pro Lys Lys Ser Lys Pro Leu Pro His Thr Arg
1               5                   10                  15

Gln Asp Pro Leu Gln Gln His Ser Thr Arg Ser Ala Glu Thr Lys Thr
            20                  25                  30

Ser Gln Gly Gln His Ser Thr Thr Ser Ala Gln Arg Ser Thr Tyr His
        35                  40                  45

Gly Pro Arg Thr Ser Asp Arg Ser Val His Tyr Ile Met Asn Arg Thr
    50                  55                  60

Arg Ser Cys Lys Gln Thr Ser His Arg Ser Asp Asn Ile Pro Pro His
65                  70                  75                  80

Arg Asp His Glu Gly Ile Ile His Thr Pro Glu Ser Val Thr Gln
            85                  90                  95

Gly Ala Ser Ser Trp Phe Lys Arg Gln Ser Asn Ala Thr Asn Ala
        100                 105                 110

Gly Ser Gln Tyr Thr Trp Leu Val Leu Trp Cys Ile Gly Ile Ala Ser
    115                 120                 125

Leu Leu Leu Cys Ser Lys Ala Gln Ile His Trp Asn Asn Leu Ser Thr
130                 135                 140

Ile Gly Ile Ile Gly Thr Asp Ser Val His Tyr Lys Ile Met Thr Arg
145                 150                 155                 160

Pro Ser His Gln Tyr Leu Val Ile Lys Leu Met Pro Asn Val Ser Leu
                165                 170                 175

Ile Asp Asn Cys Thr Lys Ala Glu Leu Gly Glu Tyr Glu Lys Leu Leu
            180                 185                 190

Asn Ser Val Leu Glu Pro Ile Asn Gln Ala Leu Thr Leu Met Thr Asn
        195                 200                 205

Asn Val Lys Pro Leu Gln Ser Val Gly Ser Gly Arg Arg Gln Arg Arg
    210                 215                 220

Phe Ala Gly Val Val Leu Ala Gly Ala Ala Leu Gly Val Ala Thr Ala
225                 230                 235                 240

Ala Gln Ile Thr Ala Gly Ile Ala Leu His Gln Ser Asn Leu Asn Ala
                245                 250                 255

Gln Ala Ile Gln Ser Leu Arg Thr Ser Leu Glu Gln Ser Asn Lys Ala
            260                 265                 270

Ile Glu Glu Ile Arg Glu Ala Thr Gln Glu Thr Val Ile Ala Val Gln
        275                 280                 285

Gly Val Gln Asp Tyr Val Asn Asn Glu Leu Val Pro Ala Met Gln His
    290                 295                 300

Met Ser Cys Glu Leu Val Gly Gln Arg Leu Gly Leu Lys Leu Leu Arg
305                 310                 315                 320
```

```
Tyr Tyr Thr Glu Leu Leu Ser Ile Phe Gly Pro Ser Leu Arg Asp Pro
                325                 330                 335

Ile Ser Ala Glu Ile Ser Ile Gln Ala Leu Ser Tyr Ala Leu Gly Gly
            340                 345                 350

Glu Ile His Lys Ile Leu Glu Lys Leu Gly Tyr Ser Gly Asn Asp Met
        355                 360                 365

Ile Ala Ile Leu Glu Ser Arg Gly Ile Lys Thr Lys Ile Thr His Val
    370                 375                 380

Asp Leu Pro Gly Lys Leu Ile Ile Leu Ser Ile Ser Tyr Pro Thr Leu
385                 390                 395                 400

Ser Glu Val Lys Gly Val Ile Val His Arg Leu Glu Ala Val Ser Tyr
                405                 410                 415

Asn Ile Gly Ser Gln Glu Trp Tyr Thr Thr Val Pro Lys Tyr Val Ala
            420                 425                 430

Thr Asn Gly Tyr Leu Ile Ser Asn Phe Asp Glu Ser Ser Cys Val Phe
        435                 440                 445

Val Ser Glu Ser Ala Ile Cys Ser Gln Asn Ser Leu Tyr Pro Met Ser
    450                 455                 460

Pro Ile Leu Gln Gln Cys Ile Arg Gly Asp Thr Ser Ser Cys Ala Arg
465                 470                 475                 480

Thr Leu Val Ser Gly Thr Met Gly Asn Lys Phe Ile Leu Ser Lys Gly
                485                 490                 495

Asn Ile Val Ala Asn Cys Ala Ser Ile Leu Cys Lys Cys Tyr Ser Thr
            500                 505                 510

Ser Thr Ile Ile Asn Gln Ser Pro Asp Lys Leu Leu Thr Phe Ile Ala
        515                 520                 525

Ser Asp Thr Cys Pro Leu Val Glu Ile Asp Gly Val Thr Ile Gln Val
    530                 535                 540

Gly Gly Arg Gln Tyr Pro Asp Met Val Tyr Glu Ser Lys Val Ala Leu
545                 550                 555                 560

Gly Pro Ala Ile Ser Leu Glu Arg Leu Asp Val Gly Thr Asn Leu Gly
                565                 570                 575

Asn Ala Leu Lys Lys Leu Asp Asp Ala Lys Val Leu Ile Asp Ser Ser
            580                 585                 590

Asn Gln Ile Leu Glu Thr Val Lys Arg Ser Ser Phe Asn Phe Gly Ser
        595                 600                 605

Leu Leu Ser Val Pro Ile Leu Ile Cys Thr Ala Leu Ala Leu Leu Leu
    610                 615                 620

Leu Ile Tyr Cys Cys Lys Arg Arg Tyr Arg Gln Thr Phe Lys His Asn
625                 630                 635                 640

Thr Lys Val Asp Pro Thr Phe Lys Pro Asp Leu Thr Gly Thr Ser Lys
                645                 650                 655

Ser Tyr Val Arg Ser Leu
            660

<210> SEQ ID NO 7
<211> LENGTH: 662
<212> TYPE: PRT
<213> ORGANISM: canine distemper virus

<400> SEQUENCE: 7

Met His Asn Lys Ile Pro Lys Arg Ser Lys Pro Leu Pro His Thr Arg
1               5                   10                  15

Gln Asp Pro Leu Gln Gln His Ser Thr Arg Phe Gly Glu Thr Thr Thr
            20                  25                  30
```

```
Ser Gln Gly Arg His Ser Thr Ser Ala Gln Arg Ser Thr His His
        35                  40                  45

Gly Pro Arg Thr Ser Asp Arg Pro Val His His Thr Met Asn Arg Thr
50                      55                  60

Arg Ser Cys Lys Gln Thr Ser His Arg Ser Asp Asn Ile Leu Pro His
65                      70                  75                  80

Arg Asp His Lys Gly Ile Ile His His Thr Pro Glu Ser Val Thr Gln
                85                  90                  95

Gly Ala Ser Ser Trp Phe Lys Arg Arg Gln Phe Asn Ala Thr Asn Ala
            100                 105                 110

Gly Ser Gln Cys Thr Trp Leu Val Leu Trp Cys Ile Gly Ile Ala Ser
        115                 120                 125

Leu Phe Leu Cys Ser Lys Ala Gln Ile His Trp Asn Asn Leu Ser Thr
        130                 135                 140

Ile Gly Ile Ile Gly Thr Asp Ser Val His Tyr Lys Ile Met Thr Arg
145                 150                 155                 160

Pro Ser His Gln Tyr Leu Val Ile Lys Leu Met Pro Asn Val Ser Leu
                165                 170                 175

Ile Asp Asn Cys Thr Lys Ala Glu Leu Gly Glu Tyr Glu Lys Leu Leu
            180                 185                 190

Asn Ser Val Leu Glu Pro Ile Asn Gln Ala Leu Thr Leu Met Thr Asn
        195                 200                 205

Asn Val Lys Pro Leu Gln Ser Val Gly Ser Gly Arg Arg Gln Arg Arg
        210                 215                 220

Phe Ala Gly Val Val Leu Ala Gly Ala Ala Leu Gly Val Ala Thr Ala
225                 230                 235                 240

Ala Gln Ile Thr Ala Gly Ile Ala Leu His Gln Ser Asn Leu Asn Ala
            245                 250                 255

Gln Ala Ile Gln Ser Leu Arg Thr Ser Leu Glu Gln Ser Asn Lys Ala
            260                 265                 270

Ile Glu Glu Ile Arg Glu Ala Thr Gln Glu Thr Val Ile Ala Val Gln
        275                 280                 285

Gly Val Gln Asp Tyr Val Asn Asn Glu Leu Val Pro Ala Met Gln His
        290                 295                 300

Met Ser Cys Glu Leu Val Gly Gln Arg Leu Gly Leu Lys Leu Leu Arg
305                 310                 315                 320

Tyr Tyr Thr Glu Leu Leu Ser Ile Phe Gly Pro Ser Leu Arg Asp Pro
            325                 330                 335

Ile Ser Ala Glu Ile Ser Ile Gln Ala Leu Ser Tyr Ala Leu Gly Gly
            340                 345                 350

Glu Ile His Lys Ile Leu Glu Lys Leu Gly Tyr Ser Gly Asn Asp Met
        355                 360                 365

Ile Ala Ile Leu Glu Ser Arg Gly Ile Lys Thr Lys Ile Thr His Val
        370                 375                 380

Asp Leu Pro Gly Lys Leu Ile Ile Leu Ser Ile Ser Tyr Pro Thr Leu
385                 390                 395                 400

Ser Glu Val Lys Gly Val Ile Val His Arg Leu Glu Thr Val Ser Tyr
            405                 410                 415

Asn Ile Gly Ser Gln Glu Trp Tyr Thr Thr Val Pro Lys Tyr Val Ala
            420                 425                 430

Thr Asn Gly Tyr Leu Ile Ser Asn Phe Asp Glu Ser Ser Cys Val Phe
        435                 440                 445
```

```
Phe Ser Glu Ser Ala Ile Cys Ser Gln Asn Ser Leu Tyr Pro Met Ser
    450                 455                 460

P

-continued

Lys Ala Ile Ala Ser Ala Ala Asn Pro Ile Leu Leu Ser Ala Leu Ser
                165                 170                 175

Gly Gly Arg Gly Asp Ile Phe Pro Pro His Arg Cys Ser Gly Ala Thr
            180                 185                 190

Thr Ser Val Gly Lys Val Phe Pro Leu Ser Val Ser Leu Ser Met Ser
        195                 200                 205

Leu Ile Ser Arg Thr Ser Glu Val Ile Asn Met Leu Thr Ala Ile Ser
    210                 215                 220

Asp Gly Val Tyr Gly Lys Thr Tyr Leu Leu Val Pro Asp Asp Ile Glu
225                 230                 235                 240

Arg Glu Phe Asp Thr Arg Glu Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Lys Asn Ser Lys Ala Lys Val Cys Thr Ile Ala Val Gly
        275                 280                 285

Glu Leu Thr Leu Ala Ser Leu Cys Val Glu Glu Ser Thr Val Leu Leu
    290                 295                 300

Tyr His Asp Ser Ser Gly Ser Gln Asp Gly Ile Leu Val Val Thr Leu
305                 310                 315                 320

Gly Ile Phe Trp Ala Thr Pro Met Asp His Ile Glu Glu Val Ile Pro
                325                 330                 335

Val Ala His Pro Ser Met Lys Lys Ile His Ile Thr Asn His Arg Gly
            340                 345                 350

Phe Ile Lys Asp Ser Ile Ala Thr Trp Met Val Pro Ala Leu Ala Ser
        355                 360                 365

Glu Lys Gln Glu Glu Lys Gly Cys Leu Glu Ser Ala Cys Gln Arg
    370                 375                 380

Lys Thr Tyr Pro Met Cys Asn Gln Ala Ser Trp Glu Pro Phe Gly Gly
385                 390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asp Gly Thr Ile Ser Gly Leu Ile Asn
    450                 455                 460

Lys Ala Gly Arg Gly Asp Gln Phe Thr Val Leu Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Arg Asp Arg Asp Val Leu Ile Glu Ser Asn Ile Val Val
            500                 505                 510

Leu Pro Thr Gln Ser Ile Arg Tyr Val Ile Ala Thr Tyr Asp Ile Ser
        515                 520                 525

Arg Ser Asp His Ala Ile Val Tyr Tyr Val Tyr Asp Pro Ile Arg Thr
530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
                565                 570                 575

```
Gln Phe Tyr Arg Phe Glu Ala Asp Ile Ala Asn Ser Thr Thr Ser Val
                580                 585                 590

Glu Asn Leu Val Arg Ile Arg Phe Ser Cys Asn Arg
            595                 600

<210> SEQ ID NO 9
<211> LENGTH: 617
<212> TYPE: PRT
<213> ORGANISM: measles virus

<400> SEQUENCE: 9

Met Ser Pro Gln Arg Asp Arg Ile Asn Ala Phe Tyr Lys Asp Asn Pro
1               5                   10                  15

His Ser Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asn Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Asn
225                 230                 235                 240

Ser Lys Gly Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Phe Glu Gln Pro Ile Ser Lys Asp Leu Ser Asn Cys Met
        275                 280                 285

Val Ala Leu Gly Glu Leu Lys Leu Ala Ala Leu Cys His Gly Gly Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met His Ser Trp
                325                 330                 335

Val Pro Leu Ser Thr Asp Asp Pro Val Ile Asp Arg Leu Tyr Leu Ser
            340                 345                 350
```

Ser His Arg Gly Val Ile Thr Asp Asn Gln Ala Asn Trp Ala Val Pro
    355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Leu Glu Trp Ala
385                 390                 395                 400

Pro Leu Lys Asp Ser Arg Ile Pro Ser Tyr Gly Val Leu Ser Val Asp
            405                 410                 415

Leu Ser Leu Ala Ala Glu Pro Lys Ile Lys Ile Ala Ser Gly Phe Gly
            420                 425                 430

Pro Leu Ile Thr His Gly Ser Gly Met Asp Leu Tyr Lys Ser Asn His
            435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Leu Lys Val Ser Pro
465                 470                 475                 480

Asn Leu Phe Thr Val Pro Ile Lys Glu Ala Gly Glu Asp Cys His Ala
            485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
    515                 520                 525

Tyr Asp Thr Ser Arg Val Glu His Ala Val Val Tyr Val Tyr Ser
530                 535                 540

Pro Ser Arg Ser Phe Ser Tyr Phe Tyr Pro Phe Arg Leu Pro Ile Lys
545                 550                 555                 560

Gly Thr Pro Ile Glu Leu Gln Val Glu Cys Phe Thr Trp Ala Gln Arg
            565                 570                 575

Leu Trp Cys Arg His Phe Cys Val Leu Ala Asp Ser Glu Ser Gly Gly
            580                 585                 590

His Leu Thr His Ser Gly Met Val Gly Met Glu Val Ser Cys Thr Val
    595                 600                 605

Asn Arg Glu Asp Glu Ala Asn Arg Arg
    610                 615

<210> SEQ ID NO 10
<211> LENGTH: 6
<212> TYPE: DNA
<213> ORGANISM: Artificial Sequence
<220> FEATURE:
<223> OTHER INFORMATION: construct sequence

<400> SEQUENCE: 10 gggaga                                                              6

<210> SEQ ID NO 11
<211> LENGTH: 17
<212> TYPE: DNA
<213> ORGANISM: Artificial Sequence
<220> FEATURE:
<223> OTHER INFORMATION: construct sequence

<400> SEQUENCE: 11
taatacgact cactata                                                 17

<210> SEQ ID NO 12
<211> LENGTH: 68

```
<212> TYPE: DNA
<213> ORGANISM: Artificial Sequence
<220> FEATURE:
<223> OTHER INFORMATION: construct sequence

<400> SEQUENCE: 12
taatacgact cactataggg agatgtttgg tctgatgagg ccgaaaggcc gaaactccgt    60
aaggagtc                                                            68

<210> SEQ ID NO 13
<211> LENGTH: 70
<212> TYPE: DNA
<213> ORGANISM: Artificial Sequence
<220> FEATURE:
<223> OTHER INFORMATION: construct sequence

<400> SEQUENCE: 13
taatacgact cactataggg agatttggtc tgatgagtcc gtgaggacga aacggagtct    60
agactccgtc                                                          70

<210> SEQ ID NO 14
<211> LENGTH: 70
<212> TYPE: DNA
<213> ORGANISM: Artificial Sequence
<220> FEATURE:
<223> OTHER INFORMATION: construct sequence

<400> SEQUENCE: 14
taatacgact cactataggg agatttggtc tgatgagtcc gtgaggacga aacggagtct    60
agactccgtc                                                          70

<210> SEQ ID NO 15
<211> LENGTH: 21
<212> TYPE: PRT
<213> ORGANISM: Artificial Sequence
<220> FEATURE:
<223> OTHER INFORMATION: construct sequence

<400> SEQUENCE: 15

Lys Asn Leu Ala Leu Gly Val Ile Asn Thr Leu Glu Trp Ile Pro Arg
1               5                   10                  15

Phe Lys Val Ser Pro
            20
```